United States Patent
Feng et al.

(10) Patent No.: US 11,345,948 B2
(45) Date of Patent: May 31, 2022

(54) METHOD FOR DETECTING CHROMOSOME ROBERTSONIAN TRANSLOCATION

(71) Applicant: PEKING JABREHOO TECHNOLOGY CO. LTD, Beijing (CN)

(72) Inventors: Tao Feng, Beijing (CN); Jia Fei, Beijing (CN)

(73) Assignee: PEKING JABREHOO TECHNOLOGY CO. LTD, Beijing (CN)

( * ) Notice: Subject to any disclaimer, the term of this patent is extended or adjusted under 35 U.S.C. 154(b) by 370 days.

(21) Appl. No.: 16/068,749

(22) PCT Filed: Jan. 19, 2016

(86) PCT No.: PCT/CN2016/070696
§ 371 (c)(1),
(2) Date: Jul. 9, 2018

(87) PCT Pub. No.: WO2017/124214
PCT Pub. Date: Jul. 27, 2017

(65) Prior Publication Data
US 2019/0032119 A1    Jan. 31, 2019

(51) Int. Cl.
*C12Q 1/6827*    (2018.01)
*C12Q 1/6883*    (2018.01)

(52) U.S. Cl.
CPC ......... *C12Q 1/6827* (2013.01); *C12Q 1/6883* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2008/0243398 A1* 10/2008 Rabinowitz .......... C12Q 1/6855
702/20

FOREIGN PATENT DOCUMENTS

CN        105543372 A        5/2016

OTHER PUBLICATIONS

Tan (Human Reproduction, vol. 28, No. 9 pp. 2581-2592, 2013).*
The World Intellectual Property Organization (WIPO) International Search Report for PCT/CN2016/070696 dated Oct. 19, 2016 8 Pages.
Nathan, R.T. et al., "Use of Single Nucleotide Polymorphism Microarrays to Distinguish 1-23 between Balanced and Normal Chromosomes in Embryos from A Translocation Carrier", Fertility and Sterility, vol. 96, No. 1, Jul. 31, 2011, ISSN: e58-e65, abstract, and the section of materials and methods.
Zhang, Fan, Chromosome Disease and Diagnosis, Dec. 31, 2006, 1-23 figures 3-6, and p. 42.

* cited by examiner

*Primary Examiner* — Amanda Haney
(74) *Attorney, Agent, or Firm* — Anova Law Group, PLLC

(57) ABSTRACT

Provided is a method for detecting chromosomal Robertsonian translocation and the SNP (single nucleotide polymorphism) site and primer composition for use therein. The method is practical, simple, convenient and high in universality; moreover, a high-throughput sequencing technology is combined, so that the method has the advantages of low cost, and high sensitivity, specificity and accuracy.

3 Claims, 5 Drawing Sheets
Specification includes a Sequence Listing.

METHOD FOR DETECTING CHROMOSOME ROBERTSONIAN TRANSLOCATION

CROSS-REFERENCE TO RELATED APPLICATION

The present application is a national phase entry under 35 U.S.C. § 371 of International Application No. PCT/CN2016/070696, filed on Jan. 19, 2016, the content of which is hereby incorporated by reference in its entity.

SEQUENCE LISTING

The present application contains a Sequence Listing which has been submitted via EFSWeb and is hereby incorporated by reference in its entirety. The ASCII copy, created on Jul. 9, 2018, is named 00242_0001sequencelisting.txt, and is 156 kilobytes in size.

TECHNICAL FIELD

The present disclosure relates to molecular diagnosis and particularly relates to a method for detecting chromosomal Robertsonian translocation, which is capable of detecting normal and translocation carrying embryo and fetus, of which the parents have pedigree of Robertsonian translocation.

BACKGROUND

Robertsonian translocation (ROB) is named according to the American biologist William Rees Brebner Robertson who for the first time found the translocation pattern and is a chromosomal translocation mainly occurring in 5 acrocentric chromosomes (Chromosome 13, Chromosome 14, Chromosome 15, Chromosome 21 and Chromosome 22) (Robertson WRB. Chromosome studies. I. Taxonomic relationships shown in the chromosomes of Tettigidae and Acrididae. V-shaped chromosomes and their significance in Acrididae, Locustidae and Gryllidae: chromosome and variation. J Morph 1916, 27: 179-331). When two acrocentric chromosome break at centromere or a location in proximity to centromere, their long arms bind at centromere forming a derived chromosome composed of long arms, which is also known as centromere fusion, one of chromosomal balanced translocations. Two short arms form a small chromosome, which always loses in a second division. Robertsonian translocation is a common chromosomal abnormal structure, of which the newborn occurrence rate is 1.23/1000 (Nielsen J, Wohlert M. Chromosome abnormalities found among 34910 newborn children: results from 13-year incidence study in Arhus, Denmark. Hum Genet. 1991, 87: 81-83). As the short arm of chromosome mainly comprises random repeated DNA and ribosome RNA genes, which are present in all of the five chromosome, there is loss of short arm of chromosome in Robertsonian translocation, it does not results in pathogenic phenotype. Although the phenotype is normal, during the Pt meiosis of carrier's germ cell, the translocation chromosome and two corresponding normal chromosome will match to form trivalent chromosome and such a structure will result in three division patterns, i.e. alternate, neighborhood and uncommon 3:0 division patterns, of which only the alternate pattern will lead to normal or balanced gametes and others will lead to unbalanced gametes. The dominating unbalanced gametes will lead to difficulty in pregnancy or recurrent abortion in pregnancy, and even lead to birth of children with congenital defect like 13-Patau syndrome with abnormal chromosome copy number in translocation carrier. Now more and more Robertsonian translocation carriers seek for test-tube baby technology for preimplantation genetic diagnosis.

The test-tube baby is a technology that ovum and sperm are taken to put in a special culture liquid for culture, fertilization, and the oosperm develops into an embryo in a thermostat incubator, which is then transplanted into parent uterus where it develops into a fetus finally.

A key of successful prevention lies in selecting health embryo for transplant. Preimplantation genetic screen refers to detection of chromosome number and abnormal structure before implantation and nidation of an embryo, selection for an embryo with normal chromosome for implantation into uterus, so as to give normal progeny. The current preimplantation genetic diagnosis for Robertsonian translocation comprises SNP chip and fluorescence in situ hybridization (FISH). The SNP chip is the most commonly used detection technology, which however can only detect embryo chromosome copy number change but cannot differentiate normal embryo from translocation carrying translocation in Robertsonian translocation. FISH uses specific nucleic acid probe labeled with fluorescence to hybrid with corresponding target DNA molecule in cells, and fluorescence signal is observed under fluorescence microscope to determine the location of DNA molecule bound with fluorescence probe in chromosome. Nevertheless, FISH as a method for examine single nucleus has some defect as 7% false negative rate (Colls P, Escudero T, Cekleniak N, Sadowy S, Cohen J, Munné S. Increased efficiency of preimplantation genetic diagnosis for infertility using "no result rescue". Fertil Steril. 2007, 88(1): 53-61).

Spontaneous abortion is a common disease in gynaecology and obstetrics, of which the occurrence rate account for 10%-15% of all the pregnancy. The occurrence rate is determined by many factors, like embryo factor, placenta factor, parent factor, environmental factor or the like, wherein abnormal embryo chromosome is the main cause of abortion.

Chromosomal examination on abortion tissue for the causes of embryo developmental arrest, abortion provides theoretical basis for clinical counsel and guideline for subsequent pregnancy. Now FISH technology is for use in performing common abnormal chromosome on missed abortion villus and tissues at different locations of a fetus. FISH as a targeted detecting technology has limited commercial probes and was limited by the type, amount and high cost of the probes. It cannot detect a large number of abnormal genes or chromosome. Additionally, due to the limit of FISH, it cannot be used to detect chromosomal abnormal structure, leading to missed diagnosis of some patients with chromosomal abnormal structure (L I, Yangyang, Zhang Qin, Current study of analysis of spontaneous abortion villus chromosome karyotype, Journal of Obstetrics and Gynaecology, 2012, 28: 431-433).

In a summary, it is desired to develop a novel method to detect Robertsonian translocation of embryo and abortion tissue in test-tube baby technology.

SUMMARY

Provided is a method for detecting chromosomal Robertsonian translocation based on high-throughput sequencing technology so as to screen fully normal and translocation carrying embryo, fetus or abortion tissue.

In the first aspect, provided is a method for detecting chromosomal Robertsonian translocation, comprising the steps of:

(1) obtaining DNA samples from both of the parents and the progeny;

(2) screening hypermutational SNP site from a location in proximity to the centromere of acrocentric chromosome as a marker;

(3) detecting chromosome copy number of the progeny DNA sample;

(4) determining genotypes of the target sites of both of the parents and the progeny according to the SNP site screened in step (2);

(5) analyzing haplotypes of both of the parents and the progeny based on the genotypes and pedigree relations of both of the parents and the progeny;

(6) analyzing the chromosomal Robertsonian translocation of the progeny according to the detecting result of chromosome copy number of the progeny, the karyotypes of both of the parents carrying chromosomal Robertsonian translocation and the haplotypes of both of the parents and the progeny.

Preferably, the method is useful for detecting human chromosomal translocation, particularly the translocation between any two chromosomes of Chromosome 13, Chromosome 14, Chromosome 15, Chromosome 21 and Chromosome 22.

In a specific embodiment, the parental DNA sample is the parental genomic DNA extracted from peripheral blood sample; the progeny DNA sample is selected from the group consisting of trophoblast cell whole genomic amplified products of embryo or fetus or genomic DNA extracted from abortion tissue, preferably blastocyst trophoblast cell whole genomic amplified product of embryo cultured in vitro.

In the above step (2), the screening criteria for SNP site are:

a. the site is within 10 Mb location in proximity to the centromere;

b. the site is collected in 1000 Genomes database or dbSNP database, preferably SNP of which the Minimum Allele Frequency (MAF) in target population is above 0.2;

c. the sequence in proximity to the SNP site is not homologous in human genome.

In a particular embodiment, the SNP sites comprise at least one SNP site, preferably at least 10 SNP sites, more preferably at least 50 SNP sites from every chromosome with translocation.

Preferably, the SNP site is selected from the group consisting of the following SNP sites or any combination thereof: chr13:19602195, chr13:19625370, chr13:19646283, chr13:19692745, chr13:19713634, chr13:19722801, chr13:19732341, chr13:19784913, chr13:19843135, chr13:19877547, chr13:19883672, chr13:19896927, chr13:19917509, chr13:20494558, chr13:20709214, chr13:20747500, chr13:20784332, chr13:20825315, chr13:20864572, chr13:20881859, chr13:20908501, chr13:20938952, chr13:20951425, chr13:20992333, chr13:21012562, chr13:21066214, chr13:21092894, chr13:21112935, chr13:21527671, chr13:21553971, chr13:21575458, chr13:21607760, chr13:21636136, chr13:21655335, chr13:21683681, chr13:21801501, chr13:22197910, chr13:22249975, chr13:22270788, chr13:22340074, chr13:22396664, chr13:22417688, chr13:22473749, chr13:22504691, chr13:22515844, chr13:22523279, chr13:22538311, chr13:22561684, chr13:22640820, chr13:22751654, chr13:22768476, chr13:22780737, chr13:22799808, chr13:22819627, chr13:22835073, chr13:22892864, chr13:22980146, chr14:19472367, chr14:20326905, chr14:20349694, chr14:20383719, chr14:20420387, chr14:20517369, chr14:20527044, chr14:20565487, chr14:20643775, chr14:20670979, chr14:20731036, chr14:20820537, chr14:20905141, chr14:20918598, chr14:21008574, chr14:21048774, chr14:21091127, chr14:21156472, chr14:21195967, chr14:21237137, chr14:21263166, chr14:21313819, chr14:21325985, chr14:21388266, chr14:21452591, chr14:21519915, chr14:21580671, chr14:21625262, chr14:21789092, chr14:21981923, chr14:22053817, chr14:22090208, chr14:22138437, chr14:22210067, chr14:22244363, chr14:22263821, chr14:22312275, chr14:22324460, chr14:22351977, chr14:22361282, chr14:22375208, chr14:22393124, chr14:22428984, chr14:22452496, chr14:22489611, chr14:22518909, chr14:22526966, chr14:22563283, chr14:22611651, chr14:22626948, chr14:22657897, chr14:22702039, chr14:22731529, chr14:22734948, chr14:22741160, chr14:22772663, chr14:22861948, chr14:22972955, chr15:20022190, chr15:20049922, chr15:20189367, chr15:20191854, chr15:20192138, chr15:20454253, chr15:20470948, chr15:20564500, chr15:20569241, chr15:20586537, chr15:20586966, chr15:20590656, chr15:20616721, chr15:20626721, chr15:20646773, chr15:20848359, chr15:20849625, chr15:20852181, chr15:20862156, chr15:20863958, chr15:21905797, chr15:21928397, chr15:21938184, chr15:21940649, chr15:22013203, chr15:22299435, chr15:22302182, chr15:22376163, chr15:22427155, chr15:22441959, chr15:22476195, chr15:22520388, chr15:22539952, chr15:22780065, chr15:22798800, chr15:22833272, chr15:22854479, chr15:22869870, chr15:22893990, chr15:22905599, chr15:22916637, chr15:22923869, chr15:22940961, chr15:22971662, chr15:23000363, chr15:23010627, chr15:23020535, chr15:23044004, chr15:23053813, chr15:23064687, chr15:23721906, chr15:23730971, chr15:23746510, chr15:23767135, chr15:23781336, chr15:23793989, chr15:23816231, chr15:23893430, chr15:23929209, chr15:24006330, chr15:24055535, chr15:24129894, chr15:24166516, chr15:24196094, chr15:24236177, chr15:24278723, chr15:24319610, chr15:24350583, chr15:24471640, chr15:24824114, chr15:24870875, chr15:24913763, chr15:24943341, chr15:24974072, chr21:14640496, chr21:14643423, chr21:14695894, chr21:14756515, chr21:14818516, chr21:14890028, chr21:15012159, chr21:15026905, chr21:15170049, chr21:15280687, chr21:15300595, chr21:15445542, chr21:15479041, chr21:15501432, chr21:15548748, chr21:15566056, chr21:15588845, chr21:15625530, chr21:15654618, chr21:15681452, chr21:15720558, chr21:15763305, chr21:15842397, chr21:15884516, chr21:15916232, chr21:15942816, chr21:15984234, chr21:16027704, chr21:16063848, chr21:16122140, chr21:16160041, chr21:16193235, chr21:16238898, chr21:16315932, chr21:16353639, chr21:16384555, chr21:16448591, chr21:16578538, chr21:16645724, chr21:16717265, chr21:16833315, chr21:16881542, chr21:17000938, chr21:17054831, chr21:17140290, chr21:17203891, chr21:17295288, chr21:17340912, chr21:17536247, chr21:17640426, chr21:17673255, chr21:17713264, chr21:17748703, chr21:17781159, chr21:17823782, chr21:18003355, chr21:18046650, chr21:18114449, chr21:18151760, chr21:18182817, chr21:18250262, chr21:18337678, chr21:18385770, chr21:18420873, chr21:18457287, chr21:

18586049, chr21: 18650837, chr21: 18740886, chr21: 18858018, chr21:18936951, chr21:19002939, chr21: 19064396, chr21:19139888, chr21:19254923, chr21: 19316600, chr22:16415691, chr22: 16554800, chr22: 16848067, chr22: 16850056, chr22: 16850858, chr22: 16851557, chr22: 16852464, chr22: 16852792, chr22: 16853453, chr22: 16854397, chr22:16855647, chr22: 16856500, chr22: 16857432, chr22: 16858287, chr22: 16860547, chr22:16861742, chr22: 16867995, chr22: 17031697, chr22: 17271213, chr22:17293257, chr22: 17409957, chr22:17442318, chr22:17469090, chr22: 17525677, chr22: 17563259, chr22: 17587785, chr22: 17619511, chr22: 17656792, chr22:17682387, chr22: 17715164, chr22: 17739757, chr22: 17761489, chr22: 17785311, chr22: 17805528, chr22: 17841251, chr22: 17883346, chr22: 17916190, chr22: 17939998, chr22: 17981144, chr22: 18012297, chr22:18054406, chr22: 18212058, chr22: 18276198, chr22: 18354015, chr22: 18395978, chr22:18466951, chr22: 18531582, chr22: 18581715, chr22: 18628321, chr22:18894617, chr22: 18966077, chr22:19004846, chr22:19025459, chr22: 19098323, chr22: 19142652, chr22:19236590, chr22: 19362714, chr22: 19431588, chr22: 19536367, chr22: 19643965, chr22:19716983, chr22: 19759532, chr22: 19808057, chr22: 19859087, chr22:19909387, chr22: 19972494, chr22:20016622, chr22:20051573, chr22: 20081918, chr22:20135421, chr22:20175034, chr22: 20216874, chr22:20278637, chr22:20745699, chr22: 20787955, chr22:20855585, chr22:20881195, chr22: 20924097, chr22:20983921, chr22:21028224. Most preferably, the SNP sites comprise all the above SNP sites from every chromosome with translocation.

In a particular embodiment, the process for detecting the chromosome copy number in above step (3) and step (4) is selected independently from the group consisting of sequencing process and chip process. The sequencing process is a high-throughput sequencing process, preferably Ion Torrent PGM or Illumina Miseq; the chip process is human whole genomic SNP chip, preferably Illumina whole genomic SNP chip.

Preferably, in the detecting method according to the invention, one of the parents has normal karyotype, the other carries Robertsonian translocation; the progeny comprises a subject that is Robertsonian translocation chromosome trisomic or monosomic.

Specifically, the determining criteria in step (6) are:

a. if a progeny is chromosome m trisomic, haplotype B in chromosome n from parental Robertsonian translocation carrier is translocation chromosome haplotype, and accordingly another haplotype b in chromosome n from parental Robertsonian translocation carrier is normal chromosome haplotype; and further by observing haplotype of other progeny, chromosome m haplotype A from parental Robertsonian translocation carrier linked with chromosome n haplotype B is translocation chromosome haplotype, and accordingly, another haplotype a in chromosome m from parental Robertsonian translocation carrier is normal chromosome haplotype; thereby it can be determined that the progeny carrying chromosome m haplotype A and chromosome n haplotype B is translocation carrier, and the progeny carrying chromosome m haplotype a and chromosome n haplotype b is normal karyotype;

b. if a progeny is chromosome m monosomic, haplotype B in chromosome n from parental Robertsonian translocation carrier is normal chromosome haplotype, and accordingly another haplotype b in chromosome n from parental Robertsonian translocation carrier is translocation chromosome haplotype; and further by observing haplotype of other progeny, chromosome m haplotype a from parental Robertsonian translocation carrier linked with chromosome n haplotype b is translocation chromosome haplotype, and accordingly another haplotype A in chromosome m from parental Robertsonian translocation carrier is normal chromosome haplotype; thereby it can be determined that the progeny carrying chromosome m haplotype A and chromosome n haplotype B is normal karyotype, and the progeny carrying chromosome m haplotype a and chromosome n haplotype b is translocation carrier;

wherein chromosome m and chromosome n are two chromosomes with Robertsonian translocation in the genome of parental Robertsonian translocation carrier, A and a are haplotypes from parental Robertsonian translocation carrier chromosome m, and B and b are haplotype from parental Robertsonian translocation carrier chromosome n.

Taking chromosomal translocation in Chromosome 13 and Chromosome 14 as an example,

|  | carrier | +13 embryo | +14 embryo | −13 embryo | −14 embryo | translocation embryo | normal embryo |
|---|---|---|---|---|---|---|---|
| Chr13 | Aa | Aa | A | — | a | A | a |
| Chr14 | Bb | B | Bb | b | — | B | b |

According to the above table, if Chromosome 13 is triploid or haploid, it can be inferred that B type in Robertsonian translocation carrier Chromosome 14 is translocation chromosome haplotype, b type is normal chromosome haplotype; according to other embryo carrying B type or b type, it can be further inferred that A type in Chromosome 13 is translocation chromosome haplotype, a type is normal chromosome haplotype;

if Chromosome 14 is triploid or haploid, it can be inferred that A type in Robertsonian translocation carrier Chromosome 13 is translocation chromosome haplotype, a type is normal chromosome haplotype; according to other embryo carrying A type or a type, it can be further inferred that B in Chromosome 14 is translocation chromosome haplotype, b is normal chromosome haplotype.

Therefore, carrier of Chromosome 13 a type and Chromosome 14 b type is normal embryo, and carrier of Chromosome 13 A type and Chromosome 14 B type is translocation carrier embryo.

The method according to the invention is particularly useful for preimplantation genetic diagnosis.

In the second aspect, provided is a primer composition for detecting chromosomal Robertsonian translocation, the primer composition is capable of amplifying the sequence of hypermutational SNP site in proximity to centromere of acrocentric chromosome. Preferably, the primer composition is for use in detecting human chromosomal Robertsonian translocation, particularly a translocation between any two of Chromosome 13, Chromosome 14, Chromosome 15, Chromosome 21 and Chromosome 22.

The screening criteria for SNP site are:
a. the site is within 10Mb location in proximity to the centromere;
b. the site is collected in 1000 Genomes database or dbSNP database, preferably SNP of which the Minimum Allele Frequency (MAF) in target population is above 0.2;
c. the sequence in proximity to the SNP site is not homologous in human genome.

In a specific embodiment, the SNP sites comprise at least one SNP site, preferably at least 10 SNP sites, more preferably at least 50 SNP sites from every chromosome with translocation.

Preferably, the SNP site is selected from the group consisting of the following SNP sites or any combination thereof: chr13:19602195, chr13:19625370, chr13:19646283, chr13:19692745, chr13:19713634, chr13:19722801, chr13:19732341, chr13:19784913, chr13:19843135, chr13:19877547, chr13:19883672, chr13:19896927, chr13:19917509, chr13:20494558, chr13:20709214, chr13:20747500, chr13:20784332, chr13:20825315, chr13:20864572, chr13:20881859, chr13:20908501, chr13:20938952, chr13:20951425, chr13:20992333, chr13:21012562, chr13:21066214, chr13:21092894, chr13:21112935, chr13:21527671, chr13:21553971, chr13:21575458, chr13:21607760, chr13:21636136, chr13:21655335, chr13:21683681, chr13:21801501, chr13:22197910, chr13:22249975, chr13:22270788, chr13:22340074, chr13:22396664, chr13:22417688, chr13:22473749, chr13:22504691, chr13:22515844, chr13:22523279, chr13:22538311, chr13:22561684, chr13:22640820, chr13:22751654, chr13:22768476, chr13:22780737, chr13:22799808, chr13:22819627, chr13:22835073, chr13:22892864, chr13:22980146, chr14: 19472367, chr14:20326905, chr14:20349694, chr14:20383719, chr14:20420387, chr14:20517369, chr14:20527044, chr14:20565487, chr14:20643775, chr14:20670979, chr14:20731036, chr14:20820537, chr14:20905141, chr14:20918598, chr14:21008574, chr14:21048774, chr14:21091127, chr14:21156472, chr14:21195967, chr14:21237137, chr14:21263166, chr14:21313819, chr14:21325985, chr14:21388266, chr14:21452591, chr14:21519915, chr14:21580671, chr14:21625262, chr14:21789092, chr14:21981923, chr14:22053817, chr14:22090208, chr14:22138437, chr14:22210067, chr14:22244363, chr14:22263821, chr14:22312275, chr14:22324460, chr14:22351977, chr14:22361282, chr14:22375208, chr14:22393124, chr14:22428984, chr14:22452496, chr14:22489611, chr14:22518909, chr14:22526966, chr14:22563283, chr14:22611651, chr14:22626948, chr14:22657897, chr14:22702039, chr14:22731529, chr14:22734948, chr14:22741160, chr14:22772663, chr14:22861948, chr14:22972955, chr15:20022190, chr15:20049922, chr15:20189367, chr15:20191854, chr15:20192138, chr15:20454253, chr15:20470948, chr15:20564500, chr15:20569241, chr15:20586537, chr15:20586966, chr15:20590656, chr15:20616721, chr15:20626721, chr15:20646773, chr15:20848359, chr15:20849625, chr15:20852181, chr15:20862156, chr15:20863958, chr15:21905797, chr15:21928397, chr15:21938184, chr15:21940649, chr15:22013203, chr15:22299435, chr15:22302182, chr15:22376163, chr15:22427155, chr15:22441959, chr15:22476195, chr15:22520388, chr15:22539952, chr15:22780065, chr15:22798800, chr15:22833272, chr15:22854479, chr15:22869870, chr15:22893990, chr15:22905599, chr15:22916637, chr15:22923869, chr15:22940961, chr15:22971662, chr15:23000363, chr15:23010627, chr15:23020535, chr15:23044004, chr15:23053813, chr15:23064687, chr15:23721906, chr15:23730971, chr15:23746510, chr15:23767135, chr15:23781336, chr15:23793989, chr15:23816231, chr15:23893430, chr15:23929209, chr15:24006330, chr15:24055535, chr15:24129894, chr15:24166516, chr15:24196094, chr15:24236177, chr15:24278723, chr15:24319610, chr15:24350583, chr15:24471640, chr15:24824114, chr15:24870875, chr15:24913763, chr15:24943341, chr15:24974072, chr21:14640496, chr21:14643423, chr21:14695894, chr21:14756515, chr21:14818516, chr21:14890028, chr21:15012159, chr21:15026905, chr21:15170049, chr21:15280687, chr21:15300595, chr21:15445542, chr21:15479041, chr21:15501432, chr21:15548748, chr21:15566056, chr21:15588845, chr21:15625530, chr21:15654618, chr21:15681452, chr21:15720558, chr21:15763305, chr21:15842397, chr21:15884516, chr21:15916232, chr21:15942816, chr21:15984234, chr21:16027704, chr21:16063848, chr21:16122140, chr21:16160041, chr21:16193235, chr21:16238898, chr21:16315932, chr21:16353639, chr21:16384555, chr21:16448591, chr21:16578538, chr21:16645724, chr21:16717265, chr21:16833315, chr21:16881542, chr21:17000938, chr21:17054831, chr21:17140290, chr21:17203891, chr21:17295288, chr21:17340912, chr21:17536247, chr21:17640426, chr21:17673255, chr21:17713264, chr21:17748703, chr21:17781159, chr21:17823782, chr21:18003355, chr21:18046650, chr21:18114449, chr21:18151760, chr21:18182817, chr21:18250262, chr21:18337678, chr21:18385770, chr21:18420873, chr21:18457287, chr21:18586049, chr21:18650837, chr21:18740886, chr21:18858018, chr21:18936951, chr21:19002939, chr21:19064396, chr21:19139888, chr21:19254923, chr21:19316600, chr22:16415691, chr22:16554800, chr22:16848067, chr22:16850056, chr22: 16850858, chr22:16851557, chr22: 16852464, chr22: 16852792, chr22:16853453, chr22: 16854397, chr22:16855647, chr22:16856500, chr22: 16857432, chr22: 16858287, chr22:16860547, chr22:16861742, chr22: 16867995, chr22:17031697, chr22: 17271213, chr22: 17293257, chr22:17409957, chr22: 17442318, chr22: 17469090, chr22:17525677, chr22: 17563259, chr22: 17587785, chr22:17619511, chr22: 17656792, chr22:17682387, chr22:17715164, chr22: 17739757, chr22: 17761489, chr22:17785311, chr22:17805528, chr22: 17841251, chr22:17883346, chr22: 17916190, chr22: 17939998, chr22:17981144, chr22: 18012297, chr22: 18054406, chr22:18212058, chr22: 18276198, chr22: 18354015, chr22:18395978, chr22:18466951, chr22:18531582, chr22:18581715, chr22:18628321, chr22: 18894617, chr22:18966077, chr22: 19004846, chr22: 19025459, chr22:19098323, chr22: 19142652, chr22:19236590, chr22:19362714, chr22: 19431588, chr22: 19536367, chr22:19643965, chr22:19716983, chr22: 19759532, chr22:19808057, chr22: 19859087, chr22: 19909387, chr22:19972494, chr22:20016622, chr22:20051573, chr22:20081918, chr22:20135421, chr22:20175034, chr22:20216874, chr22:20278637, chr22:20745699, chr22:20787955, chr22:20855585, chr22:20881195, chr22:20924097, chr22:20983921, chr22:21028224. Most preferably, the SNP sites comprise all the above SNP sites from every chromosome with translocation In a particularly preferable embodiment, the primer composition is selected from the group consisting of the following primer pair composed of the following forward primer and reverse primer, or any combination thereof:

(1) the primer for amplifying the SNP site in Chromosome 13, which is selected from the group consisting of following primer pairs: forward primer sequence SEQ ID NO:2n-1, reverse primer sequence SEQ ID NO:2n, n is a natural number selected from 1-57;

(2) the primer for amplifying the SNP site in Chromosome 14, which is selected from the group consisting of following primer pairs: forward primer sequence SEQ ID NO:2n-1, reverse primer sequence SEQ ID NO:2n; wherein n is a natural number selected from 58-115;

(3) the primer for amplifying the SNP site in Chromosome 15, which is selected from the group consisting of following primer pairs: forward primer sequence SEQ ID NO:2n-1, reverse primer sequence SEQ ID NO:2n; wherein n is a natural number selected from 116-189;

(4) the primer for amplifying the SNP site in Chromosome 21, which is selected from the group consisting of following primer pairs: forward primer sequence SEQ ID NO:2n-1, reverse primer sequence SEQ ID NO:2n; wherein n is a natural number selected from 190-264;

(5) the primer for amplifying the SNP site in Chromosome 22, which is selected from the group consisting of following primer pairs: forward primer sequence SEQ ID NO:2n-1, reverse primer sequence SEQ ID NO:2n wherein n is a natural number selected from 265-344.

Preferably, the primer composition comprises at least one pair of primers, preferably at least 10 pairs of primers, more preferably at least 50 pairs of primers for amplifying SNP site in every chromosome with translocation; and most preferably comprises all above primer pairs for amplifying SNP site in every chromosome with translocation.

Provided is also use of the primer composition according to the invention for the manufacture of a diagnostic reagent or kit for detecting chromosomal Robertsonian translocation.

The advantages of the invention are summarized as follows.

Applicability: The invention is capable of solving the detecting issue in embryo, fetus or abortion tissue Robertsonian translocation carrier, which is not possible for conventional methods.

Simplicity and Convenience: In the present invention, analysis of chromosomal translocation of various cells are based on cell chromosome copy number and haplotype without observation of the cells, thereby enable quick differentiation of normal and translocation carrying embryo.

Universality: Poly SNP is used in the present invention for analysis, which can be used in preimplantation genetic diagnosis, fetus diagnosis or abortion tissue diagnosis of different spouses.

High throughput: Based on high-throughput sequencing technology, the invention can be used to analyze chromosomal translocation and by different sequencing tags on each sample, a large number of samples can be analyzed at the same time.

Low cost: The detecting cost of chromosomal translocation of the invention is decreasing with the development of sequencing technology and decrease of sequencing cost.

High sensitivity: The invention can be used on the analysis for 3-5 cells. Accordingly, in addition to abortion tissue, trophoblast cell from cervix, the invention is particularly useful for preimplantation genetic diagnosis in test-tube baby technology.

Specificity: Hypermutational sites with Minimum Allele Frequency >0.2 of CHB (northern Han Chinese) and CHS (southern Han Chinese) within 10 Mb range in proximity to centromere location in chromosome in 1000 Genomes data are selected, wherein polymorphic sites with GC content >70% in polynucleotide (polyN) and upstream and downstream 50 bp sequences are excluded, and SNP mutant site which is uniquely aligned in human genome is selected as target location. Primers are designed by logging in https://www.ampliseq.com/ for submitting target site and location. These primers are highly specific.

Accuracy: According to change of translocation chromosome copy number and the sample carrying corresponding chromosome, the each derived chromosome haplotype in chromosome with translocation can be speculated, and higher accuracy can be achieved with mutual authentication.

BRIEF DESCRIPTION OF THE DRAWINGS

FIG. 3 shows chromosome pedigree haplotype pattern of Chromosome 13 pedigree haplotype in Example 1.

FIG. 4 shows chromosome pedigree haplotype pattern of Chromosome 14 pedigree haplotype in Example 1.

Figure 5:
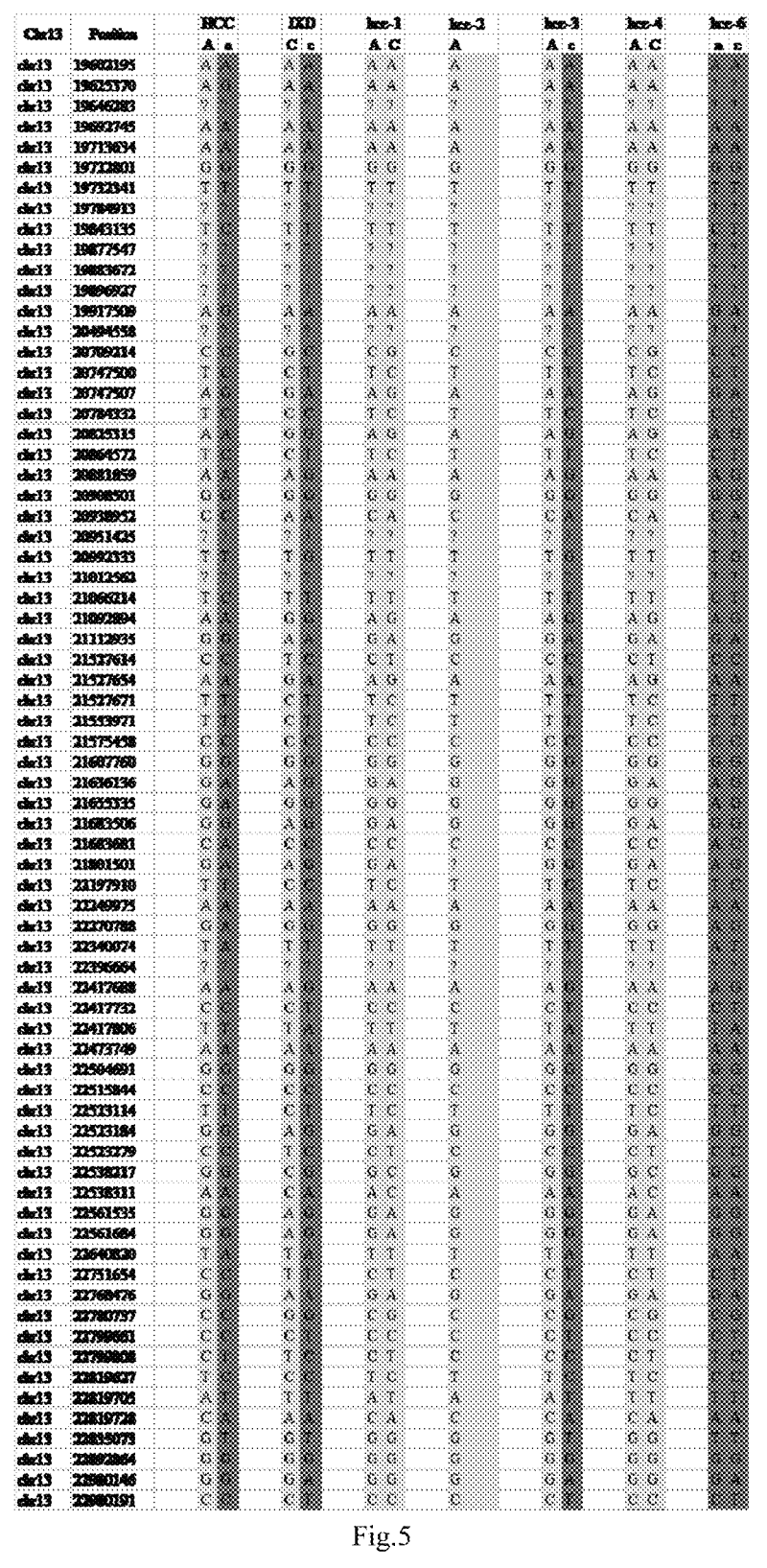

FIG. 5 shows chromosome pedigree haplotype pattern of Chromosome 13 pedigree haplotype in Example 3.

Figure 6:
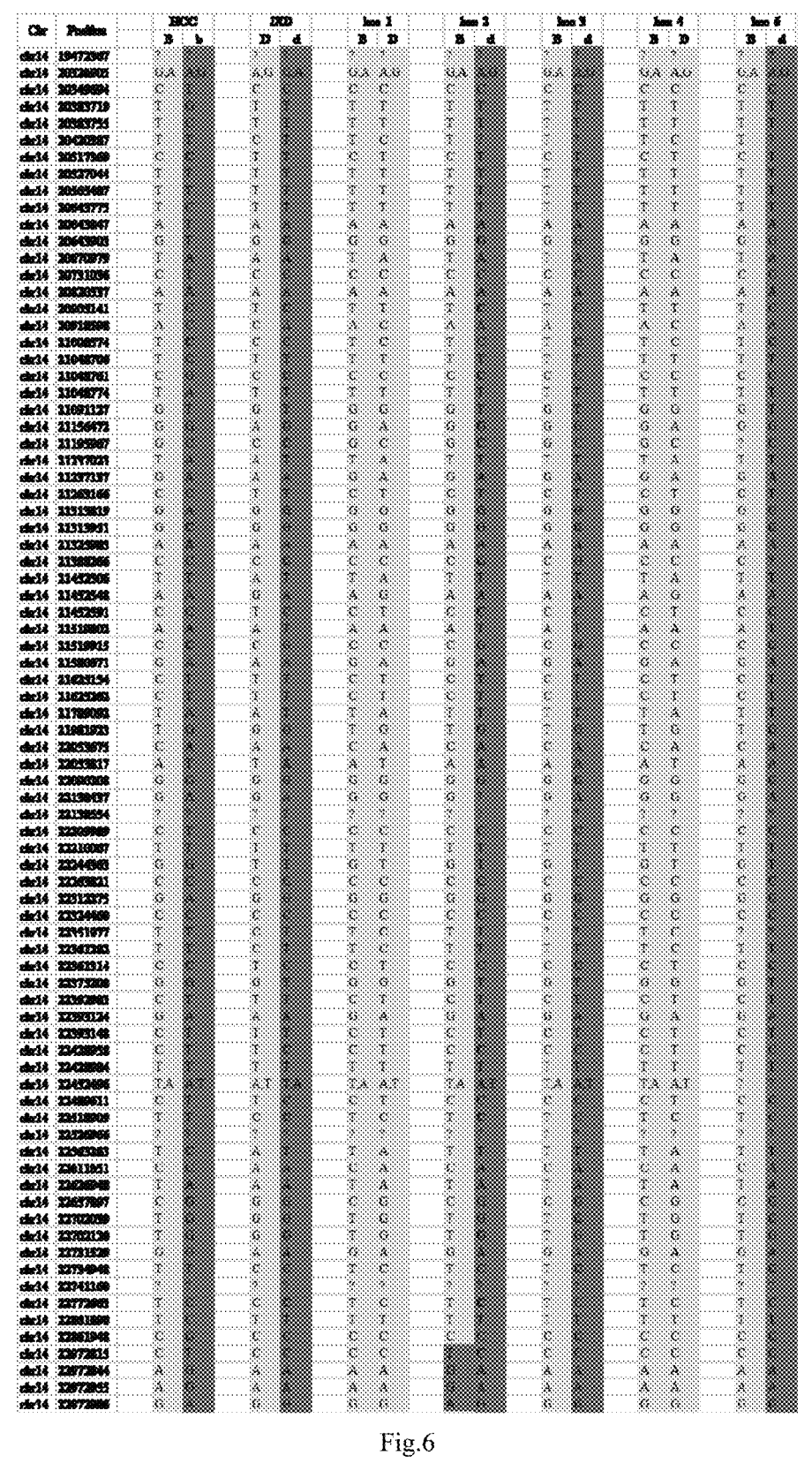

FIG. 6 shows chromosome pedigree haplotype pattern of Chromosome 14 pedigree haplotype in Example 2.

DETAILED DESCRIPTION

Figure 1:
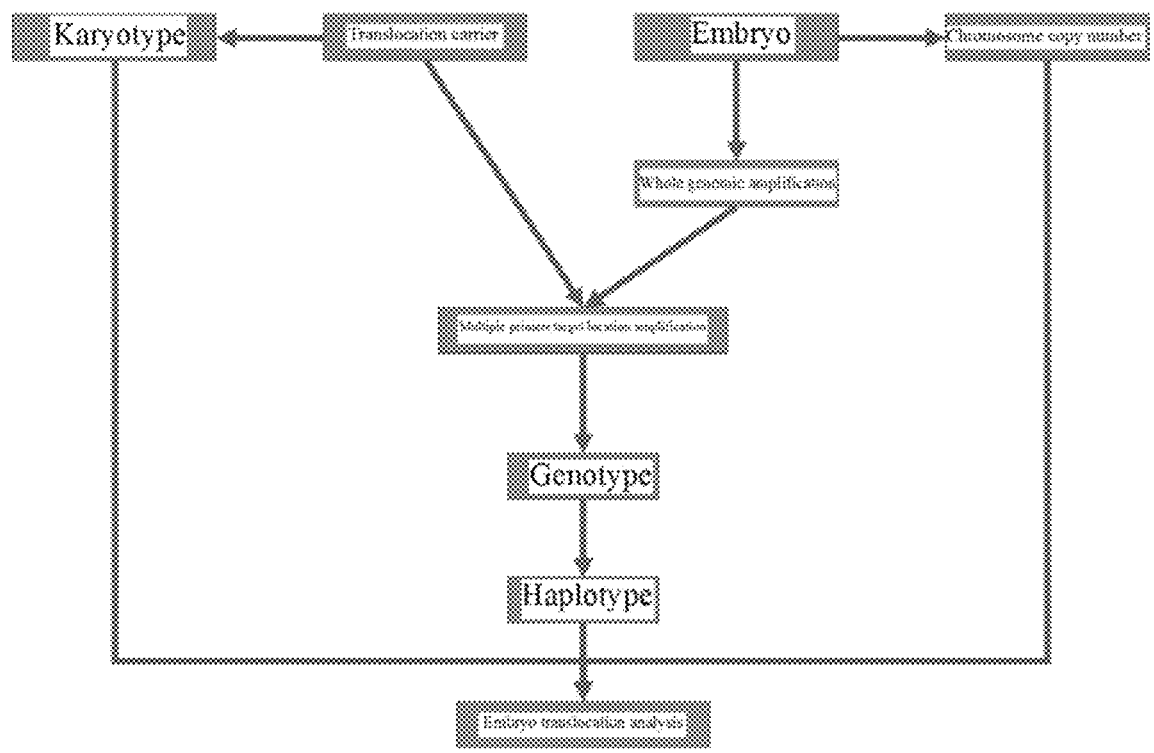
FIG. 1 shows the flow chart of the method for detecting chromosomal Robertsonian translocation according to the invention.
Figure 2:
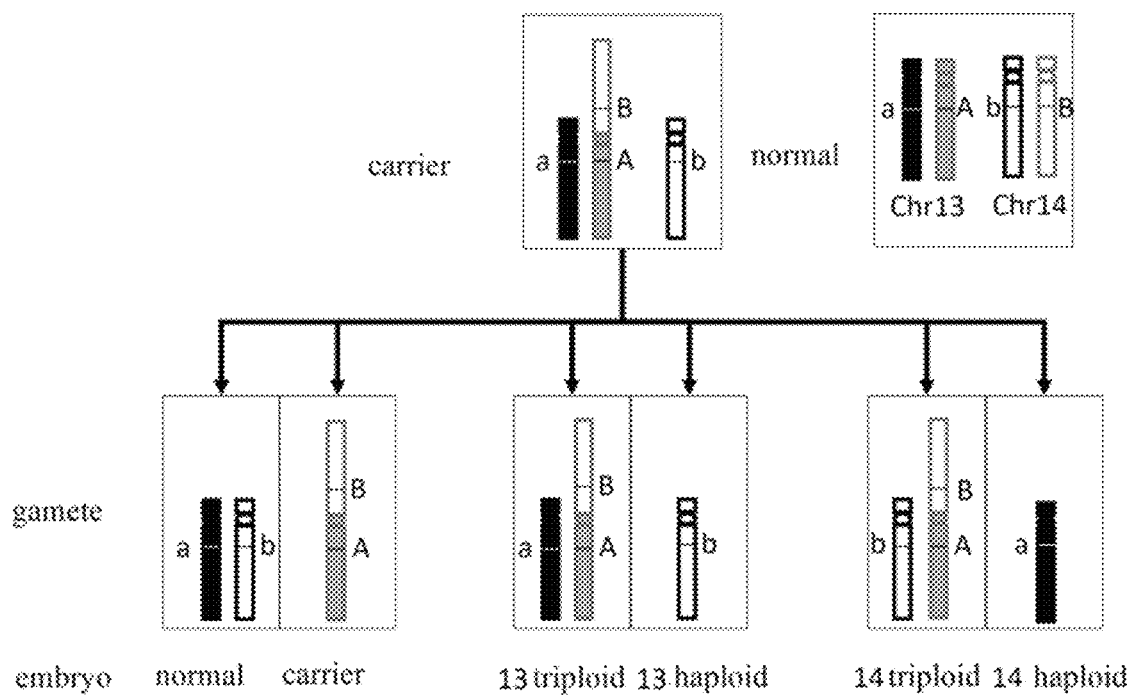
FIG. 2 shows the analysis chart of the method for detecting chromosomal Robertsonian translocation according to the invention for embryo translocation chromosome.

In context of the invention, reads refers to sequence fragments obtained in sequencing.

In context of the invention, single nucleotide polymorphism (SNP) refers to DNA sequence polymorphism resulted from single nucleotide variation at genomic level.

In context of the invention, haplotype refers to a combination of a group of single nucleotide polymorphism in a specific location of a chromosome which is associated with each other and are intended to inherit to progeny entirely. It is also known as haploid or haplotype.

In context of the invention, embryo genomic DNA is obtained by enriching genomic DNA in cells with whole genomic amplifying process, when an embryo develops to blastula stage where 3-5 periphery trophoblast cell are taken.

In context of the invention, enrichment of DNA molecule in target location is performed with multiplex PCR amplification. The specific principle and procedures can be found in the manufacture's instruction, where the DNA molecule is enriched into fragments with certain lengths and relatively concentrated. In a specific embodiment according to the invention, DNA fragments have the lengths of 125-275 bp.

In the present invention, according to hypermutational SNP sites in proximity to acrocentric location of human Chromosome 13, Chromosome 14, Chromosome 15, Chromosome 21 and Chromosome 22, 57, 58, 74, 75 and 80 pairs of sequence specific primers are designed respectively (primer sequences and relevant SNP site information can be found in Table 1-5). These primers are characterized in that (1) unique in target chromosome; (2) have the same annealing temperature.

In the present invention, SNP site is indicated with the chromosome where the site is located and the location at the chromosome (hg19 reference genome sequence as standard), for example, chr13:19602195 indicates that the SNP site is located at 19602195 nucleotide in Chromosome 13, hg19 reference genome sequence.

TABLE 1

Hypermutational SNP sites in proximity to acrocentric location of Chromosome 13 and detecting primers

| No. | chromosome: location | forward primer sequence (5'->3') | reverse primer sequence (5'->3') |
|---|---|---|---|
| 1 | chr13:19602195 | TTCCTCATGAACCTATTGATTATGTTTCAGAA (SEQ ID NO: 1) | TCTGACCGACAAATACCACAATCTC (SEQ ID NO: 2) |
| 2 | chr13:19625370 | TGTTCCAGGGATGGATGGTCT (SEQ ID NO: 3) | GGGTAGAAAACTGGCCAGATGATG (SEQ ID NO: 4) |
| 3 | chr13:19646283 | CCTCACAGGAGAGGTTGTTTGC (SEQ ID NO: 5) | GCCTGTTTTTGTCTCTGAAATAAGAACTC (SEQ ID NO: 6) |
| 4 | chr13:19692745 | GCAGTCCAGGAATCCTCCTGTA (SEQ ID NO: 7) | ATCCCAAAACTATTTTCCTTCTCCTATCAC (SEQ ID NO: 8) |
| 5 | chr13:19713634 | GTCTGGTTGGTTAGAATGTTCCATGA (SEQ ID NO: 9) | CACAGTGGAGCAGTTTAGACAGAG (SEQ ID NO: 10) |
| 6 | chr13:19722801 | AGTAACATGTTCCTTGTTTGCTCTGT (SEQ ID NO: 11) | CATGGCAGTGGTTTTGCAATTG (SEQ ID NO: 12) |
| 7 | chr13:19732341 | CATCATAGGGTTTGCCAGATGGT (SEQ ID NO: 13) | TGGCAGAGTTAATGAATCTGTGACAG (SEQ ID NO: 14) |
| 8 | chr13:19784913 | CAAAAGTGAGTGCTTGGAAAGCT (SEQ ID NO: 15) | TGCAATTCTATCAATGGCATACAATGTAAA (SEQ ID NO: 16) |
| 9 | chr13:19843135 | GAAGAAGGTGAGAGATTGCCTGA (SEQ ID NO: 17) | CAACAGAGTGAGTTGCGTTTCTTC (SEQ ID NO: 18) |
| 10 | chr13:19877547 | ACTCTACAGAGCATAGACTGCTCA (SEQ ID NO: 19) | TGTTAGTCATAGTGTTAGATCTCCATGTGA (SEQ ID NO: 20) |
| 11 | chr13:19883672 | GGAAGGTGGGATAATAAGGAAAACAGT (SEQ ID NO: 21) | CTGTATTAATGTGTGCACACTTTGCTTAG (SEQ ID NO: 22) |
| 12 | chr13:19896927 | GTTCATCATCATAAAAACACACTGAAGTGT (SEQ ID NO: 23) | GCCTCAGGTAATCCTTTATAGCAAGATAAG (SEQ ID NO: 24) |
| 13 | chr13:19917509 | TCATCAGGATCAGGTTCTAAAATCTTACAC (SEQ ID NO: 25) | GCATCAAGGTTTTAAGATTTCTAGGTTACG (SEQ ID NO: 26) |
| 14 | chr13:20494558 | CCTCTAGGACAGAGATGGACAAACT (SEQ ID NO: 27) | GATACAAAACTCTGCCTGCTTACAC (SEQ ID NO: 28) |
| 15 | chr13:20709214 | CCATTTTCTGTCTCTTGCTCTAGGTAT (SEQ ID NO: 29) | GGAAGATGGAAAACTTCTGGAAAAGGAT (SEQ ID NO: 30) |
| 16 | chr13:20747500 | CAGTATCAACAGAAAACAAGCTGATTCAA (SEQ ID NO: 31) | CTGCAACTATACCATTTTACATTTCCACT (SEQ ID NO: 32) |
| 17 | chr13:20784332 | CTGCCATCTGAATGGTTTCAAGG (SEQ ID NO: 33) | CTTTTTCTCCTGACTTTGTGGCAT (SEQ ID NO: 34) |
| 18 | chr13:20825315 | GTTATGTATTTGTGATGCATTGGCCTT (SEQ ID NO: 35) | CTTTAACTGAAGGCAAAAATTAGCAGACT (SEQ ID NO: 36) |

TABLE 1-continued

Hypermutational SNP sites in proximity to acrocentric location of Chromosome 13 and detecting primers

| No. | chromosome: location | forward primer sequence (5'->3') | reverse primer sequence (5'->3') |
|---|---|---|---|
| 19 | chr13:20864572 | CAGTTACTTAGAACAGCAA GATACTGAACA (SEQ ID NO: 37) | AAGTGCATGACTTAGAGCC ACAA (SEQ ID NO: 38) |
| 20 | chr13:20881859 | CCAAGTGAATGGTGGTCTCA CT (SEQ ID NO: 39) | ATCTCCAAACATCTGCCAA CACT (SEQ ID NO: 40) |
| 21 | chr13:20908501 | GTACACACACTGCATCTCGT ATGT (SEQ ID NO: 41) | GGCACCAGGATAGTCACTG TAG (SEQ ID NO: 42) |
| 22 | chr13:20938952 | GGTGTCTGTATCCACTCCAA TTCC (SEQ ID NO: 43) | GTGCTCTTGATCTAACTGG AGCTT (SEQ ID NO: 44) |
| 23 | chr13:20951425 | AAAGCAAAACAACCATGCA CCATTA (SEQ ID NO: 45) | GGGAAAAGCATCCCATCTT TCC (SEQ ID NO: 46) |
| 24 | chr13:20992333 | TCCTCAGGGAGATCTCAGTT CTG (SEQ ID NO: 47) | GTTAGATGTGTCTTGCTTC CTCTTCTC (SEQ ID NO: 48) |
| 25 | chr13:21012562 | CATCTACAGATCCGGTAGGA GTCT (SEQ ID NO: 49) | GGAGAATCGTGAGGGTTA CTCTGA (SEQ ID NO: 50) |
| 26 | chr13:21066214 | ACCAAATATGTGTCTTGGCC AGTT (SEQ ID NO: 51) | GAGTGCTGTTGATGCTGAA TCG (SEQ ID NO: 52) |
| 27 | chr13:21092894 | CAGAAGCAATGGAGGGATT TTGG (SEQ ID NO: 53) | GTACTGTGAAAATACTGCA CATTCATTTCT (SEQ ID NO: 54) |
| 28 | chr13:21112935 | GCCTGGTGACAGAGTATGAT GAC (SEQ ID NO: 55) | GAGGTCACAGCAATGTCA GGAA (SEQ ID NO: 56) |
| 29 | chr13:21527671 | GCACCAAACAAGGACACAT AGTG (SEQ ID NO: 57) | TTTTTCCTTAATCTACCCAA ATACCAGGTA (SEQ ID NO: 58) |
| 30 | chr13:21553971 | AATGCTGACCAAAGATTCAT GGGTA (SEQ ID NO: 59) | AGGAAATCTGTATGTTCAG CATCTTAATGA (SEQ ID NO: 60) |
| 31 | chr13:21575458 | TTTTGTCACAATGGAGATAG GTGAACA (SEQ ID NO: 61) | CTCATTCCATTGATAGAGA AAATCACAGG (SEQ ID NO: 62) |
| 32 | chr13:21607760 | GTGACCTCAGACAGAGAGG TAGA (SEQ ID NO: 63) | AAGTGTAGTGGAACAAATT GTACTCTGT (SEQ ID NO: 64) |
| 33 | chr13:21636136 | GCCTCTCGGACCTATTTGAC TG (SEQ ID NO: 65) | GCTTCTGGCAAACGTCCTT CTTAAT (SEQ ID NO: 66) |
| 34 | chr13:21655335 | TTTGAAGACAAATTACCACT TAAGGTTGTG (SEQ ID NO: 67) | GTGATGATGAAGCCTTTCC CTTCA (SEQ ID NO: 68) |
| 35 | chr13:21683681 | GTGTCTGTTTTCTGAGTCCT TCTTGT (SEQ ID NO: 69) | CTCAGACTAGATAAAGGCT GGTAGAAAC (SEQ ID NO: 70) |
| 36 | chr13:21801501 | CTCAGAATCTCTTGGCTGTG ACA (SEQ ID NO: 71) | TGAAGCCATGCTGATAGCA TGT (SEQ ID NO: 72) |

TABLE 1-continued

Hypermutational SNP sites in proximity to acrocentric location of Chromosome 13 and detecting primers

| No. | chromosome: location | forward primer sequence (5'->3') | reverse primer sequence (5'->3') |
|---|---|---|---|
| 37 | chr13:22197910 | GGCAGCCATTGAACTGGAA AAA (SEQ ID NO: 73) | CAACATGGAAACCTCTCAC ATTCAG (SEQ ID NO: 74) |
| 38 | chr13:22249975 | TCCTCACACTCAGTTTCTCT AGAAAAGA (SEQ ID NO: 75) | TCCCACCTAAGTTGTCACC TCT (SEQ ID NO: 76) |
| 39 | chr13:22270788 | GTATAGTTTATTTGAAGGCA GACACTCCTT (SEQ ID NO: 77) | GCCAATGTGTGATTTTGT TTTAGACG (SEQ ID NO: 78) |
| 40 | chr13:22340074 | ATCAGTGAGTGCTTAAACTA TTGGATCAA (SEQ ID NO: 79) | GAATTAGATTCAGGCTATG CATTTCAGG (SEQ ID NO: 80) |
| 41 | chr13:22396664 | TACCAAACATAGCGTGGACC TTTT (SEQ ID NO: 81) | GAATGGCAACGGAGTTGTT TCC (SEQ ID NO: 82) |
| 42 | chr13:22417688 | ACAGATTTTATTCGAATATCC GGTTGGAT (SEQ ID NO: 83) | CATTTGCCAGGATTTCTGC TCA (SEQ ID NO: 84) |
| 43 | chr13:22473749 | GTAGGGCTCAGTGCTTTCTG TT (SEQ ID NO: 85) | GCATCCTCTGTTTGAGCTA AGGT (SEQ ID NO: 86) |
| 44 | chr13:22504691 | CATTTATTTAACAAGGGACA CAGACCAAA (SEQ ID NO: 87) | TAACTCCGCAGTCCTTAGA CCA (SEQ ID NO: 88) |
| 45 | chr13:22515844 | ACCATGGCATGGTCACTAAA AACT (SEQ ID NO: 89) | GGGTCGCTCTGGTGTATAA GC (SEQ ID NO: 90) |
| 46 | chr13:22523279 | TTTGCAAAGACTTCCTGCTG AATG (SEQ ID NO: 91) | CCTCCAAAAATAGTCAGTA GTTCCTACAAT (SEQ ID NO: 92) |
| 47 | chr13:22538311 | CCTTGGACTTTTAGCTTCTA GAACTGTA (SEQ ID NO: 93) | ATTGCCTGATATACCGCAG TTTATTTATCT (SEQ ID NO: 94) |
| 48 | chr13:22561684 | CCCAAAAATCTAAAGCCATC ACCTT (SEQ ID NO: 95) | ACATCATATGACGTAAAAA TTCCTACAGCA (SEQ ID NO: 96) |
| 49 | chr13:22640820 | CACCAGCATTAGTTTAGGCA AACA (SEQ ID NO: 97) | TAACGAAACTGTGCACTTG TTCCT (SEQ ID NO: 98) |
| 50 | chr13:22751654 | TTAAAGAGGTAGAATCTGTA GGACTTGGT (SEQ ID NO: 99) | TGGATGTTGGTTCCCTACC TCT (SEQ ID NO: 100) |
| 51 | chr13:22768476 | TTCTGTGTTGCAAGTGACAG AAAAC (SEQ ID NO: 101) | TTGCTGCTGACAACAAAGA TGTTTT (SEQ ID NO: 102) |
| 52 | chr13:22780737 | ACAGTAGGTTAAACAGGATA GGAAAACG (SEQ ID NO: 103) | TGAGATTTAAGTGCAAATG GATGCAAC (SEQ ID NO: 104) |
| 53 | chr13:22799808 | GAAAACTGGTCAGAGGCAG CTAA (SEQ ID NO: 105) | AGAGGATGATTCCCTATAC CTCTGAGTA (SEQ ID NO: 106) |
| 54 | chr13:22819627 | GAATGTAGGGACCAAATTCC ATAGACA (SEQ ID NO: 107) | ACAGACAGACAGACAGAT AGTATATGTGT (SEQ ID NO: 108) |

TABLE 1-continued

Hypermutational SNP sites in proximity to acrocentric location of Chromosome 13 and detecting primers

| No. | chromosome: location | forward primer sequence (5'->3') | reverse primer sequence (5'->3') |
|---|---|---|---|
| 55 | chr13:22835073 | CTTAATGCAGATGAGGAACTAATGCAC (SEQ ID NO: 109) | TCATGAAACCACTGTTTGGATAATCATCAT (SEQ ID NO: 110) |
| 56 | chr13:22892864 | GCTTAATGCAGTGGGTCCTAAACT (SEQ ID NO: 111) | CACTGTAACACTTTAAATGGGTGAATTGTT (SEQ ID NO: 112) |
| 57 | chr13:22980146 | CTCAGTTGCAGAGCCACAGACT (SEQ ID NO: 113) | GGTGTGCCAGAATCTAAGAGAAATTCTC (SEQ ID NO: 114) |

TABLE 2

Hypermutational SNP sites in proximity to acrocentric location of Chromosome 14 and detecting primers

| No. | chromosome: location | forward primer sequence (5'->3') | reverse primer sequence (5'->3') |
|---|---|---|---|
| 1 | chr14:19472367 | TGATTTGATGTTCTAACCAGCACTAAAACT (SEQ ID NO: 115) | GCCCTATACATGTTCAGGTGGAAAG (SEQ ID NO: 116) |
| 2 | chr14:20326905 | GGGCCTTTCCCAAATGCTAT (SEQ ID NO: 117) | GGGATATAAAGGTATTCAATAAAGGATAGCAT (SEQ ID NO: 118) |
| 3 | chr14:20349694 | TCTTGGTTACACCATGAGGTAAATATGC (SEQ ID NO: 119) | TAGGTATTCATCTCCTTATATTGGCAGTGT (SEQ ID NO: 120) |
| 4 | chr14:20383719 | GTCATTCTTTTTGCATTAGCTGGTTGA (SEQ ID NO: 121) | ATGCCAAAAGTACTTTGTCCATAAATGTG (SEQ ID NO: 122) |
| 5 | chr14:20420387 | CTTTTCATGTCTGACATCTGTACCACT (SEQ ID NO: 123) | TGCCTAAGGTAATGATAAACCGAATGTG (SEQ ID NO: 124) |
| 6 | chr14:20517369 | CAGGACTGGGAGAGAAATAGGAGA (SEQ ID NO: 125) | GATATTTGCATCAGAATCAGATGCTTTTGT (SEQ ID NO: 126) |
| 7 | chr14:20527044 | GCTATGGGTTTTGACAAATGTGTTATGT (SEQ ID NO: 127) | ATAGCTTTGCAATAGCCTCTAAGTGTT (SEQ ID NO: 128) |
| 8 | chr14:20565487 | GTTGTTGTTGTTTGTTGGTTTAGATTACCA (SEQ ID NO: 129) | ACTTGAAAAGAGGCTAATGTTAGTGAACT (SEQ ID NO: 130) |
| 9 | chr14:20643775 | CGTGTTCACATTGCCCTCTACA (SEQ ID NO: 131) | AAACACCTCAAGGCAGAATGACT (SEQ ID NO: 132) |
| 10 | chr14:20670979 | GCTTCGATCTACCATCTMCTGT (SEQ ID NO: 133) | AGACCATTAGAGCACCAGCTTTTT (SEQ ID NO: 134) |
| 11 | chr14:20731036 | CTGCCATGGTTGATTAGCAGGA (SEQ ID NO: 135) | GAGATCTATTCGCTTGAGATAGGAAGTG (SEQ ID NO: 136) |
| 12 | chr14:20820537 | TCTTTGGAGATTTTCTGTCTTGTAAGTCC (SEQ ID NO: 137) | AACAGAGCACAGTTTTGCCTCTA (SEQ ID NO: 138) |

TABLE 2-continued

Hypermutational SNP sites in proximity to acrocentric location of Chromosome 14 and detecting primers

| No. | chromosome: location | forward primer sequence (5'->3') | reverse primer sequence (5'->3') |
|---|---|---|---|
| 13 | chr14:20905141 | TGGGACCCAGGAGCGAATATAG (SEQ ID NO: 139) | TCCTCACAGCATGCAGATCAAG (SEQ ID NO: 140) |
| 14 | chr14:20918598 | TTTGTATTAAGGCCGTTCTTCATATGTGA (SEQ ID NO: 141) | GTAAGAAACAGGGAGGGTGATTAGG (SEQ ID NO: 142) |
| 15 | chr14:21008574 | CTGATGTTATCAGGCTATTGCAGAAC (SEQ ID NO: 143) | CAGGTCACAAGAAAGCTTTGTGAG (SEQ ID NO: 144) |
| 16 | chr14:21048774 | GGAAACATGAGTTCCTCTTACAGTGA (SEQ ID NO: 145) | GCAAAGTTTGAACTCTACTGGATTAGATGA (SEQ ID NO: 146) |
| 17 | chr14:21091127 | TGGGTACCCAGTGAGCTTAGAT (SEQ ID NO: 147) | CTCAGGGAGCACCGCATAAACG (SEQ ID NO: 148) |
| 18 | chr14:21156472 | ATGGAAGAAGGAGAAACCCAGGAAACATG (SEQ ID NO: 149) | GTCACAGAGTAAGATATGGTCTTCCAGTA (SEQ ID NO: 150) |
| 19 | chr14:21195967 | GCGTTGTGTGAGAATAGAGGAACA (SEQ ID NO: 151) | CAAATGTCCTTTTCGGATTCAATCAGG (SEQ ID NO: 152) |
| 20 | chr14:21237137 | ACATTTGACATCATTAGAAGTGCTCTCA (SEQ ID NO: 153) | GTAATCAATCAAGCACCAAGACTAAAAGAG (SEQ ID NO: 154) |
| 21 | chr14:21263166 | CCTTTATGCAAGATGGTGGTTTTTGA (SEQ ID NO: 155) | GTTTGGTGGCACAGCTGTAATC (SEQ ID NO: 156) |
| 22 | chr14:21313819 | ATCCCTTGTAGCAACATAAATGGATTGA (SEQ ID NO: 157) | CAGAACAATGGCAGTATTTCTGAAGC (SEQ ID NO: 158) |
| 23 | chr14:21325985 | CCACGCCCTCAAGAATGAAACA (SEQ ID NO: 159) | CAAGCACGAGTTGAGGAGTAGTC (SEQ ID NO: 160) |
| 24 | chr14:21388266 | AGTCCAGGTGCCTTTAATGTACTG (SEQ ID NO: 161) | ATGCTGACACCCAGAGTACATG (SEQ ID NO: 162) |
| 25 | chr14:21452591 | GCTGCTAAGAAATATCTTCTTCCAGACT (SEQ ID NO: 163) | GGCCCTTAAATATGAGTTGATGGTACATTT (SEQ ID NO: 164) |
| 26 | chr14:21519915 | GATGAATCCAGGAGTGAGGAACAA (SEQ ID NO: 165) | AGCTTCAACCTTCAAACAGCCT (SEQ ID NO: 166) |
| 27 | chr14:21580671 | CAAAACAAAACCCATTCGATCCAGA (SEQ ID NO: 167) | TACTTGCAACAAAGAAGGAGAATACTGG (SEQ ID NO: 168) |
| 28 | chr14:21625262 | AGTGAGTCTTTGTGAAAATGCCTTTTC (SEQ ID NO: 169) | GTGTGTTATTCGCTTACTCTCCTCA (SEQ ID NO: 170) |
| 29 | chr14:21789092 | TGCTTGAGGACACTTTTTGGAAAAC (SEQ ID NO: 171) | GTAAAATGCCAGCAGCAGAAACTAC (SEQ ID NO: 172) |

TABLE 2-continued

Hypermutational SNP sites in proximity to acrocentric location of Chromosome 14 and detecting primers

| No. | chromosome: location | forward primer sequence (5'->3') | reverse primer sequence (5'->3') |
|---|---|---|---|
| 30 | chr14:21981923 | TTGTAGAAGGTACATGGTACCTGAGT (SEQ ID NO: 173) | CACATACATCTTTCAATAGCTCCCTTCATA (SEQ ID NO: 174) |
| 31 | chr14:22053817 | TCAATAGCTTCTGGCTTCAATCTACTG (SEQ ID NO: 175) | CATGAGAGATTCTTGGGACCTGAAA (SEQ ID NO: 176) |
| 32 | chr14:22090208 | GGGAGCTTTCCTTCTCTATGTTTCC (SEQ ID NO: 177) | GATGCTTCCATGTGGTCACAAAAG (SEQ ID NO: 178) |
| 33 | chr14:22138437 | GCGGGAATAGATGAAGATGCAGT (SEQ ID NO: 179) | GGTCCTGATGAGATTGACAACTTCTTC (SEQ ID NO: 180) |
| 34 | chr14:22210067 | ATGAAACCATTAGCTCATCAGGAATTAGTT (SEQ ID NO: 181) | CACACTGCTAATAAATTCAAAATGGCAAAA (SEQ ID NO: 182) |
| 35 | chr14:22244363 | CATGAGATACACTACATACTCACCCAA (SEQ ID NO: 183) | CCCTAGCCACTTCTTGTCTGTG (SEQ ID NO: 184) |
| 36 | chr14:22263821 | TCTTATAAGTGAGAGACAATCTACAGGCAA (SEQ ID NO: 185) | CCTGTTCTTCTGAAAGAGGCCTTTT (SEQ ID NO: 186) |
| 37 | chr14:22312275 | GGGCAAATGTGAGCCAAGAGTA (SEQ ID NO: 187) | ACTTAGATGGTTTCTGTTAACAAGTGCT (SEQ ID NO: 188) |
| 38 | chr14:22324460 | TGTGCACACCATTGGCTGATTA (SEQ ID NO: 189) | CACAAGGACACAAAGATGAGAACAATAAG (SEQ ID NO: 190) |
| 39 | chr14:22351977 | GTACAATAATTCCTAGAGCAGAACACTCA (SEQ ID NO: 191) | CCAGAATCATTAGCTGTATGTAACGAGATG (SEQ ID NO: 192) |
| 40 | chr14:22361282 | TTTGAATCAGAAGCACATCCTAGTAACATT (SEQ ID NO: 193) | GCATAGAGATCATTGGACCCTAAAACTTAA (SEQ ID NO: 194) |
| 41 | chr14:22375208 | TTAGTGTAAAGGTAACAGAATTTTCAGGCT (SEQ ID NO: 195) | TCATGATCACAGCTCAGTGTAACTTT (SEQ ID NO: 196) |
| 42 | chr14:22393124 | GCGGGAAATCAACATCACAGAC (SEQ ID NO: 197) | CAGTCACATGTTTTTGAATCCAGTTCAAT (SEQ ID NO: 198) |
| 43 | chr14:22428984 | CCTTTAGTGAGGATTTGTCAGGTCTT (SEQ ID NO: 199) | TGAACTTCCTAAGCTCAGAGTTCCT (SEQ ID NO: 200) |
| 44 | chr14:22452496 | CCTATTAGTGAGCTATTGAATTTGGTTTGC (SEQ ID NO: 201) | ACCTCCTAACAAAGAAGACAAAAGACC (SEQ ID NO: 202) |
| 45 | chr14:22489611 | CCTAGGCTCCAATATTGAAAAGTTTCAAAG (SEQ ID NO: 203) | TAGTCCTGTGGTTAGCTTCCAGAA (SEQ ID NO: 204) |
| 46 | chr14:22518909 | AGGAAAGAGGTTTCATTGGCTGTT (SEQ ID NO: 205) | GGGTAAATTTTCCCTTTGGTGCT (SEQ ID NO: 206) |
| 47 | chr14:22526966 | TCAGAGAAGGCCTCTCTGAGAAAATA (SEQ ID NO: 207) | CCTTTCCCTTGAACAGTTAGAAGTCAC (SEQ ID NO: 208) |

TABLE 2-continued

Hypermutational SNP sites in proximity to acrocentric location of Chromosome 14 and detecting primers

| No. | chromosome: location | forward primer sequence (5'->3') | reverse primer sequence (5'->3') |
|---|---|---|---|
| 48 | chr14:22563283 | GCAACTGGAGTCCTAGCCAT TTG (SEQ ID NO: 209) | AAGAACTTTGTGCATGTCA ATACCAC (SEQ ID NO: 210) |
| 49 | chr14:22611651 | GTGGCTGATGAGGCTGATGT AT (SEQ ID NO: 211) | GGCTAGGTCACATCAAACA ATTTACTTAAC (SEQ ID NO: 212) |
| 50 | chr14:22626948 | ATTCACAGGTTATCAAAGGA GAAGTATGAC (SEQ ID NO: 213) | GTTCCCTGCTTAATCCAGT ACAAAC (SEQ ID NO: 214) |
| 51 | chr14:22657897 | AGAAAACACCAAGACAAAA CAGAGATTTG (SEQ ID NO: 215) | GCCCATAGGTACTGAAGCC AAAG (SEQ ID NO: 216) |
| 52 | chr14:22702039 | ATGCCTTTGAACTGTTTGAA ACTGAAT (SEQ ID NO: 217) | ATTCATTCGATATTAGTGTG AGCATATGGT (SEQ ID NO: 218) |
| 53 | chr14:22731529 | TCAACACAATCTTAGATAGC AGTAGTGGTA (SEQ ID NO: 219) | GTAGCTTAATAACTGATAC AAGAGCCAAGA (SEQ ID NO: 220) |
| 54 | chr14:22734948 | TCCTGCTCTTTTCTAGGGTC AGA (SEQ ID NO: 221) | CAGCTAATCTATTCATGGGT CTATTGTTCA (SEQ ID NO: 222) |
| 55 | chr14:22741160 | CCTAGGTCCACTGCAGTAGA AC (SEQ ID NO: 223) | TCTAATCTAGCAGAACCTA GGGTTGT (SEQ ID NO: 224) |
| 56 | chr14:22772663 | TCCTCCTGCAGGAACTATGA CT (SEQ ID NO: 225) | GAATTATTTGTGACAGTTG CACTACATGTA (SEQ ID NO: 226) |
| 57 | chr14:22861948 | AACCTGGTGCTCAACTGTCT TATTAG (SEQ ID NO: 227) | TTGAGCACTCTTCTTCTGT TGAGAAAA (SEQ ID NO: 228) |
| 58 | chr14:22972955 | GCAACACAGGCAAACTAAT CTTTGG (SEQ ID NO: 229) | AATTCCAGATCCAATACAC CCTTCTTTT (SEQ ID NO: 230) |

TABLE 3

Hypermutational SNP sites in proximity to acrocentric location of Chromosome 15 and detecting primers

| No. | chromosome: location | forward primer sequence (5'->3') | reverse primer sequence (5'->3') |
|---|---|---|---|
| 1 | chr15:20022190 | GAAGATATTTCTTTCCAC ATTGTCCTCA (SEQ ID NO: 231) | AAGGAAGCCACTCAACTG CA (SEQ ID NO: 232) |
| 2 | chr15:20049922 | CGATGTCGCCTCTGTTCTG A (SEQ ID NO: 233) | AAATACAATGCAAACTTG TATTATCTCCATATG (SEQ ID NO: 234) |
| 3 | chr15:20189367 | TGGAGGTCTAATATATGGC AATGTTCCT (SEQ ID NO: 235) | CCCACATTCAGGATTGAG GATTATAATACA (SEQ ID NO: 236) |
| 4 | chr15:20191854 | ATAAAGAGACATCAGCATT CCGTATCAG (SEQ ID NO: 237) | GTTGTTGTACCAAATAAA CACAAAAACACT (SEQ ID NO: 238) |
| 5 | chr15:20192138 | GAGGCCTAATCCAAGGAG AGAGAT (SEQ ID NO: 239) | GCTTTGCAGGCCATAAATA TATACAACAAA (SEQ ID NO: 240) |

TABLE 3-continued

Hypermutational SNP sites in proximity to acrocentric location of Chromosome 15 and detecting primers

| No. | chromosome: location | forward primer sequence (5'->3') | reverse primer sequence (5'->3') |
|---|---|---|---|
| 6 | chr15:20454253 | TCACAAGGCATTTGGGATC CTC (SEQ ID NO: 241) | ACAGAGTGAGACCACACT CCA (SEQ ID NO: 242) |
| 7 | chr15:20470948 | AAAAATCCTAACTGAAAC CCACTGT (SEQ ID NO: 243) | TTTATAAACATGCTGTTGT GTTGCAAAAA (SEQ ID NO: 244) |
| 8 | chr15:20564500 | GGGAGGGTAATCACACCA ATAGAG (SEQ ID NO: 245) | CTTCCATCTAAAGAAACA CCAATTTAGGAG (SEQ ID NO: 246) |
| 9 | chr15:20569241 | CTCTCTTTGGCCACATGAC CAT (SEQ ID NO: 247) | TACCTTGTGTGCTAAGCTG TTCTTATG (SEQ ID NO: 248) |
| 10 | chr15:20586537 | GAGTGGTGTGACTGTGGT GAAT (SEQ ID NO: 249) | CACTGACCTTCATAGGAG ACAACTG (SEQ ID NO: 250) |
| 11 | chr15:20586966 | TTGTGTCACAAACAAGAA GTCTTTTATTAAAT (SEQ ID NO: 251) | AATTAAACATATCACAAAC ATGCTTGGAATCTT (SEQ ID NO: 252) |
| 12 | chr15:20590656 | CAGAATCTGTAAACATGCT AGTTTGCAT (SEQ ID NO: 253) | GTCTTTTGCAGCTCCTAG AAGGT (SEQ ID NO: 254) |
| 13 | chr15:20616721 | AGGAGCATGCCATCAGGA AAAA (SEQ ID NO: 255) | CGAAAGGATTATGGAAGT GTCATGGTTA (SEQ ID NO: 256) |
| 14 | chr15:20626721 | GTTATGGCAGGACCATCTT TCCA (SEQ ID NO: 257) | AGCACACATTCTAAAGGA AATCACTCAA (SEQ ID NO: 258) |
| 15 | chr15:20646773 | CAGGACTCCACTACTCCCT GAA (SEQ ID NO: 259) | CCCATGAGTGTGTCTGAAT AACTTAGTATC (SEQ ID NO: 260) |
| 16 | chr15:20848359 | TATGGTAAGAATGTGGGTG ATGATTGAC (SEQ ID NO: 261) | AGAACTGAGTCCATCCCT GTAGTAC (SEQ ID NO: 262) |
| 17 | chr15:20849625 | CCTTCCTGTCTGACTCCTA AGCA (SEQ ID NO: 263) | ACTATGTTGAGATTTGACT GAATTTGCCT (SEQ ID NO: 264) |
| 18 | chr15:20852181 | CACAATTGACGGTCGCAA GTAC (SEQ ID NO: 265) | CAGCACTGGCTCCTACCT AAAA (SEQ ID NO: 266) |
| 19 | chr15:20862156 | GGCTACAATCCTTTAACTT TCTCCAATCAA (SEQ ID NO: 267) | TTTTGGTACCAAACAATG ATTAAGGGAGA (SEQ ID NO: 268) |
| 20 | chr15:20863958 | TAGAACAGCAACGTTTTG TTTCTGC (SEQ ID NO: 269) | CGCCCTACTTTTATGTAGT ACTTGAAGT (SEQ ID NO: 270) |
| 21 | chr15:21905797 | CAACCACAGCGAAACAGT GTC (SEQ ID NO: 271) | TCTTCTGTGTCTAGAGGA AGAGCTAC (SEQ ID NO: 272) |
| 22 | chr15:21928397 | GGTTTGATCAGGTGTGAA GTTTACAG (SEQ ID NO: 273) | GAAGTTGTGCCAATAGGA AAATACTACCT (SEQ ID NO: 274) |
| 23 | chr15:21938184 | CTTCCTTTCTCTGTGCCTG AGAA (SEQ ID NO: 275) | TCCCAGGAGCTCTGACCA A (SEQ ID NO: 276) |

TABLE 3-continued

Hypermutational SNP sites in proximity to acrocentric location of Chromosome 15 and detecting primers

| No. | chromosome: location | forward primer sequence (5'->3') | reverse primer sequence (5'->3') |
|---|---|---|---|
| 24 | chr15:21940649 | CCAGTATAAAAAGGAACACTTTACAGGGT (SEQ ID NO: 277) | CACAGTGAAAGTAAAACTAGGAAAATCTGC (SEQ ID NO: 278) |
| 25 | chr15:22013203 | GCGGCACCTGAGAATCCATG (SEQ ID NO: 279) | GGTGAGGCTCCTTCAGTAGCT (SEQ ID NO: 280) |
| 26 | chr15:22299435 | AGGTAAACTTCCTCCTACATTCTTCTAAAA (SEQ ID NO: 281) | TCTCAAAATGCAAGCCCTCTTGA (SEQ ID NO: 282) |
| 27 | chr15:22302182 | GGGCTGAACTTTAAGCTCTATTCACT (SEQ ID NO: 283) | GTTTCAGTCAGTGTGAATGAGACAGT (SEQ ID NO: 284) |
| 28 | chr15:22376163 | AACCAAGAATTTATTTTCATGCTTGCT (SEQ ID NO: 285) | CTCAGAATTTTTAATGGCATTACCATAAGGTT (SEQ ID NO: 286) |
| 29 | chr15:22427155 | GGTGTCTTTCTTGGGTCAAGGT (SEQ ID NO: 287) | TGAAAATCAGCAGAGGTCATTGCT (SEQ ID NO: 288) |
| 30 | chr15:22441959 | CATGGTGAACACAAGCTTGCTA (SEQ ID NO: 289) | TTCAGTGCCGACAGCCAAGAGA (SEQ ID NO: 290) |
| 31 | chr15:22476195 | CACTCACATCCTGGTGTCTTGT (SEQ ID NO: 291) | GCTGTGAATGCAATCTTGGTAATCTG (SEQ ID NO: 292) |
| 32 | chr15:22520388 | CTTAGGAGTGAGCATGGTCCTT (SEQ ID NO: 293) | TACAATTAGGGTTAGTGTTAGGGTTAGGAT (SEQ ID NO: 294) |
| 33 | chr15:22539952 | ACATAGCACATGTGTGTGGCAT (SEQ ID NO: 295) | GATGCATTACATGTTCCTTATGAACAGC (SEQ ID NO: 296) |
| 34 | chr15:22780065 | GTGTAGGTTGGTTGGACAGGAA (SEQ ID NO: 297) | TTCACTTCTCACGTGAGGATCAAAG (SEQ ID NO: 298) |
| 35 | chr15:22798800 | GCTTTATCAATCACCCGTACAGTGA (SEQ ID NO: 299) | TAGAGCTCACAACCTATGATTTAACGC (SEQ ID NO: 300) |
| 36 | chr15:22833272 | CATGGATGTGTGTAGCGTGACT (SEQ ID NO: 301) | CCCGACGGTACGTTTTCTACTG (SEQ ID NO: 302) |
| 37 | chr15:22854479 | GTAGAGCTATTTGTACTCTTTTAGCCCA (SEQ ID NO: 303) | CATATTGCTACCCTTCCAGAACACTAA (SEQ ID NO: 304) |
| 38 | chr15:22869870 | GTCCTAGTTTCATTGGTGAATTTAAATGGC (SEQ ID NO: 305) | CAGAACACAAACTGTGTAACTAGGTTTG (SEQ ID NO: 306) |
| 39 | chr15:22893990 | CAGCGGTTTTCCAAGTGATGTC (SEQ ID NO: 307) | GACACCTGTCTTAACGCAGGAA (SEQ ID NO: 308) |
| 40 | chr15:22905599 | ACTGGTCACATGGAATTGACTGT (SEQ ID NO: 309) | GGCCGACATATGTGAAGAGGAA (SEQ ID NO: 310) |
| 41 | chr15:22916637 | CCCTGACTTGTTTGACTCCTTTG (SEQ ID NO: 311) | AGCAGCCAAGACTAACTTTAACCTG (SEQ ID NO: 312) |

TABLE 3-continued

Hypermutational SNP sites in proximity to acrocentric location of Chromosome 15 and detecting primers

| No. | chromosome: location | forward primer sequence (5'->3') | reverse primer sequence (5'->3') |
|---|---|---|---|
| 42 | chr15:22923869 | GGCCAGCATGCTCTTTGTT TTC (SEQ ID NO: 313) | ATGACGCTCAGCAGAGCA CAGA (SEQ ID NO: 314) |
| 43 | chr15:22940961 | GCTTTCTCTCTGCACAGAT GGA (SEQ ID NO: 315) | GAACCTGTCCCTGTCATTA TGTGA (SEQ ID NO: 316) |
| 44 | chr15:22971662 | GGTGGTCTGCGACTGGAA TTTA (SEQ ID NO: 317) | AGAAAAATGGTAACATGA CAGTGGGAA (SEQ ID NO: 318) |
| 45 | chr15:23000363 | GGCTGGCTGTATGATCATC GTA (SEQ ID NO: 319) | GATTCATTTTGGGAACGA AAAGAAAGTTT (SEQ ID NO: 320) |
| 46 | chr15:23010627 | CAGGAGGCCCACAAAGAA TTCTA (SEQ ID NO: 321) | TGCTCTTTGTGAGATTCTT ATTCATCTGTT (SEQ ID NO: 322) |
| 47 | chr15:23020535 | AGCCAGGATAGAATGATG GAATGTG (SEQ ID NO: 323) | GGCTGGGATCTTTTGTCCA TGAT (SEQ ID NO: 324) |
| 48 | chr15:23044004 | TGCTTGGAAGCAGGAAGT TCAG (SEQ ID NO: 325) | GGTGTAAAGTTTGCATGA TTCCATGAA (SEQ ID NO: 326) |
| 49 | chr15:23053813 | ACATCTATAATCTCCAGGC TTCTAACTTGT (SEQ ID NO: 327) | CCTTAGGTTCAATGCTGA CCCTT (SEQ ID NO: 328) |
| 50 | chr15:23064687 | TACTGAGTCACCTCCATGG GTT (SEQ ID NO: 329) | ATACACTGAGAGGGACAC CAGACA (SEQ ID NO: 330) |
| 51 | chr15:23721906 | CGTCTAACCTGCAAAATG CTAATATCTG (SEQ ID NO: 331) | GCCGATGTTAATCTTTTTA CATCTCTCTC (SEQ ID NO: 332) |
| 52 | chr15:23730971 | CAATAACTGCACAAAGAA GAGAGAAAATGG (SEQ ID NO: 333) | ACCATATTGCTGCTTTCTG TAATTTTCATG (SEQ ID NO: 334) |
| 53 | chr15:23746510 | TGCCCTAATAAACAGACTC CAGAGA (SEQ ID NO: 335) | CATTCAGGCTGCCATAAC AAAATAGTAAAG (SEQ ID NO: 336) |
| 54 | chr15:23767135 | GCCTATTTCTCCAAATTCT TTCAGCCT (SEQ ID NO: 337) | ACCTTTCTTTATGTTATGAT TCAGCCAGAA (SEQ ID NO: 338) |
| 55 | chr15:23781336 | CAAACCTGGAAAGGAGTT CTCTTGA (SEQ ID NO: 339) | GAATAAATCAGCTCAATA GGCTGAATTGC (SEQ ID NO: 340) |
| 56 | chr15:23793989 | GTCCTGCCTCCTAGTTTTT ATTGACT (SEQ ID NO: 341) | TGGAGGTAAAGGCAAAC ACTGATC (SEQ ID NO: 342) |
| 57 | chr15:23816231 | CATGTGTCTCGATTTGATG GATATCCA (SEQ ID NO: 343) | CTAACTCTATCCCGCACTG AAGT (SEQ ID NO: 344) |
| 58 | chr15:23893430 | CAGACCAGTCAGACTCCA CATG (SEQ ID NO: 345) | GCCTTTTCCATGTCTTTGA CTCCT (SEQ ID NO: 346) |
| 59 | chr15:23929209 | CTCTGACAGCAGAGAGGA AAGTG (SEQ ID NO: 347) | GATGTTTCATTTCTGGAGT AGGACTGT (SEQ ID NO: 348) |

TABLE 3-continued

Hypermutational SNP sites in proximity to acrocentric location of Chromosome 15 and detecting primers

| No. | chromosome: location | forward primer sequence (5'->3') | reverse primer sequence (5'->3') |
|---|---|---|---|
| 60 | chr15:24006330 | GGGATGTTGGCTTGTGTGTTTTT (SEQ ID NO: 349) | AACTTCCTTTCCTCTTTTTGCATTGTC (SEQ ID NO: 350) |
| 61 | chr15:24055535 | GTGAATGCCCTCTTCAATGTAATGAAAT (SEQ ID NO: 351) | GGTTACTTGAGGTGCAGACTGA (SEQ ID NO: 352) |
| 62 | chr15:24129894 | AGACCTCTTGCATTTCCATATAGATTTTCA (SEQ ID NO: 353) | ACAGTTCATTTAAACAAGCATCAAGAAGAAAAA (SEQ ID NO: 354) |
| 63 | chr15:24166516 | TGGTTTGTTGGTTGATTGTTTGTGT (SEQ ID NO: 355) | ACATACATATTCTTTGCTATCAGCTGACAA (SEQ ID NO: 356) |
| 64 | chr15:24196094 | AAACTTTGTTTAGTGGTTAAACTAGGCAAT (SEQ ID NO: 357) | ACTTGACAGAAAGTGTGAACACCT (SEQ ID NO: 358) |
| 65 | chr15:24236177 | GGTTTGATACTTGTAGAGCCAGGTA (SEQ ID NO: 359) | CACAATGCAAGAGGAGATGTCCT (SEQ ID NO: 360) |
| 66 | chr15:24278723 | TGCTTATTGTATGTGACTATCACTTCCTTG (SEQ ID NO: 361) | ATGCACAAGCATAAGAAACAGATGAAAAA (SEQ ID NO: 362) |
| 67 | chr15:24319610 | CCCATGCAGACAATCTTTGGTTG (SEQ ID NO: 363) | AGCTCCATCATATTCTCATGAGACCT (SEQ ID NO: 364) |
| 68 | chr15:24350583 | AGGTTTTATGGTTTTTATGGTTTTTATGGTTT (SEQ ID NO: 365) | AACAAAACTATACATGTATCCACAAACCTAAAT (SEQ ID NO: 366) |
| 69 | chr15:24471640 | ACCTGGGTGACAAGAAAGAGAGA (SEQ ID NO: 367) | GTCTTGTCCCTTCAGAGTTTACAGT (SEQ ID NO: 368) |
| 70 | chr15:24824114 | AAAAATAGAAAGAAGTGTCCCTCATCTGT (SEQ ID NO: 369) | CCTTCTGCATGCCCTGTATACC (SEQ ID NO: 370) |
| 71 | chr15:24870875 | TCTGTCATTTCTTGTTTGCTTTTGAGG (SEQ ID NO: 371) | GAAAGGAGCCATAAGGATGTATTCCAATAT (SEQ ID NO: 372) |
| 72 | chr15:24913763 | AGAAGTTCAGGTGATTACTTGGCATT (SEQ ID NO: 373) | AAATGGCAGAGATAGAGCAGAAGTG (SEQ ID NO: 374) |
| 73 | chr15:24943341 | TCTGCTGTATGTTTCCATTTCTGATAGAG (SEQ ID NO: 375) | GCTAGCATTAAAAGAAAGTACGTGTATCTG (SEQ ID NO: 376) |
| 74 | chr15:24974072 | ACCTCCATGATGCCTATGAGCT (SEQ ID NO: 377) | TGCTGTGCACCAGCCAATTAATA (SEQ ID NO: 378) |

TABLE 4

Hypermutational SNP sites in proximity to acrocentric location of Chromosome 21 and detecting primers

| No. | chromosome: location | forward primer sequence (5'->3') | reverse primer sequence (5'->3') |
|---|---|---|---|
| 1 | chr21:14640496 | CCTTCGGATGAAAATGAGGATAAGATAATATGA (SEQ ID NO: 379) | GGAGCTTTCAATGTAATTTCTACTAGAATTGG (SEQ ID NO: 380) |

TABLE 4-continued

Hypermutational SNP sites in proximity to acrocentric location of Chromosome 21 and detecting primers

| No. | chromosome: location | forward primer sequence (5'->3') | reverse primer sequence (5'->3') |
|---|---|---|---|
| 2 | chr21:14643423 | ACTCTTTATCTCATTTATCTGAAGAAAATGCAC (SEQ ID NO: 381) | CCCTGTAACAGGGCTTACTTCATT (SEQ ID NO: 382) |
| 3 | chr21:14695894 | CAGACTTGCATAGAGCCTGTATGT (SEQ ID NO: 383) | CTTAGCCTCCAACCTACATCTTTCTC (SEQ ID NO: 384) |
| 4 | chr21:14756515 | TCTCTTAGCTTTCAATTTGGTGGAAATGA (SEQ ID NO: 385) | ACCTTCCTGAAAGAAAATGGCCTT (SEQ ID NO: 386) |
| 5 | chr21:14818516 | CAAGGTGGTAACAGCCTACCAA (SEQ ID NO: 387) | CCTGTATCTTCGCTTCTGTTCTTAACAT (SEQ ID NO: 388) |
| 6 | chr21:14890028 | GAGGATGGTAAGGATAGAGGAAAGAAGA (SEQ ID NO: 389) | CACCTTCTTTTCTCAACCACCTTTG (SEQ ID NO: 390) |
| 7 | chr21:15012159 | GCAGATAGAAGTGGCTGAACAGA (SEQ ID NO: 391) | TGCAGTTGAATTAAGAACATGGTTTTATCCTAT (SEQ ID NO: 392) |
| 8 | chr21:15026905 | CAAATCCCTTTACAGGTTAGTTTGTAAAATCAG (SEQ ID NO: 393) | TCAATGGGTCTTAATAATCAAATGACTCCA (SEQ ID NO: 394) |
| 9 | chr21:15170049 | CTTTTTCCACCTTGAATGCATGAGA (SEQ ID NO: 395) | GGGTTTTCTGGAGAGATAGTGGTAG (SEQ ID NO: 396) |
| 10 | chr21:15280687 | CCTCATCACTGTCACCTTAGAGTG (SEQ ID NO: 397) | GAAAGAGAAAGTGAGAAGATGTGTTGAATG (SEQ ID NO: 398) |
| 11 | chr21:15300595 | ACACATGGTCTCATCCAGAAATCTATTTTT (SEQ ID NO: 399) | CAAACAAACAAACAGAAAGGAATAGGACTG (SEQ ID NO: 400) |
| 12 | chr21:15445542 | GACCTGCCTCGCTACCTTTTA (SEQ ID NO: 401) | GCTTGTACTCAGAATGCATGTCTC (SEQ ID NO: 402) |
| 13 | chr21:15479041 | TGAGTTATTCTGGAAGACTGTTATCACCT (SEQ ID NO: 403) | CACACAACCTCATGCTATTTTACTTTTCT (SEQ ID NO: 404) |
| 14 | chr21:15501432 | CAGAGCCTTCCTATATCCTTAACAACG (SEQ ID NO: 405) | AACAGGCTGACCACGTCATAATT (SEQ ID NO: 406) |
| 15 | chr21:15548748 | TGCAAAATTTGGCTTTTTAAATCATCTGC (SEQ ID NO: 407) | GCCATGGCTAGAAGTTAATGTATAGTTTTG (SEQ ID NO: 408) |
| 16 | chr21:15566056 | CAATGCAAAATGTAACTAAAAGTGAGCAGA (SEQ ID NO: 409) | CGCCTGTGGTTCTGTTCTTGTA (SEQ ID NO: 410) |
| 17 | chr21:15588845 | GTTCCTTCAGGTACCGTCTCTG (SEQ ID NO: 411) | GGAAGCCCTTAATCAGAAACGGG (SEQ ID NO: 412) |
| 18 | chr21:15625530 | CTGGCGGTATCTCATCCATCAA (SEQ ID NO: 413) | CCTCTGAGATACATTTCAAGAAGGGTT (SEQ ID NO: 414) |
| 19 | chr21:15654618 | GGAAGAACCTATTGAATAGGCTGAACA (SEQ ID NO: 415) | GATCTTCATGTTGCCAAATTTAATGGAGAA (SEQ ID NO: 416) |

TABLE 4-continued

Hypermutational SNP sites in proximity to acrocentric location of Chromosome 21 and detecting primers

| No. | chromosome: location | forward primer sequence (5'->3') | reverse primer sequence (5'->3') |
|---|---|---|---|
| 20 | chr21:15681452 | ACAACCACAAAAAGAATT TCCTATGTTGTC (SEQ ID NO: 417) | ATGACAAGTTGGCTATAG CTTGTTACATTA (SEQ ID NO: 418) |
| 21 | chr21:15720558 | TGACCTAATATCAAATTTT TCAGGGCGTAT (SEQ ID NO: 419) | CCTGGACAAAGAGGAGG TTTAAGTG (SEQ ID NO: 420) |
| 22 | chr21:15763305 | AGCTATGGATATAGATCAA TGCATGGATTT (SEQ ID NO: 421) | GCATCCTTCAAGACATGAT AAAAGGACTAA (SEQ ID NO: 422) |
| 23 | chr21:15842397 | CCAACTTGCAATGAGATG GTTCTT (SEQ ID NO: 423) | GCACAGGGTTTTGCTACA ATTTTACTTAAA (SEQ ID NO: 424) |
| 24 | chr21:15884516 | AATTGATGCAAATGTGCTA CATTTTTCAG (SEQ ID NO: 425) | GCTCCTCGGGATACTCCTC AAA (SEQ ID NO: 426) |
| 25 | chr21:15916232 | GGTCACTTGAAATAGAAC CAATGACAGT (SEQ ID NO: 427) | ACAGAACCATCAAGAAAT TGGTCTGA (SEQ ID NO: 428) |
| 26 | chr21:15942816 | CACAAATGAAAGCCACCC TTAATATTCA (SEQ ID NO: 429) | CGACTGCACATTCCAAAT CTGTC (SEQ ID NO: 430) |
| 27 | chr21:15984234 | ACTGCAGGACCCTGATAG GATC (SEQ ID NO: 431) | TTTTTAATGTAGTGTGCCA AACTTATGGG (SEQ ID NO: 432) |
| 28 | chr21:16027704 | CTAGACCTTTCATAAGAGA GAATTAGAAAATGC (SEQ ID NO: 433) | ACCTAAAATTGATCTGTTG TTTTCTTGCATTA (SEQ ID NO: 434) |
| 29 | chr21:16063848 | AAGTTGGTTGCTGCAGTTT TCTG (SEQ ID NO: 435) | AGTTTTACAGTCACCTGC TGATAATTTGA (SEQ ID NO: 436) |
| 30 | chr21:16122140 | GGGAGGCTTTGATAAAAG CCCA (SEQ ID NO: 437) | CACATCATTTACTTTGAAC ACTTCTGTCT (SEQ ID NO: 438) |
| 31 | chr21:16160041 | TCTACATGGCCCATCAGAG GAA (SEQ ID NO: 439) | GGGATGTACATGGACATAA TATAAGCCATG (SEQ ID NO: 440) |
| 32 | chr21:16193235 | GCAATGGTTGAGGAAATT TCAAAATAGC (SEQ ID NO: 441) | GCCAACTGATGTTCCTTAA TGGCA (SEQ ID NO: 442) |
| 33 | chr21:16238898 | CTGATCCAATATTACTGGC ATCCTTCT (SEQ ID NO: 443) | AAGAAATTGATCACATCA CAGTTCTGGA (SEQ ID NO: 444) |
| 34 | chr21:16315932 | CTTGTTGGAGACAAAGTG AATAAGCC (SEQ ID NO: 445) | AATGCTTCAGATTTAGGA AGAATTAGGAGT (SEQ ID NO: 446) |
| 35 | chr21:16353639 | AGAGTCAATAAATCTGACT AGGTCCCAT (SEQ ID NO: 447) | TTGGTTGTATGGATAGATG GGCAAA (SEQ ID NO: 448) |
| 36 | chr21:16384555 | CATCCTTTTTCCTCCCAAT CATTATCTTTG (SEQ ID NO: 449) | GGTCAAATAAGCTTGGGA GATGTTG (SEQ ID NO: 450) |
| 37 | chr21:16448591 | CCTTTTCATAGGCATTGAA AAATCGTTTTC (SEQ ID NO: 451) | ATTGATGGTGCATTAGAG GAAAAGATTTG (SEQ ID NO: 452) |
| 38 | chr21:16578538 | TCAGTTTCCTCCAGATATA CTCTATGGTC (SEQ ID NO: 453) | GGCAGTCTTGCCTGGTTG ATAT (SEQ ID NO: 454) |

TABLE 4-continued

Hypermutational SNP sites in proximity to acrocentric location of Chromosome 21 and detecting primers

| No. | chromosome: location | forward primer sequence (5'->3') | reverse primer sequence (5'->3') |
|---|---|---|---|
| 39 | chr21:16645724 | TGAAGAAAATAAATGCAATTGTGAATGCCT (SEQ ID NO: 455) | CAGAGTAAGATGCCTTTTATTTGCTAAAGT (SEQ ID NO: 456) |
| 40 | chr21:16717265 | ACTCAGTTCTTTTTCCTTGACTTCTTCC (SEQ ID NO: 457) | ACACTGACTGATTGAATTTGTGTGGA (SEQ ID NO: 458) |
| 41 | chr21:16833315 | GCAATTTTTCTTTCTGAAAGTCTGAAGCT (SEQ ID NO: 459) | CAAATGGGATGCTCATCTTCTCAATTTTT (SEQ ID NO: 460) |
| 42 | chr21:16881542 | TCAGCCAGGGAAATAATTTCTCTTTTCT (SEQ ID NO: 461) | ATCCTCCATCCAAGTACCCTGT (SEQ ID NO: 462) |
| 43 | chr21:17000938 | GTTATCTGAATCCAAATACCTACACACACA (SEQ ID NO: 463) | CCTCTCTCAATGGAAAATTCAGATGAATTG (SEQ ID NO: 464) |
| 44 | chr21:17054831 | GATGGAGCAGCTTCCTGTGTAA (SEQ ID NO: 465) | TTTAGGTGCAATTGTAAGTCACAGGA (SEQ ID NO: 466) |
| 45 | chr21:17140290 | GTGAAGCAAGCAGGAAATTGACTAAA (SEQ ID NO: 467) | TTCTCCCTAAGGGAACCTATTCAAAATTTT (SEQ ID NO: 468) |
| 46 | chr21:17203891 | TGTGGGTTTCATGGAATGTGGT (SEQ ID NO: 469) | TATGTACATTAAACAGTATGCACTGGCAT (SEQ ID NO: 470) |
| 47 | chr21:17295288 | TCATGGGACTCTTATTTCCATTGCAA (SEQ ID NO: 471) | CCCAGAGGTAGCCATGTGACTA (SEQ ID NO: 472) |
| 48 | chr21:17340912 | AAAAGACAAAGAAAGCAAATGTGGAACA (SEQ ID NO: 473) | CTTCCACCTCTGAAACATAGTAAGCTAC (SEQ ID NO: 474) |
| 49 | chr21:17536247 | CCCTCAGACTTTTCTTGTAAATCCTATAGG (SEQ ID NO: 475) | CTCAGTGAGTGAAGCCATACGATA (SEQ ID NO: 476) |
| 50 | chr21:17640426 | GGGAGTAAATGGTCTTTAGGGATCAT (SEQ ID NO: 477) | AGGGCAGTGGAAGTAAAACCTTTTT (SEQ ID NO: 478) |
| 51 | chr21:17673255 | TGTTATATCCCACATCTCATTTCTGAGAGA (SEQ ID NO: 479) | GAAAGGCCAGGAGAAAAGGTCTT (SEQ ID NO: 480) |
| 52 | chr21:17713264 | TGATAAATTTTTCAGATCCTTCACCACTCT (SEQ ID NO: 481) | TCCAAGTTCTTTTCTGTTCACCTTATTGAT (SEQ ID NO: 482) |
| 53 | chr21:17748703 | CTAGTCCTCCCAACTTGCTTGT (SEQ ID NO: 483) | GTAACATTGAGCAGCAGCAACA (SEQ ID NO: 484) |
| 54 | chr21:17781159 | ATCTGGCCAGATGAAAATGGGATT (SEQ ID NO: 485) | CCCTACTGCGTTTAACAACCAATC (SEQ ID NO: 486) |
| 55 | chr21:17823782 | TGGAGTTTATCACCAAGTCATTTTATGTCC (SEQ ID NO: 487) | ACAGAAAGAGCTTGTAATTCTTCCTTTCA (SEQ ID NO: 488) |
| 56 | chr21:18003355 | CTTCACAGAATGGGATAACTGCCT (SEQ ID NO: 489) | CCTGACACATTCTGCATTCCCAT (SEQ ID NO: 490) |

TABLE 4-continued

Hypermutational SNP sites in proximity to acrocentric location of
Chromosome 21 and detecting primers

| No. | chromosome: location | forward primer sequence (5'->3') | reverse primer sequence (5'->3') |
|---|---|---|---|
| 57 | chr21:18046650 | ACTTTGTTCCCTGAATATA AAGAGCAAGT (SEQ ID NO: 491) | GTATCTTAGATATTCCCAG CTTTGTGCA (SEQ ID NO: 492) |
| 58 | chr21:18114449 | CGAAGGGCTTTGTCTAGAT AAACATAACA (SEQ ID NO: 493) | GTGGATGAGAGGTGTGGA TCTT (SEQ ID NO: 494) |
| 59 | chr21:18151760 | CCCACTGACCAAATCTGG ACAT (SEQ ID NO: 495) | GGACATTCTTTGACACTCT GAAATAGC (SEQ ID NO: 496) |
| 60 | chr21:18182817 | TTGTTTGTAGTGACTACAC AACTCAGT (SEQ ID NO: 497) | CTGACAGAAAATTTTCCA ACAGCTGTT (SEQ ID NO: 498) |
| 61 | chr21:18250262 | CCTGAAAAATATGTGGATC AACCGAAAA (SEQ ID NO: 499) | GAAAAGAGAAACATCAA GAGTCAGTTTTGG (SEQ ID NO: 500) |
| 62 | chr21:18337678 | GCTCATTCTCATTTTTGGC TTCCA (SEQ ID NO: 501) | CTACAGAATACCACTCAG CTGCAA (SEQ ID NO: 502) |
| 63 | chr21:18385770 | TGAGGAGGATACTTCTGTT ATTCCATCA (SEQ ID NO: 503) | CCCTTTCTTTCCTGAAAAT AAGTGCAG (SEQ ID NO: 504) |
| 64 | chr21:18420873 | CCCACCTCCAAATTGTATC CCATT (SEQ ID NO: 505) | AGTACTGGTTGTGCATTAT TAAATATGCAA (SEQ ID NO: 506) |
| 65 | chr21:18457287 | ACTGCACTCAATGAAACC ATCTGA (SEQ ID NO: 507) | GGATTTGCCTTTAATACTC AGGGATACAAT (SEQ ID NO: 508) |
| 66 | chr21:18586049 | ACCATGTTTTAACTCTTCT TTTAAAGCTGT (SEQ ID NO: 509) | GTCAAACCAGCTTAAGTT TAAAAAGCCATA (SEQ ID NO: 510) |
| 67 | chr21:18650837 | GAGCATGTTTCCTGAACAA TCATTGG (SEQ ID NO: 511) | TTTTTGTTGTTGTAGATTG TTGTTGCTG (SEQ ID NO: 512) |
| 68 | chr21:18740886 | AGATGTATTACCTTCATAG TCTCTGGGTTT (SEQ ID NO: 513) | TGTGGTTCCTCAGCTGTC AAATC (SEQ ID NO: 514) |
| 69 | chr21:18858018 | CAACCAATCAAGCAGCAG TGAAT (SEQ ID NO: 515) | GGTGCAGGGACAGCCTTT TTAT (SEQ ID NO: 516) |
| 70 | chr21:18936951 | TGGTTTGTTGGCTTCACAG ATGT (SEQ ID NO: 517) | GCTGAAAACACTACAGAT TTAAGTTTGCTG (SEQ ID NO: 518) |
| 71 | chr21:19002939 | TCCTGTCATTTCACTCCTA CATACTTCA (SEQ ID NO: 519) | AAGAAGGAAGAAGGAAG TCTTCTCTACA (SEQ ID NO: 520) |
| 72 | chr21:19064396 | CGGTGCATTAGGAAGCCA AGTT (SEQ ID NO: 521) | CACATGAATATCCAAATGT CCAATTGTCAT (SEQ ID NO: 522) |
| 73 | chr21:19139888 | GCCCTACCTCCTAATACAA CCATATC (SEQ ID NO: 523) | CTTTTCAGGTGCACCGTC TTTG (SEQ ID NO: 524) |
| 74 | chr21:19254923 | GCCTGGCCTCTGTTTGTCT TTTATAA (SEQ ID NO: 525) | GTACTCTTATTAATGCCTC CTTTGGTCA (SEQ ID NO: 526) |

TABLE 4-continued

Hypermutational SNP sites in proximity to acrocentric location of Chromosome 21 and detecting primers

| No. | chromosome: location | forward primer sequence (5'->3') | reverse primer sequence (5'->3') |
|---|---|---|---|
| 75 | chr21:19316600 | CTGCTTGACTTTAGAAGGATGATGGA (SEQ ID NO: 527) | GGCTGGTGTAGAGCCACTTAAC (SEQ ID NO: 528) |

TABLE 5

Hypermutational SNP sites in proximity to acrocentric location of Chromosome 22 and detecting primers

| No. | chromosome: location | forward primer sequence (5'->3') | reverse primer sequence (5'->3') |
|---|---|---|---|
| 1 | chr22:16415691 | CAGCCATTTTTCACGTTGCAGT (SEQ ID NO: 529) | CCCTGGAGAAAGCAGTTCTTTAC (SEQ ID NO: 530) |
| 2 | chr22:16554800 | CTAATTGAGGGACAGACACTCACA (SEQ ID NO: 531) | GCTACTGGATTCTGAGTGTGTGTTC (SEQ ID NO: 532) |
| 3 | chr22:16848067 | TCGAATGGAGTTGAATGGAATTATCAAAGA (SEQ ID NO: 533) | CATTTGTGTCCATTCTATGATTCCATTTCA (SEQ ID NO: 534) |
| 4 | chr22:16850056 | GAATAATCAAATGGAGACGAATGGAATCC (SEQ ID NO: 535) | CTATTCGGTGATTACATTCGATTGCATTT (SEQ ID NO: 536) |
| 5 | chr22:16850858 | AGAATCGAATGGAATAATCATCGAATGTACTA (SEQ ID NO: 537) | ATTTTTCCATTTGATACCATTCGATGATGATTC (SEQ ID NO: 538) |
| 6 | chr22:16851557 | CTAAGGGAATAATCGAACGGACTCAA (SEQ ID NO: 539) | TCGATTTCTCCATTTAATTCCATTCGATGA (SEQ ID NO: 540) |
| 7 | chr22:16852464 | TGGAATCATCGAATGTCATTGAATGGA (SEQ ID NO: 541) | TAGTCTATTCGATGATTCCATTCGAGTCTA (SEQ ID NO: 542) |
| 8 | chr22:16852792 | CGAAAGGAATCATCTTCAAAAGGAAGTG (SEQ ID NO: 543) | CCATTCGATTCCAAAAGATGATTCCCT (SEQ ID NO: 544) |
| 9 | chr22:16853453 | AATGGAATCATCATGAATGGAATCAAAGG (SEQ ID NO: 545) | CCATTCGAGTCCATTCAACAATGATTG (SEQ ID NO: 546) |
| 10 | chr22:16854397 | GAAATCAAATGGAATCAATGAATGGACTCA (SEQ ID NO: 547) | GATTCAATTCGATGATGATTTGATTGGAGT (SEQ ID NO: 548) |
| 11 | chr22:16855647 | CACGAATGGAATCATCACTGAATGAAG (SEQ ID NO: 549) | CGATTCCATTTGATTAGGATTCAATTCCAG (SEQ ID NO: 550) |
| 12 | chr22:16856500 | AGAATCGAACCGAATGGAATCATCTT (SEQ ID NO: 551) | GGTGATTACATTGAATTCCTTTCGATGATG (SEQ ID NO: 552) |
| 13 | chr22:16857432 | TGGAATCATCATCAAATAGTATCGAAAGGAATC (SEQ ID NO: 553) | TCAATTCCATTTGATAATTATTCCATTCGATTC (SEQ ID NO: 554) |
| 14 | chr22:16858287 | AAATGTAATCCAATGGAATCCTCGACT (SEQ ID NO: 555) | CATTCGATTCCTTTCGAGGATTTTATTCA (SEQ ID NO: 556) |

TABLE 5-continued

Hypermutational SNP sites in proximity to acrocentric location of Chromosome 22 and detecting primers

| No. | chromosome: location | forward primer sequence (5'->3') | reverse primer sequence (5'->3') |
|---|---|---|---|
| 15 | chr22:16860547 | AATCATTGAATGGAATCAA ACAGAATCGTC (SEQ ID NO: 557) | TTGGTGACTCCATTTGAC ACCAT (SEQ ID NO: 558) |
| 16 | chr22:16861742 | TCGAATGGAATCATCCAAT GAAGTCTAATG (SEQ ID NO: 559) | CTCCGATCCATGATTCCAT TCGATT (SEQ ID NO: 560) |
| 17 | chr22:16867995 | GCTGGCCACGGCTTTTTAC (SEQ ID NO: 561) | CGGGTGTGCAAAAATCCG C (SEQ ID NO: 562) |
| 18 | chr22:17031697 | CCACTAAACAGAGATTCT GGATTCAAGG (SEQ ID NO: 563) | GCGTCTCAACTTTATGTAC CTTAGGTAAAC (SEQ ID NO: 564) |
| 19 | chr22:17271213 | CACTGCACTAACCCTAGG CAATA (SEQ ID NO: 565) | TTTTTCTGCGTGGAAGCTT TCTAG (SEQ ID NO: 566) |
| 20 | chr22:17293257 | CACTTCCTCCAGTTTTTCC TACATAGA (SEQ ID NO: 567) | GCAAGTGTGTACTTTAAA ATGGCTAATGTT (SEQ ID NO: 568) |
| 21 | chr22:17409957 | CTTGTTTCCTTGTCATTATC TTAGGAGTCA (SEQ ID NO: 569) | ACAGAAGTCAGTGAGGA GTGTGA (SEQ ID NO: 570) |
| 22 | chr22:17442318 | TTTTTGGAGGAGGAAAGT CTGTTCA (SEQ ID NO: 571) | CACATTGGACTCAAACTT GGCTATG (SEQ ID NO: 572) |
| 23 | chr22:17469090 | CTACCTTGCATGTTCTGCT CTCT (SEQ ID NO: 573) | CCTCTAGCAGCCCACTTTA GGA (SEQ ID NO: 574) |
| 24 | chr22:17525677 | CTTACAGCAGGGAACAAA GTTCAC (SEQ ID NO: 575) | CGGGTTCCAATCTGGGTT TCAA (SEQ ID NO: 576) |
| 25 | chr22:17563259 | CCTGGGCACTAGACATAG CAAC (SEQ ID NO: 577) | CACTGTGCCCAGTCAAAT ATTTTGA (SEQ ID NO: 578) |
| 26 | chr22:17587785 | CGTCATCTGGGAAGCTGTT TCC (SEQ ID NO: 579) | GTGCAGGACACTTCGGAA AACAGAAG (SEQ ID NO: 580) |
| 27 | chr22:17619511 | AAATCAATGTTGCAAAGC AAAGGGA (SEQ ID NO: 581) | AGCATCCTCACTTACCAGT ATGC (SEQ ID NO: 582) |
| 28 | chr22:17656792 | AAAATCACCATTTGATGGT TGTATTTCCA (SEQ ID NO: 583) | CATTATTTCTGCCATACTT CGTTGGT (SEQ ID NO: 584) |
| 29 | chr22:17682387 | CAGCATTCTGACTTTCTTG TTTACACA (SEQ ID NO: 585) | AGAGAGTCTGCTCGTTCA TTTACATATTG (SEQ ID NO: 586) |
| 30 | chr22:17715164 | GGAGACAGGTTCACATGA AAAAGTT (SEQ ID NO: 587) | GTGAAAGCAGGAGCTTCT TGGA (SEQ ID NO: 588) |
| 31 | chr22:17739757 | CCCAAGGAAAACGGGTTT ATGG (SEQ ID NO: 589) | CACACATGTGCATGCTACT GAA (SEQ ID NO: 590) |
| 32 | chr22:17761489 | AAGAAACTTGGTTTCATTT TCCATTAAGGT (SEQ ID NO: 591) | AGTAATAAGCAACCCAAA CTTAGCCA (SEQ ID NO: 592) |

TABLE 5-continued

Hypermutational SNP sites in proximity to acrocentric location of Chromosome 22 and detecting primers

| No. | chromosome: location | forward primer sequence (5'->3') | reverse primer sequence (5'->3') |
|---|---|---|---|
| 33 | chr22:17785311 | TGGCTCTGACTTCATGATCATGG (SEQ ID NO: 593) | GGCTTGGAAGCATAAGTAGGATGTAG (SEQ ID NO: 594) |
| 34 | chr22:17805528 | CCAGCCTGCCAACACAATATTG (SEQ ID NO: 595) | CCATTAACTGTATCTATGCTTGTCTGTCT (SEQ ID NO: 596) |
| 35 | chr22:17841251 | TATGGAAATCACTGAAAAGTGGAGAAACT (SEQ ID NO: 597) | GTTTTGTTTGTTTTTCAAATGGTGTCTCA (SEQ ID NO: 598) |
| 36 | chr22:17883346 | TTGGAAATTCTTTCAGGTTGACTCCTT (SEQ ID NO: 599) | AAAACAAGTTTGCCAGTTTCTTTAGAAGTT (SEQ ID NO: 600) |
| 37 | chr22:17916190 | GGGAAAAGGATTTTGTATTTCATGTCATCC (SEQ ID NO: 601) | GGCAAGACCATCTAATGGCACT (SEQ ID NO: 602) |
| 38 | chr22:17939998 | CCCGGTATCCTTATGTCCCAGT (SEQ ID NO: 603) | GGATGGAACTAAAGGCCAGCTAA (SEQ ID NO: 604) |
| 39 | chr22:17981144 | TTTTTCCTTTAGAGCTGTGTGTGTAAG (SEQ ID NO: 605) | GCAAAGTGTATAACGCATTAGGATGAAGTA (SEQ ID NO: 606) |
| 40 | chr22:18012297 | GTGGCCTTTCCAGCTTCTAGTAG (SEQ ID NO: 607) | TTTCAAGTCATACACCACCTCAAATATGT (SEQ ID NO: 608) |
| 41 | chr22:18054406 | CTGACATGGTGTCATACACCTATGG (SEQ ID NO: 609) | ACAGCATGTGCCCTCCTAAAAG (SEQ ID NO: 610) |
| 42 | chr22:18212058 | AATACTTTACCTACCCTGATCACCAAAAC (SEQ ID NO: 611) | ACATCACTCCCTAAATGGGACACTA (SEQ ID NO: 612) |
| 43 | chr22:18276198 | CCACATGCCTTTCAACGACAAT (SEQ ID NO: 613) | GGGCTTTAAGTCTCAGATCCATCA (SEQ ID NO: 614) |
| 44 | chr22:18354015 | TTCTATCAATGTCAAGGTCTTTATGCCA (SEQ ID NO: 615) | GCAACATGTGCTGCCAGTTTTT (SEQ ID NO: 616) |
| 45 | chr22:18395978 | ATGGCTTTTACTAGGTGAAGGTAATTTTCT (SEQ ID NO: 617) | AGAGACATTTAAATAATGTCCTTGCAGAGT (SEQ ID NO: 618) |
| 46 | chr22:18466951 | GGCAAAACGCAAATCATCGTGA (SEQ ID NO: 619) | GGACCAGGGAAATCCTGAGTCT (SEQ ID NO: 620) |
| 47 | chr22:18531582 | TGACCCTCTTAGAACCCATTCCT (SEQ ID NO: 621) | AGGAGAGGCTTTTAAAATCGCTATGATT (SEQ ID NO: 622) |
| 48 | chr22:18581715 | AGATGCATGAAATGGCTACATAGATATGG (SEQ ID NO: 623) | GTTGATTTGTGGTTGCCTATGTAATTGTAT (SEQ ID NO: 624) |
| 49 | chr22:18628321 | GGCCCACACTTTCTTTTGAAACA (SEQ ID NO: 625) | GGGATTTGGGAGAAATGCAATGTC (SEQ ID NO: 626) |
| 50 | chr22:18894617 | CGCCTTTTTGGTGACCAATGTG (SEQ ID NO: 627) | GCTGTCAACAGACCTCCAACTA (SEQ ID NO: 628) |

TABLE 5-continued

Hypermutational SNP sites in proximity to acrocentric location of
Chromosome 22 and detecting primers

| No. | chromosome: location | forward primer sequence (5'->3') | reverse primer sequence (5'->3') |
|---|---|---|---|
| 51 | chr22:18966077 | CTGTGCTCTAAAGCCAGACTGA (SEQ ID NO: 629) | CTCTGTACACTGCCACATACCA (SEQ ID NO: 630) |
| 52 | chr22:19004846 | GCTGTATACGACAAAGCCATAGCT (SEQ ID NO: 631) | TTTTTCTCTTGCATATTTGTGTGATGTCT (SEQ ID NO: 632) |
| 53 | chr22:19025459 | CTGTGTCAGGCAACAAAACCAC (SEQ ID NO: 633) | CCCATTTGTGCCATAAAGGGTT (SEQ ID NO: 634) |
| 54 | chr22:19098323 | CAGAAGGAGAAAGACAAGGAGTAGATG (SEQ ID NO: 635) | CCTCATTTTACAGATAGAGAAACAGAGCTT (SEQ ID NO: 636) |
| 55 | chr22:19142652 | CACCAGGCCCTCATCTCTTAAC (SEQ ID NO: 637) | ATGAGGGCAAAGACTCCCAAAC (SEQ ID NO: 638) |
| 56 | chr22:19236590 | GCCTGGCCCTTCTAAGAGTTTTA (SEQ ID NO: 639) | CATGATCATTTGAACTTATTCCTCCAGTCT (SEQ ID NO: 640) |
| 57 | chr22:19362714 | CCTCTCAGGAGGCAGAGAACTT (SEQ ID NO: 641) | GGTAGAGAGCTGCAATAAAAATGATGTAAG (SEQ ID NO: 642) |
| 58 | chr22:19431588 | CAGGCAGTTTCCCAAGGACTAG (SEQ ID NO: 643) | GATACCCTGACACTGCGATGTT (SEQ ID NO: 644) |
| 59 | chr22:19536367 | CGTGAGTCTGGGTGACAGT (SEQ ID NO: 645) | GGGAGCACATCAGCATTGTATCA (SEQ ID NO: 646) |
| 60 | chr22:19643965 | ATACCAAGAAACCCAAGAAAGAAAGGGTGA (SEQ ID NO: 647) | GGAAGCTTCTCCAAGGTAAGCT (SEQ ID NO: 648) |
| 61 | chr22:19716983 | CACCTCCAGAGGTCCTAGTGTA (SEQ ID NO: 649) | CACTTTCTCCTGGGCTGTACAT (SEQ ID NO: 650) |
| 62 | chr22:19759532 | GGGTCTCAGCCTAACTGAAGGA (SEQ ID NO: 651) | GGGAGGAGTGTCCTGAGAAATGAT (SEQ ID NO: 652) |
| 63 | chr22:19808057 | CATGAAGGGTCCAGTGGAGAT (SEQ ID NO: 653) | GGAGTCAGGAACTCTCTGATGGA (SEQ ID NO: 654) |
| 64 | chr22:19859087 | CGCCAGCGTGTACCTCTTT (SEQ ID NO: 655) | GGCACGGGAGCATCCTATG (SEQ ID NO: 656) |
| 65 | chr22:19909387 | CCAGAGGTCATGCACAGAAGAC (SEQ ID NO: 657) | TATGCTTTTCCCAGTCCAGATTCTG (SEQ ID NO: 658) |
| 66 | chr22:19972494 | ACCGTGTATCGGAGACCCTTAT (SEQ ID NO: 659) | CAGCCAACTCCTGTTGAGAGTC (SEQ ID NO: 660) |
| 67 | chr22:20016622 | CTGAGAGCCAGGGAAGCAGATC (SEQ ID NO: 661) | TCACTCCATGCGGTGTCTAAAAA (SEQ ID NO: 662) |
| 68 | chr22:20051573 | TGCAGGGTGTCATTTCCTTCAG (SEQ ID NO: 663) | GAAGCAAACATTCAGCACACTCT (SEQ ID NO: 664) |

TABLE 5-continued

Hypermutational SNP sites in proximity to acrocentric location of Chromosome 22 and detecting primers

| No. | chromosome: location | forward primer sequence (5'->3') | reverse primer sequence (5'->3') |
|---|---|---|---|
| 69 | chr22:20081918 | CTATAGACAGCTTGGCTCC ATGT (SEQ ID NO: 665) | GGCACGTGAGAAAACAG CTTTG (SEQ ID NO: 666) |
| 70 | chr22:20135421 | GCCTTAACTTCCTGGAGCC A (SEQ ID NO: 667) | CCCAAATGGGAGATGTAG AGCC (SEQ ID NO: 668) |
| 71 | chr22:20175034 | GGGATGCATTGCAGTAAA GAGC (SEQ ID NO: 669) | CCCATTCCCTGTCACTGTT ATCA (SEQ ID NO: 670) |
| 72 | chr22:20216874 | GGCTACAGAGACATGAAC CCAA (SEQ ID NO: 671) | GGCTCATGGCATGAACTT GCTA (SEQ ID NO: 672) |
| 73 | chr22:20278637 | GGGACAGTAGACAAGCTT ATCCCT (SEQ ID NO: 673) | GTCGAGATGCTTAATAGA GCCACAT (SEQ ID NO: 674) |
| 74 | chr22:20745699 | AGAAAGACTCAGACCTGA CCTGTT (SEQ ID NO: 675) | ACCTGTGCACAGGTGACT CTAT (SEQ ID NO: 676) |
| 75 | chr22:20787955 | GGATAGACTGGCCCTACA CCAT (SEQ ID NO: 677) | GTGGAAAATACACTGGAC CAATTCC (SEQ ID NO: 678) |
| 76 | chr22:20855585 | AAAAAGAAGATGGCGTAA TCAGAAGTTG (SEQ ID NO: 679) | GCAGAAGCAAATGGAAA GGAGAAATC (SEQ ID NO: 680) |
| 77 | chr22:20881195 | TATCTTCAGGCTCAGTGCT AGTGA (SEQ ID NO: 681) | GAAGCTGGCAGAATGAGG GAAT (SEQ ID NO: 682) |
| 78 | chr22:20924097 | GGGTGCTCAGTAATGTCCT TCA (SEQ ID NO: 683) | CAGAGACCTCCAACCTCA TCAC (SEQ ID NO: 684) |
| 79 | chr22:20983921 | TATGAGCAGGTCATGGCA GGTA (SEQ ID NO: 685) | CACTTAAATGTGAACAAA GTGTCCATTGA (SEQ ID NO: 686) |
| 80 | chr22:21028224 | TCAGGGAAGTATAAAAGT GACAGGGAT (SEQ ID NO: 687) | CCTCAGTTGCTCATCACTG TCAT (SEQ ID NO: 688) |

In the present invention, the sequencing process used may be high-throughput sequencing technology. The lengths of DNA fragments are 125-275 bp. In a specific embodiment according to the invention, the sequencing platform is Ion Torrent PGM and DNA sequence molecules with DNA lengths of 125-275 bp are obtained.

In the present invention, the sequencing depth may be 3003000×, i.e. each specific PCR amplified product is sequenced for 3003000 time. For example, in a specific embodiment of the invention, the sequencing depth is 1000, i.e. the specific PCR amplified product is sequenced for 1000 times.

In the present invention, when the DNA molecules for detection are from various samples, each sample can be provided with a different barcode so as to be differentiated during sequencing process (Micah Hamady, Jeffrey J Walker, J Kirk Harris et al. Error-correcting barcoded primers for pyrosequencing hundreds of samples in multiplex. Nature Methods, 2008, 5(3)), enabling sequencing of various samples at the same time.

In the present invention, the genome reference sequence may be obtained from public database. For example, the human genome sequence may be human genome reference sequence in NCBI or ucsc database.

In the present invention, the sequence alignment may be done with any sequence alignment program, for example, Torrent Mapping Alignment Program (TMAP) and BWA (Burrow-Wheeler-Aligner) available to a person skilled in the art can be used to perform alignment and the reads is aligned with reference genome sequence to give the location of the reads at the reference genome sequence.

In the present invention, Torrent_Server_4.0_VM software is used on raw data generated by PGM sequencer to remove linker sequence and Tmap software is used for alignment to human hg19 reference genome, and haplotype SNP covering multiple and genotype are analyzed finally.

In a particular embodiment according to the invention, the detecting method comprises the steps of:

DNA extracting and sequencing: After extracting cell DNA with MDA whole genomic amplifying process (Qiagen Kit), the library is constructed according to Ion AmpliSeq™Library Kits 2.0 standard procedures. During this period, embryo MDA whole genomic amplification is amplified to DNA molecules concentrated as about 125~275 bp through multiplex PCR. Two ends are added with linkers for sequencing, and each sample is provided with different barcode, thereby data of various samples obtained in data from one sequencing can be differentiated.

Alignment and statistics: Torrent_Server_4.0_VM software is used on raw data generated by PGM sequencer to remove linker sequence and Tmap software is used for alignment to human hg19 reference genome, and haplotype SNP covering multiple and genotype are analyzed finally.

The invention is useful for chromosomal Robertsonian translocation in preimplantation genetic diagnosis on suitable population, and is beneficial for providing genetic counseling and clinical decision basis. The invention is particularly suitable for detecting the condition that one of the parents is chromosomal Robertsonian translocation carrier and the other is normal karyotype, where normal embryo cannot be differentiated from chromosomal Robertsonian translocation carrying embryo according to conventional methods.

The following examples will be provided for detailed description which should not be construed as limitation thereto. The following examples are only parts of the invention, and based on the examples disclosed herein, a person skilled in the art can obtain all other examples which belong to the protection of the invention. Likewise, the accompanying figures are only those of some examples of the invention and based on the figures disclosed herein, a person skilled in the art can obtain all other figures which belong to the protection of the invention.

In case there is no specific description of the experimental conditions in the following examples, they were performed under conventional conditions or those recommended by the manufacture.

EXAMPLE 1

Detection of Embryo Chromosomal Robertsonian Translocation

I. Materials

Sample sources: 8 embryo blastula stage trophoblast cell whole genomic amplified products and parental peripheral blood cell DNA samples, the father carries chromosomal Robertsonian translocation in Chromosome 13 and Chromosome 14 while the mother has normal chromosome karyotype. Analysis results of embryo chromosome copy number are shown in Table 6.

TABLE 6

Parent and embryo chromosome karyotype information

| | No. | karyotype |
|---|---|---|
| Father | LH | 45, XY, der(13, 14) |
| Mother | YT | 46, XX |

TABLE 6-continued

Parent and embryo chromosome karyotype information

| | No. | karyotype |
|---|---|---|
| Embryo | YT_1 | 46, XY |
| | YT_2 | 46, XX |
| | YT_3 | 47, XY, +14 |
| | YT_4 | 46, XX |
| | YT_5 | 46, XX |
| | YT_6 | 45, XO |
| | YT_7 | 46, XX |
| | YT_8 | 46, XY |

II. Procedures

1. Library Constructing and Sequencing

The library was constructed according to Ion AmpliSeq™ Library Kits 2.0 standard Library construction procedures. Multiplex PCR reactions were performed with the primers in Table 1 and Table 2 and then DNA molecules of the amplified products were added with linkers at both ends for sequencing. Under certain conditions, the nucleic acid molecules were allowed to grow in clusters and sequencing were performed on Ion Torrent PGM to give DNA fragments sequences in target location with fragment lengths of 125 bp~275 bp.

In this example, the sequencing were performed on the DNA samples obtained from the 8 embryo cells and full blood DNA samples obtained from both of the parents according to official sequencing instruction by Ion Torrent.

2. Data Analysis

Torrent_Server_4.0_VM software was used on raw data generated by PGM sequencing to remove linker sequence and Tmap software is used for alignment to human hg19 reference genome. The sequences with low quality were removed and sequencing depth N of target sites were counted and the sites with N<100 were removed. All sequence directions and ratios of each of the bases at valid sites were analyzed. The base type that forward and reverse sequence number >20% and base ratios >10% was designated as one genotype of the site (X, X={A, T, C, G}).

Individual haplotype was speculated with genotypes of the parents and the embryo; while the valid site was the site providing valid SNP information for constructing pedigree haplotype and was generally the site in which one of the parents and the embryo is heterozygous. For the genotypes of the parents, ({X1X1}, {X2X2}), ({X1X1}, {X1X1}) was invalid site, ({X1X1}, {X1X2}) was valid site and ({X1X2}, {X1X2}) was verifiable site. According to valid site and verifiable site, haplotypes of parent and each of embryos were deduced. Male parent (LH), haplotypes of Chromosome 13 and Chromosome 14 were Aa and Bb, respectively and female parent (YT), haplotypes of Chromosome 13 and Chromosome 14 were Cc and Dd, respectively.

III. Results Analysis

Figure 3:
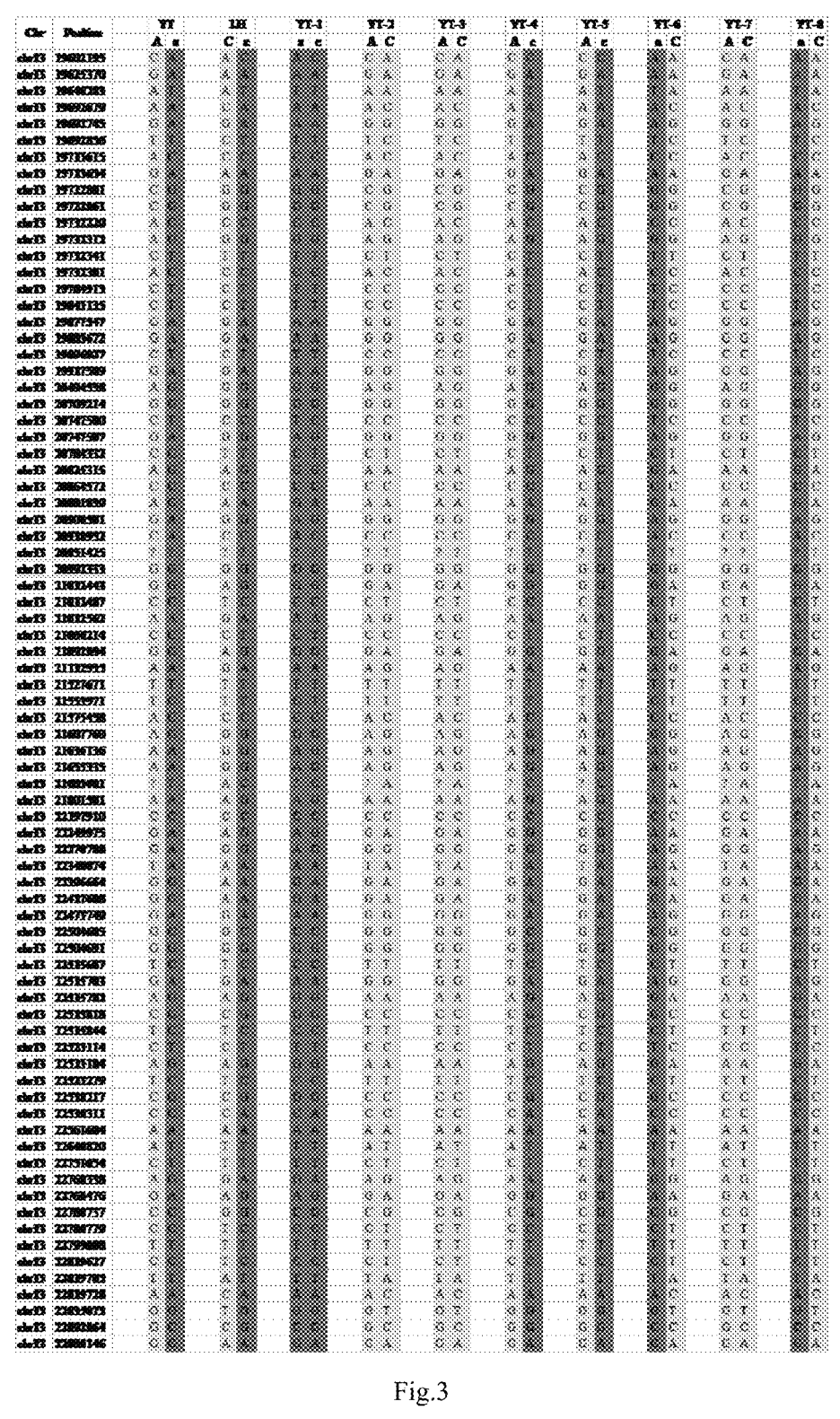
Figure 4:
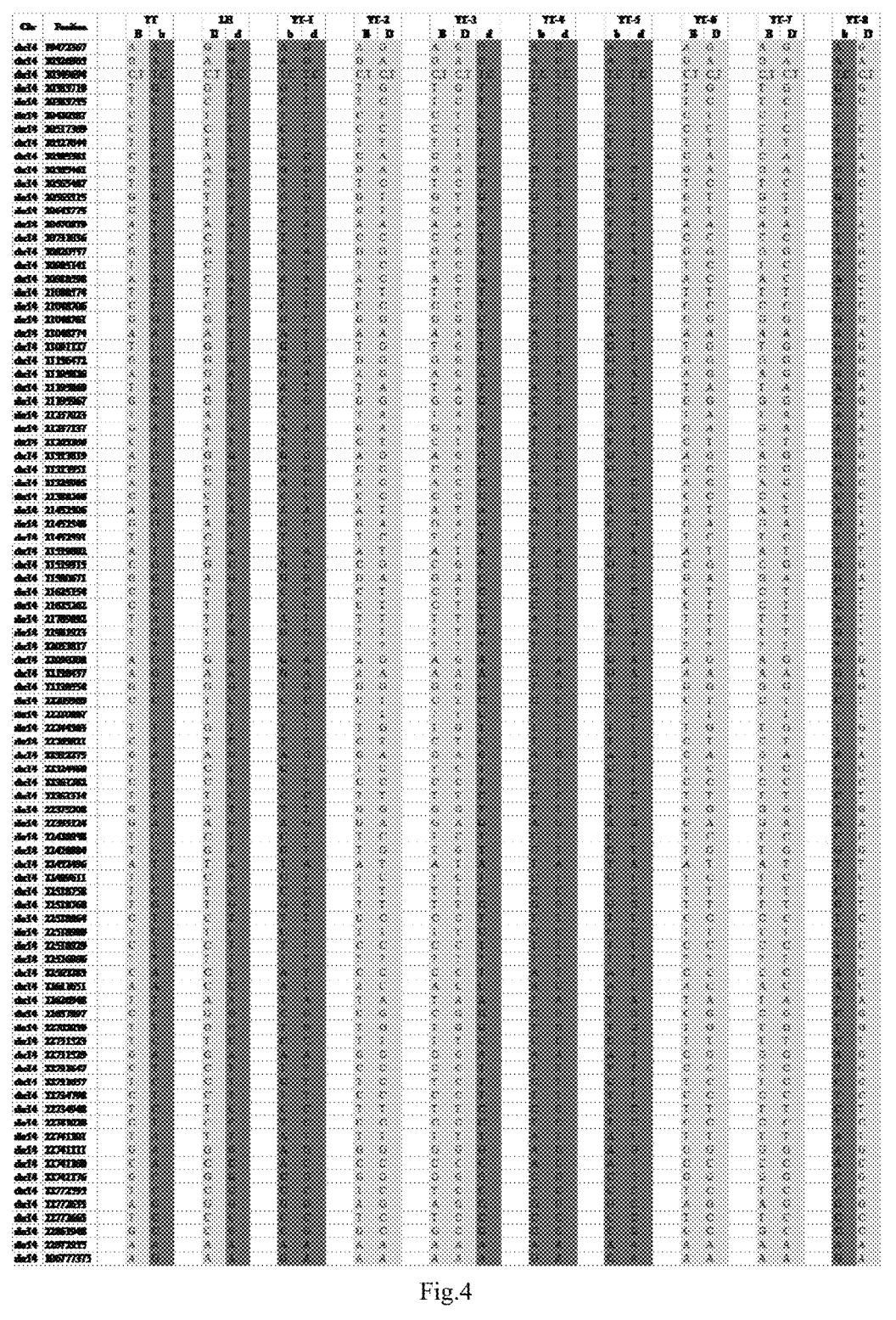

Pedigree haplotype was built according to 115 SNP sites in target location (57 and 58 for Chromosome 13 and Chromosome 14, respectively) (results were shown in FIG. 3 and FIG. 4) and pedigree haplotype analysis was shown in Table 7.

TABLE 7

Pedigree haplotype list

| | YT | LH | YT_1 | YT_2 | YT_3 | YT_4 | YT_5 | YT_6 | YT_7 | YT_8 |
|---|---|---|---|---|---|---|---|---|---|---|
| chr13 | Cc | Aa | ac | AC | AC | aC | aC | Ac | AC | Ac |
| chr14 | Dd | Bb | bd | BD | BbD | bd | bd | BD | BD | Bd |

According to the information that LH was translocation carrier and No. 3 embryo had Chromosome 14 duplication, it can be deduced that the Chromosome 13 haplotype from LH (A type) carried by No. 3 embryo was translocation chromosome haplotype. Further, according to other embryo carrying A type or a type, it can be deduced that B type in Chromosome 14 was translocation chromosome haplotype. Accordingly, it can be determined that No. 1, 4, 5 embryos carrying Chromosome 13 a type and Chromosome 14 b type were normal embryos; No. 2, 6, 7, 8 embryos carrying Chromosome 13 A type and Chromosome 14 B type were translocation carrying embryos.

EXAMPLE 2

Detection of Embryo Chromosomal Robertsonian Translocation

I. Materials

Sample sources: 6 embryo blastula stage trophoblast cell whole genomic amplified products and parental peripheral blood cell DNA samples, the father carries chromosomal Robertsonian translocation in Chromosome 13 and Chromosome 14 (JXD) while the mother has normal chromosome karyotype (HCC). Analysis results of embryo chromosome copy number are shown in Table 8.

TABLE 8

Parent and embryo chromosome karyotype information

| | No. | karyotype |
|---|---|---|
| Father | JXD | 45, XY, der(13; 14) |
| Mother | HCC | 46, XX |
| Embryo | HCC-1 | 45, XY, −22 |
| | HCC-2 | 45, XY, −13 |
| | HCC-3 | 45, XX, −15 |
| | HCC-4 | 46, XX |
| | HCC-5 | Not detected |
| | HCC-6 | 46, XY |

II. Procedures

1. Library Constructing and Sequencing

The library was constructed according to Ion AmpliSeq™ Library Kits 2.0 standard Library construction procedures. Multiplex PCR reactions were performed with the primers in Table 1 and Table 2 and then DNA molecules of the amplified products were added with linkers at both ends for sequencing. Under certain conditions, the nucleic acid molecules were allowed to grow in clusters and sequencing were performed on Ion Torrent PGM to give DNA fragments sequences in target location with fragment lengths of 125 bp~275 bp.

In this example, the sequencing were performed on the DNA samples obtained from the 6 embryo cells and full blood DNA obtained from both of the parents according to official sequencing instruction by Ion Torrent.

2. Data Analysis

Torrent_Server_4.0_VM software was used on raw data generated by PGM sequencing to remove linker sequence and Tmap software is used for alignment to human hg19 reference genome. The sequences with low quality were removed and sequencing depth N of target sites were counted and the sites with N<100 were removed. All sequence directions and ratios of each of the bases at valid sites were analyzed. The base type that forward and reverse sequence number >20% and base ratios >10% was designated as one genotype of the site (X, X={A, T, C, G}).

Individual haplotype was speculated with genotypes of the parents and the embryo; while the valid site was the site that providing valid SNP information for constructing pedigree haplotype and was generally the site in which one of the parents and the embryo is heterozygous. For the genotypes of the parents, ({X1X1}, {X2X2}), ({X1X1}, {X1X1}) was invalid site, ({X1X1}, {X1X2}) was valid site and ({X1X2}, {X1X2}) was verifiable site. According to valid site and verifiable site, haplotypes of parent and each of embryos were deduced.

Female parent (HCC), haplotypes of Chromosome 13 and Chromosome 14 were Cc and Dd, respectively and male parent (JXD), haplotypes of Chromosome 13 and Chromosome 14 were Aa and Bb, respectively.

III. Results Analysis

Pedigree haplotype was built according to 115 SNP sites in target location (57 and 58 for Chromosome 13 and Chromosome 14, respectively) (results were shown in FIG. 1) and pedigree haplotype analysis was shown in Table 9.

TABLE 9

Pedigree haplotype list

| | HCC | JXD | HCC-1 | HCC-2 | HCC-3 | HCC-4 | HCC-5 | HCC-6 |
|---|---|---|---|---|---|---|---|---|
| chr13 | Cc | Aa | AC | C | aC | AC | — | ac |
| chr14 | Dd | Bb | BD | bD | bD | BD | — | bD |

According to the information that JXD is translocation carrier and No. 2 embryo had Chromosome 13 deletion, it can be deduced that the Chromosome 14 haplotype from JXD (b type) carried by No. 2 embryo was normal chromosome haplotype, i.e. Chromosome 14 B type was translocation chromosome haplotype. Further, according to other embryo carrying B type or b type, it can be deduced that A type in Chromosome 13 was translocation chromosome haplotype. Accordingly, it can be determined that No. 1, 4 embryos carrying Chromosome 14 B type and Chromosome 13 A type were translocation carrier embryos; No. 3, 6 embryos carrying Chromosome 14 b type and Chromosome 13 a type were normal embryos. No result was detected for No. 5 embryo chromosome copy number analysis and there was no valid sequence for this detection.

INDUSTRIAL APPLICABILITY OF THE INVENTION

The invention is useful for embryo chromosomal translocation analysis on suitable population, and is beneficial for providing genetic counseling and clinical decision basis. A preimplantation genetic diagnosis can effectively prevent children patients from birth.

The suitable population according to the invention may be chromosomal Robertsonian translocation carriers determined by routine chromosome karyotype analysis.

The invention is not limited to the best embodiments as listed above. Anybody can achieve other products in various forms under the inspiration of the invention. The technical solution, no matter changes to the shape or structure, which is similar or identical to the invention, falls within the protection scope of the invention.

The invention claimed is:

1. A method for genotyping SNPs involved in chromosome Robertsonian translocation ("CRT"), the method comprising:
   (a) obtaining a CRT-carrier parent DNA sample, a non-CRT-carrier parent DNA sample, and a progeny DNA sample from a progeny of the CRT-carrier and the non-CRT-carrier parents;
   (b) performing PCR amplification on the obtained samples from both of the parents and the progeny to produce amplicons, wherein the PCR amplification uses each of the following primer pairs:
   (i) SEQ ID NO: 1 and SEQ ID NO: 2;
   (ii) SEQ ID NO: 3 and SEQ ID NO: 4;
   (iii) SEQ ID NO: 115 and SEQ ID No: 116;
   (iv) SEQ ID NO: 117 and SEQ ID NO: 118;
   (v) SEQ ID NO: 231 and SEQ ID NO: 232;
   (vi) SEQ ID NO: 233 and SEQ ID NO: 234;
   (vii) SEQ ID NO: 379 and SEQ ID NO: 380;
   (viii) SEQ ID NO: 381 and SEQ ID NO: 382;
   (ix) SEQ ID NO: 529 and SEQ ID NO: 530; and
   (x) SEQ ID NO: 531 and SEQ ID NO: 532; and
   (c) using the amplicons to genotype the SNPs, wherein the SNPs are located at the following genomic positions in the human reference genome hg19: chr13:19602195, chr13: 19625370, chr14: 19472367, chr14:20326905, chr15:20022190, chr15:20049922, chr21: 14640496, chr21: 14643423, chr22:16415691, and chr22: 16554800.

2. The method according to claim 1, wherein the CRT-carrier parent or the non-CRT-carrier parent DNA sample is extracted from a peripheral blood sample, while the progeny DNA sample is extracted an embryo, a fetus, or an abortion tissue.

3. The method according to claim 1, wherein the progeny is Robertsonian translocation chromosome trisomic or monosomic.

* * * * *

SEQUENCE LISTING

```
<160> NUMBER OF SEQ ID NOS: 688

<210> SEQ ID NO 1
<211> LENGTH: 32
<212> TYPE: DNA
<213> ORGANISM: artificial sequence
<220> FEATURE:
<223> OTHER INFORMATION: The forward primer for SNP of specific position
      (chr13:19602195)

<400> SEQUENCE: 1
ttcctcatga acctattgat tatgtttcag aa                                    32

<210> SEQ ID NO 2
<211> LENGTH: 25
<212> TYPE: DNA
<213> ORGANISM: artificial sequence
<220> FEATURE:
<223> OTHER INFORMATION: The reverse primer for SNP of specific position
      (chr13:19602195)

<400> SEQUENCE: 2
tctgaccgac aaataccaca atctc                                            25

<210> SEQ ID NO 3
<211> LENGTH: 21
<212> TYPE: DNA
<213> ORGANISM: artificial sequence
<220> FEATURE:
<223> OTHER INFORMATION: The forward primer for SNP of specific position
      (chr13:19625370)

<400> SEQUENCE: 3
tgttccaggg atggatggtc t                                                21

<210> SEQ ID NO 4
<211> LENGTH: 24
<212> TYPE: DNA
<213> ORGANISM: artificial sequence
<220> FEATURE:
<223> OTHER INFORMATION: The reverse primer for SNP of specific position
      (chr13:19625370)

<400> SEQUENCE: 4
gggtagaaaa ctggccagat gatg                                             24

<210> SEQ ID NO 5
<211> LENGTH: 22
<212> TYPE: DNA
<213> ORGANISM: artificial sequence
<220> FEATURE:
<223> OTHER INFORMATION: The forward primer for SNP of specific position
      (chr13:19646283)

<400> SEQUENCE: 5
```

```
cctcacagga gaggttgttt gc                                              22

<210> SEQ ID NO 6
<211> LENGTH: 29
<212> TYPE: DNA
<213> ORGANISM: artificial sequence
<220> FEATURE:
<223> OTHER INFORMATION: The reverse primer for SNP of specific position
      (chr13:19646283)

<400> SEQUENCE: 6
gcctgttttt gtctctgaaa taagaactc                                       29

<210> SEQ ID NO 7
<211> LENGTH: 22
<212> TYPE: DNA
<213> ORGANISM: artificial sequence
<220> FEATURE:
<223> OTHER INFORMATION: The forward primer for SNP of specific position
      (chr13:19692745)

<400> SEQUENCE: 7
gcagtccagg aatcctcctg ta                                              22

<210> SEQ ID NO 8
<211> LENGTH: 30
<212> TYPE: DNA
<213> ORGANISM: artificial sequence
<220> FEATURE:
<223> OTHER INFORMATION: The reverse primer for SNP of specific position
      (chr13:19692745)

<400> SEQUENCE: 8
atcccaaaac tattttcctt ctcctatcac                                      30

<210> SEQ ID NO 9
<211> LENGTH: 26
<212> TYPE: DNA
<213> ORGANISM: artificial sequence
<220> FEATURE:
<223> OTHER INFORMATION: The forward primer for SNP of specific position
      (chr13:19713634)

<400> SEQUENCE: 9
gtctggttgg ttagaatgtt ccatga                                          26

<210> SEQ ID NO 10
<211> LENGTH: 24
<212> TYPE: DNA
<213> ORGANISM: artificial sequence
<220> FEATURE:
<223> OTHER INFORMATION: The reverse primer for SNP of specific position
      (chr13:19713634)

<400> SEQUENCE: 10
cacagtggag cagtttagac agag                                            24

<210> SEQ ID NO 11
<211> LENGTH: 26
<212> TYPE: DNA
<213> ORGANISM: artificial sequence
<220> FEATURE:
<223> OTHER INFORMATION: The forward primer for SNP of specific position
      (chr13:19722801)

<400> SEQUENCE: 11
agtaacatgt tccttgtttg ctctgt                                          26
```

<210> SEQ ID NO 12
<211> LENGTH: 22
<212> TYPE: DNA
<213> ORGANISM: artificial sequence
<220> FEATURE:
<223> OTHER INFORMATION: The reverse primer for SNP of specific position
     (chr13:19722801)

<400> SEQUENCE: 12
catggcagtg gttttgcaat tg                                              22

<210> SEQ ID NO 13
<211> LENGTH: 23
<212> TYPE: DNA
<213> ORGANISM: artificial sequence
<220> FEATURE:
<223> OTHER INFORMATION: The forward primer for SNP of specific position
     (chr13:19732341)

<400> SEQUENCE: 13
catcataggg tttgccagat ggt                                             23

<210> SEQ ID NO 14
<211> LENGTH: 26
<212> TYPE: DNA
<213> ORGANISM: artificial sequence
<220> FEATURE:
<223> OTHER INFORMATION: The reverse primer for SNP of specific position
     (chr13:19732341)

<400> SEQUENCE: 14
tggcagagtt aatgaatctg tgacag                                          26

<210> SEQ ID NO 15
<211> LENGTH: 23
<212> TYPE: DNA
<213> ORGANISM: artificial sequence
<220> FEATURE:
<223> OTHER INFORMATION: The forward primer for SNP of specific position
     (chr13:19784913)

<400> SEQUENCE: 15
caaaagtgag tgcttggaaa gct                                             23

<210> SEQ ID NO 16
<211> LENGTH: 30
<212> TYPE: DNA
<213> ORGANISM: artificial sequence
<220> FEATURE:
<223> OTHER INFORMATION: The reverse primer for SNP of specific position
     (chr13:19784913)

<400> SEQUENCE: 16
tgcaattcta tcaatggcat acaatgtaaa                                      30

<210> SEQ ID NO 17
<211> LENGTH: 23
<212> TYPE: DNA
<213> ORGANISM: artificial sequence
<220> FEATURE:
<223> OTHER INFORMATION: The forward primer for SNP of specific position
     (chr13:19843135)

<400> SEQUENCE: 17
gaagaaggtg agagattgcc tga                                             23

```
<210> SEQ ID NO 18
<211> LENGTH: 24
<212> TYPE: DNA
<213> ORGANISM: artificial sequence
<220> FEATURE:
<223> OTHER INFORMATION: The reverse primer for SNP of specific position
      (chr13:19843135)

<400> SEQUENCE: 18
caacagagtg agttgcgttt cttc                                           24

<210> SEQ ID NO 19
<211> LENGTH: 24
<212> TYPE: DNA
<213> ORGANISM: artificial sequence
<220> FEATURE:
<223> OTHER INFORMATION: The forward primer for SNP of specific position
      (chr13:19877547)

<400> SEQUENCE: 19
actctacaga gcatagactg ctca                                           24

<210> SEQ ID NO 20
<211> LENGTH: 30
<212> TYPE: DNA
<213> ORGANISM: artificial sequence
<220> FEATURE:
<223> OTHER INFORMATION: The reverse primer for SNP of specific position
      (chr13:19877547)

<400> SEQUENCE: 20
tgttagtcat agtgttagat ctccatgtga                                     30

<210> SEQ ID NO 21
<211> LENGTH: 27
<212> TYPE: DNA
<213> ORGANISM: artificial sequence
<220> FEATURE:
<223> OTHER INFORMATION: The forward primer for SNP of specific position
      (chr13:19883672)

<400> SEQUENCE: 21
ggaaggtggg ataataagga aaacagt                                        27

<210> SEQ ID NO 22
<211> LENGTH: 29
<212> TYPE: DNA
<213> ORGANISM: artificial sequence
<220> FEATURE:
<223> OTHER INFORMATION: The reverse primer for SNP of specific position
      (chr13:19883672)

<400> SEQUENCE: 22
ctgtattaat gtgtgcacac tttgcttag                                      29

<210> SEQ ID NO 23
<211> LENGTH: 30
<212> TYPE: DNA
<213> ORGANISM: artificial sequence
<220> FEATURE:
<223> OTHER INFORMATION: The forward primer for SNP of specific position
      (chr13:19896927)

<400> SEQUENCE: 23
gttcatcatc ataaaaacac actgaagtgt                                     30
```

```
<210> SEQ ID NO 24
<211> LENGTH: 30
<212> TYPE: DNA
<213> ORGANISM: artificial sequence
<220> FEATURE:
<223> OTHER INFORMATION: The reverse primer for SNP of specific position
      (chr13:19896927)

<400> SEQUENCE: 24
gcctcaggta atcctttata gcaagataag                                    30

<210> SEQ ID NO 25
<211> LENGTH: 30
<212> TYPE: DNA
<213> ORGANISM: artificial sequence
<220> FEATURE:
<223> OTHER INFORMATION: The forward primer for SNP of specific position
      (chr13:19917509)

<400> SEQUENCE: 25
tcatcaggat caggttctaa aatcttacac                                    30

<210> SEQ ID NO 26
<211> LENGTH: 30
<212> TYPE: DNA
<213> ORGANISM: artificial sequence
<220> FEATURE:
<223> OTHER INFORMATION: The reverse primer for SNP of specific position
      (chr13:19917509)

<400> SEQUENCE: 26
gcatcaaggt tttaagattt ctaggttacg                                    30

<210> SEQ ID NO 27
<211> LENGTH: 25
<212> TYPE: DNA
<213> ORGANISM: artificial sequence
<220> FEATURE:
<223> OTHER INFORMATION: The forward primer for SNP of specific position
      (chr13:20494558)

<400> SEQUENCE: 27
cctctaggac agagatggac aaact                                         25

<210> SEQ ID NO 28
<211> LENGTH: 25
<212> TYPE: DNA
<213> ORGANISM: artificial sequence
<220> FEATURE:
<223> OTHER INFORMATION: The reverse primer for SNP of specific position
      (chr13:20494558)

<400> SEQUENCE: 28
gatacaaaac tctgcctgct tacac                                         25

<210> SEQ ID NO 29
<211> LENGTH: 27
<212> TYPE: DNA
<213> ORGANISM: artificial sequence
<220> FEATURE:
<223> OTHER INFORMATION: The forward primer for SNP of specific position
      (chr13:20709214)

<400> SEQUENCE: 29
ccattttctg tctcttgctc taggtat                                       27

<210> SEQ ID NO 30
```

```
<211> LENGTH: 28
<212> TYPE: DNA
<213> ORGANISM: artificial sequence
<220> FEATURE:
<223> OTHER INFORMATION: The reverse primer for SNP of specific position
      (chr13:20709214)

<400> SEQUENCE: 30
ggaagatgga aaacttctgg aaaaggat                                            28

<210> SEQ ID NO 31
<211> LENGTH: 29
<212> TYPE: DNA
<213> ORGANISM: artificial sequence
<220> FEATURE:
<223> OTHER INFORMATION: The forward primer for SNP of specific position
      (chr13:20747500)

<400> SEQUENCE: 31
cagtatcaac agaaaacaag ctgattcaa                                           29

<210> SEQ ID NO 32
<211> LENGTH: 29
<212> TYPE: DNA
<213> ORGANISM: artificial sequence
<220> FEATURE:
<223> OTHER INFORMATION: The reverse primer for SNP of specific position
      (chr13:20747500)

<400> SEQUENCE: 32
ctgcaactat accattttac atttccact                                           29

<210> SEQ ID NO 33
<211> LENGTH: 23
<212> TYPE: DNA
<213> ORGANISM: artificial sequence
<220> FEATURE:
<223> OTHER INFORMATION: The forward primer for SNP of specific position
      (chr13:20784332)

<400> SEQUENCE: 33
ctgccatctg aatggtttca agg                                                 23

<210> SEQ ID NO 34
<211> LENGTH: 24
<212> TYPE: DNA
<213> ORGANISM: artificial sequence
<220> FEATURE:
<223> OTHER INFORMATION: The reverse primer for SNP of specific position
      (chr13:20784332)

<400> SEQUENCE: 34 cttttctcc tgactttgtg gcat                                                 24

<210> SEQ ID NO 35
<211> LENGTH: 27
<212> TYPE: DNA
<213> ORGANISM: artificial sequence
<220> FEATURE:
<223> OTHER INFORMATION: The forward primer for SNP of specific position
      (chr13:20825315)

<400> SEQUENCE: 35
gttatgtatt tgtgatgcat tggcctt                                             27

<210> SEQ ID NO 36
<211> LENGTH: 29
```

```
<212> TYPE: DNA
<213> ORGANISM: artificial sequence
<220> FEATURE:
<223> OTHER INFORMATION: The reverse primer for SNP of specific position
      (chr13:20825315)

<400> SEQUENCE: 36
ctttaactga aggcaaaaat tagcagact                                          29

<210> SEQ ID NO 37
<211> LENGTH: 30
<212> TYPE: DNA
<213> ORGANISM: artificial sequence
<220> FEATURE:
<223> OTHER INFORMATION: The forward primer for SNP of specific position
      (chr13:20864572)

<400> SEQUENCE: 37
cagttactta gaacagcaag atactgaaca                                         30

<210> SEQ ID NO 38
<211> LENGTH: 23
<212> TYPE: DNA
<213> ORGANISM: artificial sequence
<220> FEATURE:
<223> OTHER INFORMATION: The reverse primer for SNP of specific position
      (chr13:20864572)

<400> SEQUENCE: 38
aagtgcatga cttagagcca caa                                                23

<210> SEQ ID NO 39
<211> LENGTH: 22
<212> TYPE: DNA
<213> ORGANISM: artificial sequence
<220> FEATURE:
<223> OTHER INFORMATION: The forward primer for SNP of specific position
      (chr13:20881859)

<400> SEQUENCE: 39
ccaagtgaat ggtggtctca ct                                                 22

<210> SEQ ID NO 40
<211> LENGTH: 23
<212> TYPE: DNA
<213> ORGANISM: artificial sequence
<220> FEATURE:
<223> OTHER INFORMATION: The reverse primer for SNP of specific position
      (chr13:20881859)

<400> SEQUENCE: 40
atctccaaac atctgccaac act                                                23

<210> SEQ ID NO 41
<211> LENGTH: 24
<212> TYPE: DNA
<213> ORGANISM: artificial sequence
<220> FEATURE:
<223> OTHER INFORMATION: The forward primer for SNP of specific position
      (chr13:20908501)

<400> SEQUENCE: 41
gtacacacac tgcatctcgt atgt                                               24

<210> SEQ ID NO 42
<211> LENGTH: 22
<212> TYPE: DNA
```

<213> ORGANISM: artificial sequence
<220> FEATURE:
<223> OTHER INFORMATION: The reverse primer for SNP of specific position
      (chr13:20908501)

<400> SEQUENCE: 42
ggcaccagga tagtcactgt ag                                        22

<210> SEQ ID NO 43
<211> LENGTH: 24
<212> TYPE: DNA
<213> ORGANISM: artificial sequence
<220> FEATURE:
<223> OTHER INFORMATION: The forward primer for SNP of specific position
      (chr13:20938952)

<400> SEQUENCE: 43
ggtgtctgta tccactccaa ttcc                                      24

<210> SEQ ID NO 44
<211> LENGTH: 24
<212> TYPE: DNA
<213> ORGANISM: artificial sequence
<220> FEATURE:
<223> OTHER INFORMATION: The reverse primer for SNP of specific position
      (chr13:20938952)

<400> SEQUENCE: 44
gtgctcttga tctaactgga gctt                                      24

<210> SEQ ID NO 45
<211> LENGTH: 25
<212> TYPE: DNA
<213> ORGANISM: artificial sequence
<220> FEATURE:
<223> OTHER INFORMATION: The forward primer for SNP of specific position
      (chr13:20951425)

<400> SEQUENCE: 45
aaagcaaaac aaccatgcac catta                                     25

<210> SEQ ID NO 46
<211> LENGTH: 22
<212> TYPE: DNA
<213> ORGANISM: artificial sequence
<220> FEATURE:
<223> OTHER INFORMATION: The reverse primer for SNP of specific position
      (chr13:20951425)

<400> SEQUENCE: 46
gggaaaagca tcccatcttt cc                                        22

<210> SEQ ID NO 47
<211> LENGTH: 23
<212> TYPE: DNA
<213> ORGANISM: artificial sequence
<220> FEATURE:
<223> OTHER INFORMATION: The forward primer for SNP of specific position
      (chr13:20992333)

<400> SEQUENCE: 47
tcctcaggga gatctcagtt ctg                                       23

<210> SEQ ID NO 48
<211> LENGTH: 27
<212> TYPE: DNA
<213> ORGANISM: artificial sequence

```
<220> FEATURE:
<223> OTHER INFORMATION: The reverse primer for SNP of specific position
      (chr13:20992333)

<400> SEQUENCE: 48
gttagatgtg tcttgcttcc tcttctc                                        27

<210> SEQ ID NO 49
<211> LENGTH: 24
<212> TYPE: DNA
<213> ORGANISM: artificial sequence
<220> FEATURE:
<223> OTHER INFORMATION: The forward primer for SNP of specific position
      (chr13:21012562)

<400> SEQUENCE: 49
catctacaga tccggtagga gtct                                           24

<210> SEQ ID NO 50
<211> LENGTH: 24
<212> TYPE: DNA
<213> ORGANISM: artificial sequence
<220> FEATURE:
<223> OTHER INFORMATION: The reverse primer for SNP of specific position
      (chr13:21012562)

<400> SEQUENCE: 50
ggagaatcgt gagggttact ctga                                           24

<210> SEQ ID NO 51
<211> LENGTH: 24
<212> TYPE: DNA
<213> ORGANISM: artificial sequence
<220> FEATURE:
<223> OTHER INFORMATION: The forward primer for SNP of specific position
      (chr13:21066214)

<400> SEQUENCE: 51
accaaatatg tgtcttggcc agtt                                           24

<210> SEQ ID NO 52
<211> LENGTH: 22
<212> TYPE: DNA
<213> ORGANISM: artificial sequence
<220> FEATURE:
<223> OTHER INFORMATION: The reverse primer for SNP of specific position
      (chr13:21066214)

<400> SEQUENCE: 52
gagtgctgtt gatgctgaat cg                                             22

<210> SEQ ID NO 53
<211> LENGTH: 23
<212> TYPE: DNA
<213> ORGANISM: artificial sequence
<220> FEATURE:
<223> OTHER INFORMATION: The forward primer for SNP of specific position
      (chr13:21092894)

<400> SEQUENCE: 53
cagaagcaat ggagggattt tgg                                            23

<210> SEQ ID NO 54
<211> LENGTH: 30
<212> TYPE: DNA
<213> ORGANISM: artificial sequence
<220> FEATURE:
```

<223> OTHER INFORMATION: The reverse primer for SNP of specific position
      (chr13:21092894)

<400> SEQUENCE: 54
gtactgtgaa aatactgcac attcatttct                                          30

<210> SEQ ID NO 55
<211> LENGTH: 23
<212> TYPE: DNA
<213> ORGANISM: artificial sequence
<220> FEATURE:
<223> OTHER INFORMATION: The forward primer for SNP of specific position
      (chr13:21112935)

<400> SEQUENCE: 55
gcctggtgac agagtatgat gac                                                 23

<210> SEQ ID NO 56
<211> LENGTH: 22
<212> TYPE: DNA
<213> ORGANISM: artificial sequence
<220> FEATURE:
<223> OTHER INFORMATION: The reverse primer for SNP of specific position
      (chr13:21112935)

<400> SEQUENCE: 56
gaggtcacag caatgtcagg aa                                                  22

<210> SEQ ID NO 57
<211> LENGTH: 23
<212> TYPE: DNA
<213> ORGANISM: artificial sequence
<220> FEATURE:
<223> OTHER INFORMATION: The forward primer for SNP of specific position
      (chr13:21527671)

<400> SEQUENCE: 57
gcaccaaaca aggacacata gtg                                                 23

<210> SEQ ID NO 58
<211> LENGTH: 30
<212> TYPE: DNA
<213> ORGANISM: artificial sequence
<220> FEATURE:
<223> OTHER INFORMATION: The reverse primer for SNP of specific position
      (chr13:21527671)

<400> SEQUENCE: 58
tttttcctta atctacccaa ataccaggta                                          30

<210> SEQ ID NO 59
<211> LENGTH: 25
<212> TYPE: DNA
<213> ORGANISM: artificial sequence
<220> FEATURE:
<223> OTHER INFORMATION: The forward primer for SNP of specific position
      (chr13:21553971)

<400> SEQUENCE: 59
aatgctgacc aaagattcat gggta                                               25

<210> SEQ ID NO 60
<211> LENGTH: 30
<212> TYPE: DNA
<213> ORGANISM: artificial sequence
<220> FEATURE:
<223> OTHER INFORMATION: The reverse primer for SNP of specific position (chr13:21553971)

<400> SEQUENCE: 60
aggaaatctg tatgttcagc atcttaatga                              30

<210> SEQ ID NO 61
<211> LENGTH: 27
<212> TYPE: DNA
<213> ORGANISM: artificial sequence
<220> FEATURE:
<223> OTHER INFORMATION: The forward primer for SNP of specific position
      (chr13:21575458)

<400> SEQUENCE: 61
ttttgtcaca atggagatag gtgaaca                                 27

<210> SEQ ID NO 62
<211> LENGTH: 29
<212> TYPE: DNA
<213> ORGANISM: artificial sequence
<220> FEATURE:
<223> OTHER INFORMATION: The reverse primer for SNP of specific position
      (chr13:21575458)

<400> SEQUENCE: 62
ctcattccat tgatagagaa aatcacagg                               29

<210> SEQ ID NO 63
<211> LENGTH: 23
<212> TYPE: DNA
<213> ORGANISM: artificial sequence
<220> FEATURE:
<223> OTHER INFORMATION: The forward primer for SNP of specific position
      (chr13:21607760)

<400> SEQUENCE: 63
gtgacctcag acagagaggt aga                                     23

<210> SEQ ID NO 64
<211> LENGTH: 28
<212> TYPE: DNA
<213> ORGANISM: artificial sequence
<220> FEATURE:
<223> OTHER INFORMATION: The reverse primer for SNP of specific position
      (chr13:21607760)

<400> SEQUENCE: 64
aagtgtagtg gaacaaattg tactctgt                                28

<210> SEQ ID NO 65
<211> LENGTH: 22
<212> TYPE: DNA
<213> ORGANISM: artificial sequence
<220> FEATURE:
<223> OTHER INFORMATION: The forward primer for SNP of specific position
      (chr13:21636136)

<400> SEQUENCE: 65
gcctctcgga cctatttgac tg                                      22

<210> SEQ ID NO 66
<211> LENGTH: 25
<212> TYPE: DNA
<213> ORGANISM: artificial sequence
<220> FEATURE:
<223> OTHER INFORMATION: The reverse primer for SNP of specific position
      (chr13:21636136)

```
<400> SEQUENCE: 66
gcttctggca aacgtccttc ttaat                                           25

<210> SEQ ID NO 67
<211> LENGTH: 30
<212> TYPE: DNA
<213> ORGANISM: artificial sequence
<220> FEATURE:
<223> OTHER INFORMATION: The forward primer for SNP of specific position
      (chr13:21655335)

<400> SEQUENCE: 67
tttgaagaca aattaccact taaggttgtg                                      30

<210> SEQ ID NO 68
<211> LENGTH: 24
<212> TYPE: DNA
<213> ORGANISM: artificial sequence
<220> FEATURE:
<223> OTHER INFORMATION: The reverse primer for SNP of specific position
      (chr13:21655335)

<400> SEQUENCE: 68
gtgatgatga agcctttccc ttca                                            24

<210> SEQ ID NO 69
<211> LENGTH: 26
<212> TYPE: DNA
<213> ORGANISM: artificial sequence
<220> FEATURE:
<223> OTHER INFORMATION: The forward primer for SNP of specific position
      (chr13:21683681)

<400> SEQUENCE: 69
gtgtctgttt tctgagtcct tcttgt                                          26

<210> SEQ ID NO 70
<211> LENGTH: 28
<212> TYPE: DNA
<213> ORGANISM: artificial sequence
<220> FEATURE:
<223> OTHER INFORMATION: The reverse primer for SNP of specific position
      (chr13:21683681)

<400> SEQUENCE: 70
ctcagactag ataaaggctg gtagaaac                                        28

<210> SEQ ID NO 71
<211> LENGTH: 23
<212> TYPE: DNA
<213> ORGANISM: artificial sequence
<220> FEATURE:
<223> OTHER INFORMATION: The forward primer for SNP of specific position
      (chr13:21801501)

<400> SEQUENCE: 71
ctcagaatct cttggctgtg aca                                             23

<210> SEQ ID NO 72
<211> LENGTH: 22
<212> TYPE: DNA
<213> ORGANISM: artificial sequence
<220> FEATURE:
<223> OTHER INFORMATION: The reverse primer for SNP of specific position
      (chr13:21801501)
```

<400> SEQUENCE: 72
tgaagccatg ctgatagcat gt                                            22

<210> SEQ ID NO 73
<211> LENGTH: 22
<212> TYPE: DNA
<213> ORGANISM: artificial sequence
<220> FEATURE:
<223> OTHER INFORMATION: The forward primer for SNP of specific position
      (chr13:22197910)

<400> SEQUENCE: 73
ggcagccatt gaactggaaa aa                                            22

<210> SEQ ID NO 74
<211> LENGTH: 25
<212> TYPE: DNA
<213> ORGANISM: artificial sequence
<220> FEATURE:
<223> OTHER INFORMATION: The reverse primer for SNP of specific position
      (chr13:22197910)

<400> SEQUENCE: 74
caacatggaa acctctcaca ttcag                                         25

<210> SEQ ID NO 75
<211> LENGTH: 28
<212> TYPE: DNA
<213> ORGANISM: artificial sequence
<220> FEATURE:
<223> OTHER INFORMATION: The forward primer for SNP of specific position
      (chr13:22249975)

<400> SEQUENCE: 75
tcctcacact cagtttctct agaaaaga                                      28

<210> SEQ ID NO 76
<211> LENGTH: 22
<212> TYPE: DNA
<213> ORGANISM: artificial sequence
<220> FEATURE:
<223> OTHER INFORMATION: The reverse primer for SNP of specific position
      (chr13:22249975)

<400> SEQUENCE: 76
tcccacctaa gttgtcacct ct                                            22

<210> SEQ ID NO 77
<211> LENGTH: 30
<212> TYPE: DNA
<213> ORGANISM: artificial sequence
<220> FEATURE:
<223> OTHER INFORMATION: The forward primer for SNP of specific position
      (chr13:22270788)

<400> SEQUENCE: 77
gtatagttta tttgaaggca gacactcctt                                    30

<210> SEQ ID NO 78
<211> LENGTH: 27
<212> TYPE: DNA
<213> ORGANISM: artificial sequence
<220> FEATURE:
<223> OTHER INFORMATION: The reverse primer for SNP of specific position
      (chr13:22270788)

<400> SEQUENCE: 78
gccaatgtgt gatttttgtt ttagacg                                               27

<210> SEQ ID NO 79
<211> LENGTH: 29
<212> TYPE: DNA
<213> ORGANISM: artificial sequence
<220> FEATURE:
<223> OTHER INFORMATION: The forward primer for SNP of specific position
      (chr13:22340074)

<400> SEQUENCE: 79
atcagtgagt gcttaaacta ttggatcaa                                             29

<210> SEQ ID NO 80
<211> LENGTH: 28
<212> TYPE: DNA
<213> ORGANISM: artificial sequence
<220> FEATURE:
<223> OTHER INFORMATION: The reverse primer for SNP of specific position
      (chr13:22340074)

<400> SEQUENCE: 80
gaattagatt caggctatgc atttcagg                                              28

<210> SEQ ID NO 81
<211> LENGTH: 24
<212> TYPE: DNA
<213> ORGANISM: artificial sequence
<220> FEATURE:
<223> OTHER INFORMATION: The forward primer for SNP of specific position
      (chr13:22396664)

<400> SEQUENCE: 81
taccaaacat agcgtggacc tttt                                                  24

<210> SEQ ID NO 82
<211> LENGTH: 22
<212> TYPE: DNA
<213> ORGANISM: artificial sequence
<220> FEATURE:
<223> OTHER INFORMATION: The reverse primer for SNP of specific position
      (chr13:22396664)

<400> SEQUENCE: 82
gaatggcaac ggagttgttt cc                                                    22

<210> SEQ ID NO 83
<211> LENGTH: 29
<212> TYPE: DNA
<213> ORGANISM: artificial sequence
<220> FEATURE:
<223> OTHER INFORMATION: The forward primer for SNP of specific position
      (chr13:22417688)

<400> SEQUENCE: 83
acagatttta ttcgaatatc cggttggat                                             29

<210> SEQ ID NO 84
<211> LENGTH: 22
<212> TYPE: DNA
<213> ORGANISM: artificial sequence
<220> FEATURE:
<223> OTHER INFORMATION: The reverse primer for SNP of specific position
      (chr13:22417688)

<400> SEQUENCE: 84
catttgccag gatttctgct ca                                          22

<210> SEQ ID NO 85
<211> LENGTH: 22
<212> TYPE: DNA
<213> ORGANISM: artificial sequence
<220> FEATURE:
<223> OTHER INFORMATION: The forward primer for SNP of specific position
      (chr13:22473749)

<400> SEQUENCE: 85
gtagggctca gtgctttctg tt                                          22

<210> SEQ ID NO 86
<211> LENGTH: 23
<212> TYPE: DNA
<213> ORGANISM: artificial sequence
<220> FEATURE:
<223> OTHER INFORMATION: The reverse primer for SNP of specific position
      (chr13:22473749)

<400> SEQUENCE: 86
gcatcctctg tttgagctaa ggt                                         23

<210> SEQ ID NO 87
<211> LENGTH: 29
<212> TYPE: DNA
<213> ORGANISM: artificial sequence
<220> FEATURE:
<223> OTHER INFORMATION: The forward primer for SNP of specific position
      (chr13:22504691)

<400> SEQUENCE: 87
catttattta acaagggaca cagaccaaa                                   29

<210> SEQ ID NO 88
<211> LENGTH: 22
<212> TYPE: DNA
<213> ORGANISM: artificial sequence
<220> FEATURE:
<223> OTHER INFORMATION: The reverse primer for SNP of specific position
      (chr13:22504691)

<400> SEQUENCE: 88
taactccgca gtccttagac ca                                          22

<210> SEQ ID NO 89
<211> LENGTH: 24
<212> TYPE: DNA
<213> ORGANISM: artificial sequence
<220> FEATURE:
<223> OTHER INFORMATION: The forward primer for SNP of specific position
      (chr13:22515844)

<400> SEQUENCE: 89
accatggcat ggtcactaaa aact                                        24

<210> SEQ ID NO 90
<211> LENGTH: 21
<212> TYPE: DNA
<213> ORGANISM: artificial sequence
<220> FEATURE:
<223> OTHER INFORMATION: The reverse primer for SNP of specific position
      (chr13:22515844)

<400> SEQUENCE: 90
gggtcgctct ggtgtataag c                                           21

<210> SEQ ID NO 91
<211> LENGTH: 24
<212> TYPE: DNA
<213> ORGANISM: artificial sequence
<220> FEATURE:
<223> OTHER INFORMATION: The forward primer for SNP of specific position
      (chr13:22523279)

<400> SEQUENCE: 91
tttgcaaaga cttcctgctg aatg                                          24

<210> SEQ ID NO 92
<211> LENGTH: 30
<212> TYPE: DNA
<213> ORGANISM: artificial sequence
<220> FEATURE:
<223> OTHER INFORMATION: The reverse primer for SNP of specific position
      (chr13:22523279)

<400> SEQUENCE: 92
cctccaaaaa tagtcagtag ttcctacaat                                    30

<210> SEQ ID NO 93
<211> LENGTH: 28
<212> TYPE: DNA
<213> ORGANISM: artificial sequence
<220> FEATURE:
<223> OTHER INFORMATION: The forward primer for SNP of specific position
      (chr13:22538311)

<400> SEQUENCE: 93
ccttggactt ttagcttcta gaactgta                                      28

<210> SEQ ID NO 94
<211> LENGTH: 30
<212> TYPE: DNA
<213> ORGANISM: artificial sequence
<220> FEATURE:
<223> OTHER INFORMATION: The reverse primer for SNP of specific position
      (chr13:22538311)

<400> SEQUENCE: 94
attgcctgat ataccgcagt ttatttatct                                    30

<210> SEQ ID NO 95
<211> LENGTH: 25
<212> TYPE: DNA
<213> ORGANISM: artificial sequence
<220> FEATURE:
<223> OTHER INFORMATION: The forward primer for SNP of specific position
      (chr13:22561684)

<400> SEQUENCE: 95
cccaaaaatc taaagccatc acctt                                         25

<210> SEQ ID NO 96
<211> LENGTH: 30
<212> TYPE: DNA
<213> ORGANISM: artificial sequence
<220> FEATURE:
<223> OTHER INFORMATION: The reverse primer for SNP of specific position
      (chr13:22561684)

<400> SEQUENCE: 96
acatcatatg acgtaaaaat tcctacagca                                    30

<210> SEQ ID NO 97
<211> LENGTH: 24
<212> TYPE: DNA
<213> ORGANISM: artificial sequence
<220> FEATURE:
<223> OTHER INFORMATION: The forward primer for SNP of specific position
      (chr13:22640820)

<400> SEQUENCE: 97
caccagcatt agtttaggca aaca                                          24

<210> SEQ ID NO 98
<211> LENGTH: 24
<212> TYPE: DNA
<213> ORGANISM: artificial sequence
<220> FEATURE:
<223> OTHER INFORMATION: The reverse primer for SNP of specific position
      (chr13:22640820)

<400> SEQUENCE: 98
taacgaaact gtgcacttgt tcct                                          24

<210> SEQ ID NO 99
<211> LENGTH: 29
<212> TYPE: DNA
<213> ORGANISM: artificial sequence
<220> FEATURE:
<223> OTHER INFORMATION: The forward primer for SNP of specific position
      (chr13:22751654)

<400> SEQUENCE: 99
ttaaagaggt agaatctgta ggacttggt                                     29

<210> SEQ ID NO 100
<211> LENGTH: 22
<212> TYPE: DNA
<213> ORGANISM: artificial sequence
<220> FEATURE:
<223> OTHER INFORMATION: The reverse primer for SNP of specific position
      (chr13:22751654)

<400> SEQUENCE: 100
tggatgttgg ttccctacct ct                                            22

<210> SEQ ID NO 101
<211> LENGTH: 25
<212> TYPE: DNA
<213> ORGANISM: artificial sequence
<220> FEATURE:
<223> OTHER INFORMATION: The forward primer for SNP of specific position
      (chr13:22768476)

<400> SEQUENCE: 101
ttctgtgttg caagtgacag aaaac                                         25

<210> SEQ ID NO 102
<211> LENGTH: 25
<212> TYPE: DNA
<213> ORGANISM: artificial sequence
<220> FEATURE:
<223> OTHER INFORMATION: The reverse primer for SNP of specific position
      (chr13:22768476)

<400> SEQUENCE: 102
ttgctgctga caacaaagat gtttt                                         25

```
<210> SEQ ID NO 103
<211> LENGTH: 28
<212> TYPE: DNA
<213> ORGANISM: artificial sequence
<220> FEATURE:
<223> OTHER INFORMATION: The forward primer for SNP of specific position
      (chr13:22780737)

<400> SEQUENCE: 103
acagtaggtt aaacaggata ggaaaacg                                          28

<210> SEQ ID NO 104
<211> LENGTH: 27
<212> TYPE: DNA
<213> ORGANISM: artificial sequence
<220> FEATURE:
<223> OTHER INFORMATION: The reverse primer for SNP of specific position
      (chr13:22780737)

<400> SEQUENCE: 104
tgagatttaa gtgcaaatgg atgcaac                                           27

<210> SEQ ID NO 105
<211> LENGTH: 23
<212> TYPE: DNA
<213> ORGANISM: artificial sequence
<220> FEATURE:
<223> OTHER INFORMATION: The forward primer for SNP of specific position
      (chr13:22799808)

<400> SEQUENCE: 105
gaaaactggt cagaggcagc taa                                               23

<210> SEQ ID NO 106
<211> LENGTH: 28
<212> TYPE: DNA
<213> ORGANISM: artificial sequence
<220> FEATURE:
<223> OTHER INFORMATION: The reverse primer for SNP of specific position
      (chr13:22799808)

<400> SEQUENCE: 106
agaggatgat tccctatacc tctgagta                                          28

<210> SEQ ID NO 107
<211> LENGTH: 27
<212> TYPE: DNA
<213> ORGANISM: artificial sequence
<220> FEATURE:
<223> OTHER INFORMATION: The forward primer for SNP of specific position
      (chr13:22819627)

<400> SEQUENCE: 107
gaatgtaggg accaaattcc atagaca                                           27

<210> SEQ ID NO 108
<211> LENGTH: 29
<212> TYPE: DNA
<213> ORGANISM: artificial sequence
<220> FEATURE:
<223> OTHER INFORMATION: The reverse primer for SNP of specific position
      (chr13:22819627)

<400> SEQUENCE: 108
acagacagac agacagatag tatatgtgt                                         29

<210> SEQ ID NO 109
```

```
<211> LENGTH: 27
<212> TYPE: DNA
<213> ORGANISM: artificial sequence
<220> FEATURE:
<223> OTHER INFORMATION: The forward primer for SNP of specific position
      (chr13:22835073)

<400> SEQUENCE: 109
cttaatgcag atgaggaact aatgcac                                           27

<210> SEQ ID NO 110
<211> LENGTH: 30
<212> TYPE: DNA
<213> ORGANISM: artificial sequence
<220> FEATURE:
<223> OTHER INFORMATION: The reverse primer for SNP of specific position
      (chr13:22835073)

<400> SEQUENCE: 110
tcatgaaacc actgtttgga taatcatcat                                        30

<210> SEQ ID NO 111
<211> LENGTH: 24
<212> TYPE: DNA
<213> ORGANISM: artificial sequence
<220> FEATURE:
<223> OTHER INFORMATION: The forward primer for SNP of specific position
      (chr13:22892864)

<400> SEQUENCE: 111
gcttaatgca gtgggtccta aact                                              24

<210> SEQ ID NO 112
<211> LENGTH: 30
<212> TYPE: DNA
<213> ORGANISM: artificial sequence
<220> FEATURE:
<223> OTHER INFORMATION: The reverse primer for SNP of specific position
      (chr13:22892864)

<400> SEQUENCE: 112
cactgtaaca ctttaaatgg gtgaattgtt                                        30

<210> SEQ ID NO 113
<211> LENGTH: 22
<212> TYPE: DNA
<213> ORGANISM: artificial sequence
<220> FEATURE:
<223> OTHER INFORMATION: The forward primer for SNP of specific position
      (chr13:22980146)

<400> SEQUENCE: 113
ctcagttgca gagccacaga ct                                                22

<210> SEQ ID NO 114
<211> LENGTH: 28
<212> TYPE: DNA
<213> ORGANISM: artificial sequence
<220> FEATURE:
<223> OTHER INFORMATION: The reverse primer for SNP of specific position
      (chr13:22980146)

<400> SEQUENCE: 114
ggtgtgccag aatctaagag aaattctc                                          28

<210> SEQ ID NO 115
<211> LENGTH: 30
```

```
<212> TYPE: DNA
<213> ORGANISM: artificial sequence
<220> FEATURE:
<223> OTHER INFORMATION: The forward primer for SNP of specific position
      (chr14:19472367)

<400> SEQUENCE: 115
tgatttgatg ttctaaccag cactaaaact                                        30

<210> SEQ ID NO 116
<211> LENGTH: 25
<212> TYPE: DNA
<213> ORGANISM: artificial sequence
<220> FEATURE:
<223> OTHER INFORMATION: The reverse primer for SNP of specific position
      (chr14:19472367)

<400> SEQUENCE: 116
gccctataca tgttcaggtg gaaag                                             25

<210> SEQ ID NO 117
<211> LENGTH: 20
<212> TYPE: DNA
<213> ORGANISM: artificial sequence
<220> FEATURE:
<223> OTHER INFORMATION: The forward primer for SNP of specific position
      (chr14:20326905)

<400> SEQUENCE: 117
gggcctttcc caaatgctat                                                   20

<210> SEQ ID NO 118
<211> LENGTH: 32
<212> TYPE: DNA
<213> ORGANISM: artificial sequence
<220> FEATURE:
<223> OTHER INFORMATION: The reverse primer for SNP of specific position
      (chr14:20326905)

<400> SEQUENCE: 118
gggatataaa ggtattcaat aaaggatagc at                                     32

<210> SEQ ID NO 119
<211> LENGTH: 28
<212> TYPE: DNA
<213> ORGANISM: artificial sequence
<220> FEATURE:
<223> OTHER INFORMATION: The forward primer for SNP of specific position
      (chr14:20349694)

<400> SEQUENCE: 119
tcttggttac accatgaggt aaatatgc                                          28

<210> SEQ ID NO 120
<211> LENGTH: 30
<212> TYPE: DNA
<213> ORGANISM: artificial sequence
<220> FEATURE:
<223> OTHER INFORMATION: The reverse primer for SNP of specific position
      (chr14:20349694)

<400> SEQUENCE: 120
taggtattca tctccttata ttggcagtgt                                        30

<210> SEQ ID NO 121
<211> LENGTH: 27
<212> TYPE: DNA
```

```
<213> ORGANISM: artificial sequence
<220> FEATURE:
<223> OTHER INFORMATION: The forward primer for SNP of specific position
      (chr14:20383719)

<400> SEQUENCE: 121
gtcattcttt ttgcattagc tggttga                                          27

<210> SEQ ID NO 122
<211> LENGTH: 29
<212> TYPE: DNA
<213> ORGANISM: artificial sequence
<220> FEATURE:
<223> OTHER INFORMATION: The reverse primer for SNP of specific position
      (chr14:20383719)

<400> SEQUENCE: 122
atgccaaaag tactttgtcc ataaatgtg                                        29

<210> SEQ ID NO 123
<211> LENGTH: 27
<212> TYPE: DNA
<213> ORGANISM: artificial sequence
<220> FEATURE:
<223> OTHER INFORMATION: The forward primer for SNP of specific position
      (chr14:20420387)

<400> SEQUENCE: 123
cttttcatgt ctgacatctg taccact                                          27

<210> SEQ ID NO 124
<211> LENGTH: 28
<212> TYPE: DNA
<213> ORGANISM: artificial sequence
<220> FEATURE:
<223> OTHER INFORMATION: The reverse primer for SNP of specific position
      (chr14:20420387)

<400> SEQUENCE: 124
tgcctaaggt aatgataaac cgaatgtg                                         28

<210> SEQ ID NO 125
<211> LENGTH: 24
<212> TYPE: DNA
<213> ORGANISM: artificial sequence
<220> FEATURE:
<223> OTHER INFORMATION: The forward primer for SNP of specific position
      (chr14:20517369)

<400> SEQUENCE: 125
caggactggg agagaaatag gaga                                             24

<210> SEQ ID NO 126
<211> LENGTH: 30
<212> TYPE: DNA
<213> ORGANISM: artificial sequence
<220> FEATURE:
<223> OTHER INFORMATION: The reverse primer for SNP of specific position
      (chr14:20517369)

<400> SEQUENCE: 126
gatatttgca tcagaatcag atgcttttgt                                       30

<210> SEQ ID NO 127
<211> LENGTH: 28
<212> TYPE: DNA
<213> ORGANISM: artificial sequence
```

```
<220> FEATURE:
<223> OTHER INFORMATION: The forward primer for SNP of specific position
      (chr14:20527044)

<400> SEQUENCE: 127
gctatgggtt ttgacaaatg tgttatgt                                              28

<210> SEQ ID NO 128
<211> LENGTH: 27
<212> TYPE: DNA
<213> ORGANISM: artificial sequence
<220> FEATURE:
<223> OTHER INFORMATION: The reverse primer for SNP of specific position
      (chr14:20527044)

<400> SEQUENCE: 128
atagctttgc aatagcctct aagtgtt                                               27

<210> SEQ ID NO 129
<211> LENGTH: 30
<212> TYPE: DNA
<213> ORGANISM: artificial sequence
<220> FEATURE:
<223> OTHER INFORMATION: The forward primer for SNP of specific position
      (chr14:20565487)

<400> SEQUENCE: 129
gttgttgttg tttgttggtt tagattacca                                            30

<210> SEQ ID NO 130
<211> LENGTH: 29
<212> TYPE: DNA
<213> ORGANISM: artificial sequence
<220> FEATURE:
<223> OTHER INFORMATION: The reverse primer for SNP of specific position
      (chr14:20565487)

<400> SEQUENCE: 130
acttgaaaag aggctaatgt tagtgaact                                             29

<210> SEQ ID NO 131
<211> LENGTH: 22
<212> TYPE: DNA
<213> ORGANISM: artificial sequence
<220> FEATURE:
<223> OTHER INFORMATION: The forward primer for SNP of specific position
      (chr14:20643775)

<400> SEQUENCE: 131
cgtgttcaca ttgccctcta ca                                                    22

<210> SEQ ID NO 132
<211> LENGTH: 23
<212> TYPE: DNA
<213> ORGANISM: artificial sequence
<220> FEATURE:
<223> OTHER INFORMATION: The reverse primer for SNP of specific position
      (chr14:20643775)

<400> SEQUENCE: 132
aaacacctca aggcagaatg act                                                   23

<210> SEQ ID NO 133
<211> LENGTH: 23
<212> TYPE: DNA
<213> ORGANISM: artificial sequence
<220> FEATURE:
```

```
<223> OTHER INFORMATION: The forward primer for SNP of specific position
      (chr14:20670979)

<400> SEQUENCE: 133
gcttcgatct accatcttgc tgt                                              23

<210> SEQ ID NO 134
<211> LENGTH: 24
<212> TYPE: DNA
<213> ORGANISM: artificial sequence
<220> FEATURE:
<223> OTHER INFORMATION: The reverse primer for SNP of specific position
      (chr14:20670979)

<400> SEQUENCE: 134
agaccattag agcaccagct tttt                                             24

<210> SEQ ID NO 135
<211> LENGTH: 22
<212> TYPE: DNA
<213> ORGANISM: artificial sequence
<220> FEATURE:
<223> OTHER INFORMATION: The forward primer for SNP of specific position
      (chr14:20731036)

<400> SEQUENCE: 135
ctgccatggt tgattagcag ga                                               22

<210> SEQ ID NO 136
<211> LENGTH: 28
<212> TYPE: DNA
<213> ORGANISM: artificial sequence
<220> FEATURE:
<223> OTHER INFORMATION: The reverse primer for SNP of specific position
      (chr14:20731036)

<400> SEQUENCE: 136
gagatctatt cgcttgagat aggaagtg                                         28

<210> SEQ ID NO 137
<211> LENGTH: 29
<212> TYPE: DNA
<213> ORGANISM: artificial sequence
<220> FEATURE:
<223> OTHER INFORMATION: The forward primer for SNP of specific position
      (chr14:20820537)

<400> SEQUENCE: 137
tctttggaga ttttctgtct tgtaagtcc                                        29

<210> SEQ ID NO 138
<211> LENGTH: 23
<212> TYPE: DNA
<213> ORGANISM: artificial sequence
<220> FEATURE:
<223> OTHER INFORMATION: The reverse primer for SNP of specific position
      (chr14:20820537)

<400> SEQUENCE: 138
aacagagcac agttttgcct cta                                              23

<210> SEQ ID NO 139
<211> LENGTH: 22
<212> TYPE: DNA
<213> ORGANISM: artificial sequence
<220> FEATURE:
<223> OTHER INFORMATION: The forward primer for SNP of specific position
```

-continued (chr14:20905141)

<400> SEQUENCE: 139
tgggacccag gagcgaatat ag                                    22

<210> SEQ ID NO 140
<211> LENGTH: 22
<212> TYPE: DNA
<213> ORGANISM: artificial sequence
<220> FEATURE:
<223> OTHER INFORMATION: The reverse primer for SNP of specific position
      (chr14:20905141)

<400> SEQUENCE: 140
tcctcacagc atgcagatca ag                                    22

<210> SEQ ID NO 141
<211> LENGTH: 29
<212> TYPE: DNA
<213> ORGANISM: artificial sequence
<220> FEATURE:
<223> OTHER INFORMATION: The forward primer for SNP of specific position
      (chr14:20918598)

<400> SEQUENCE: 141
tttgtattaa ggccgttctt catatgtga                             29

<210> SEQ ID NO 142
<211> LENGTH: 25
<212> TYPE: DNA
<213> ORGANISM: artificial sequence
<220> FEATURE:
<223> OTHER INFORMATION: The reverse primer for SNP of specific position
      (chr14:20918598)

<400> SEQUENCE: 142
gtaagaaaca gggagggtga ttagg                                 25

<210> SEQ ID NO 143
<211> LENGTH: 26
<212> TYPE: DNA
<213> ORGANISM: artificial sequence
<220> FEATURE:
<223> OTHER INFORMATION: The forward primer for SNP of specific position
      (chr14:21008574)

<400> SEQUENCE: 143
ctgatgttat caggctattg cagaac                                26

<210> SEQ ID NO 144
<211> LENGTH: 24
<212> TYPE: DNA
<213> ORGANISM: artificial sequence
<220> FEATURE:
<223> OTHER INFORMATION: The reverse primer for SNP of specific position
      (chr14:21008574)

<400> SEQUENCE: 144
caggtcacaa gaaagctttg tgag                                  24

<210> SEQ ID NO 145
<211> LENGTH: 26
<212> TYPE: DNA
<213> ORGANISM: artificial sequence
<220> FEATURE:
<223> OTHER INFORMATION: The forward primer for SNP of specific position
      (chr14:21048774)

<400> SEQUENCE: 145
ggaaacatga gttcctctta cagtga        26

<210> SEQ ID NO 146
<211> LENGTH: 30
<212> TYPE: DNA
<213> ORGANISM: artificial sequence
<220> FEATURE:
<223> OTHER INFORMATION: The reverse primer for SNP of specific position
      (chr14:21048774)

<400> SEQUENCE: 146
gcaaagtttg aactctactg gattagatga        30

<210> SEQ ID NO 147
<211> LENGTH: 22
<212> TYPE: DNA
<213> ORGANISM: artificial sequence
<220> FEATURE:
<223> OTHER INFORMATION: The forward primer for SNP of specific position
      (chr14:21091127)

<400> SEQUENCE: 147
tgggtaccca gtgagcttag at        22

<210> SEQ ID NO 148
<211> LENGTH: 22
<212> TYPE: DNA
<213> ORGANISM: artificial sequence
<220> FEATURE:
<223> OTHER INFORMATION: The reverse primer for SNP of specific position
      (chr14:21091127)

<400> SEQUENCE: 148
ctcagggagc accgcataaa cg        22

<210> SEQ ID NO 149
<211> LENGTH: 29
<212> TYPE: DNA
<213> ORGANISM: artificial sequence
<220> FEATURE:
<223> OTHER INFORMATION: The forward primer for SNP of specific position
      (chr14:21156472)

<400> SEQUENCE: 149
atggaagaag gagaaaccca ggaaacatg        29

<210> SEQ ID NO 150
<211> LENGTH: 29
<212> TYPE: DNA
<213> ORGANISM: artificial sequence
<220> FEATURE:
<223> OTHER INFORMATION: The reverse primer for SNP of specific position
      (chr14:21156472)

<400> SEQUENCE: 150
gtcacagagt aagatatggt cttccagta        29

<210> SEQ ID NO 151
<211> LENGTH: 24
<212> TYPE: DNA
<213> ORGANISM: artificial sequence
<220> FEATURE:
<223> OTHER INFORMATION: The forward primer for SNP of specific position
      (chr14:21195967)

<400> SEQUENCE: 151
gcgttgtgtg agaatagagg aaca                                           24

<210> SEQ ID NO 152
<211> LENGTH: 27
<212> TYPE: DNA
<213> ORGANISM: artificial sequence
<220> FEATURE:
<223> OTHER INFORMATION: The reverse primer for SNP of specific position
      (chr14:21195967)

<400> SEQUENCE: 152
caaatgtcct tttcggattc aatcagg                                        27

<210> SEQ ID NO 153
<211> LENGTH: 28
<212> TYPE: DNA
<213> ORGANISM: artificial sequence
<220> FEATURE:
<223> OTHER INFORMATION: The forward primer for SNP of specific position
      (chr14:21237137)

<400> SEQUENCE: 153
acatttgaca tcattagaag tgctctca                                       28

<210> SEQ ID NO 154
<211> LENGTH: 30
<212> TYPE: DNA
<213> ORGANISM: artificial sequence
<220> FEATURE:
<223> OTHER INFORMATION: The reverse primer for SNP of specific position
      (chr14:21237137)

<400> SEQUENCE: 154
gtaatcaatc aagcaccaag actaaaagag                                     30

<210> SEQ ID NO 155
<211> LENGTH: 26
<212> TYPE: DNA
<213> ORGANISM: artificial sequence
<220> FEATURE:
<223> OTHER INFORMATION: The forward primer for SNP of specific position
      (chr14:21263166)

<400> SEQUENCE: 155
cctttatgca agatggtggt ttttga                                         26

<210> SEQ ID NO 156
<211> LENGTH: 22
<212> TYPE: DNA
<213> ORGANISM: artificial sequence
<220> FEATURE:
<223> OTHER INFORMATION: The reverse primer for SNP of specific position
      (chr14:21263166)

<400> SEQUENCE: 156
gtttggtggc acagctgtaa tc                                             22

<210> SEQ ID NO 157
<211> LENGTH: 28
<212> TYPE: DNA
<213> ORGANISM: artificial sequence
<220> FEATURE:
<223> OTHER INFORMATION: The forward primer for SNP of specific position
      (chr14:21313819)

<400> SEQUENCE: 157
atcccttgta gcaacataaa tggattga                                            28

<210> SEQ ID NO 158
<211> LENGTH: 26
<212> TYPE: DNA
<213> ORGANISM: artificial sequence
<220> FEATURE:
<223> OTHER INFORMATION: The reverse primer for SNP of specific position
      (chr14:21313819)

<400> SEQUENCE: 158
cagaacaatg gcagtatttc tgaagc                                              26

<210> SEQ ID NO 159
<211> LENGTH: 22
<212> TYPE: DNA
<213> ORGANISM: artificial sequence
<220> FEATURE:
<223> OTHER INFORMATION: The forward primer for SNP of specific position
      (chr14:21325985)

<400> SEQUENCE: 159
ccacgccctc aagaatgaaa ca                                                  22

<210> SEQ ID NO 160
<211> LENGTH: 23
<212> TYPE: DNA
<213> ORGANISM: artificial sequence
<220> FEATURE:
<223> OTHER INFORMATION: The reverse primer for SNP of specific position
      (chr14:21325985)

<400> SEQUENCE: 160
caagcacgag ttgaggagta gtc                                                 23

<210> SEQ ID NO 161
<211> LENGTH: 24
<212> TYPE: DNA
<213> ORGANISM: artificial sequence
<220> FEATURE:
<223> OTHER INFORMATION: The forward primer for SNP of specific position
      (chr14:21388266)

<400> SEQUENCE: 161
agtccaggtg cctttaatgt actg                                                24

<210> SEQ ID NO 162
<211> LENGTH: 22
<212> TYPE: DNA
<213> ORGANISM: artificial sequence
<220> FEATURE:
<223> OTHER INFORMATION: The reverse primer for SNP of specific position
      (chr14:21388266)

<400> SEQUENCE: 162
atgctgacac ccagagtaca tg                                                  22

<210> SEQ ID NO 163
<211> LENGTH: 28
<212> TYPE: DNA
<213> ORGANISM: artificial sequence
<220> FEATURE:
<223> OTHER INFORMATION: The forward primer for SNP of specific position
      (chr14:21452591)

<400> SEQUENCE: 163

```
gctgctaaga aatatcttct tccagact                                          28
```

<210> SEQ ID NO 164
<211> LENGTH: 30
<212> TYPE: DNA
<213> ORGANISM: artificial sequence
<220> FEATURE:
<223> OTHER INFORMATION: The reverse primer for SNP of specific position
      (chr14:21452591)

<400> SEQUENCE: 164

```
ggcccttaaa tatgagttga tggtacattt                                        30
```

<210> SEQ ID NO 165
<211> LENGTH: 24
<212> TYPE: DNA
<213> ORGANISM: artificial sequence
<220> FEATURE:
<223> OTHER INFORMATION: The forward primer for SNP of specific position
      (chr14:21519915)

<400> SEQUENCE: 165

```
gatgaatcca ggagtgagga acaa                                              24
```

<210> SEQ ID NO 166
<211> LENGTH: 22
<212> TYPE: DNA
<213> ORGANISM: artificial sequence
<220> FEATURE:
<223> OTHER INFORMATION: The reverse primer for SNP of specific position
      (chr14:21519915)

<400> SEQUENCE: 166

```
agcttcaacc ttcaaacagc ct                                                22
```

<210> SEQ ID NO 167
<211> LENGTH: 25
<212> TYPE: DNA
<213> ORGANISM: artificial sequence
<220> FEATURE:
<223> OTHER INFORMATION: The forward primer for SNP of specific position
      (chr14:21580671)

<400> SEQUENCE: 167

```
caaaacaaaa cccattcgat ccaga                                             25
```

<210> SEQ ID NO 168
<211> LENGTH: 28
<212> TYPE: DNA
<213> ORGANISM: artificial sequence
<220> FEATURE:
<223> OTHER INFORMATION: The reverse primer for SNP of specific position
      (chr14:21580671)

<400> SEQUENCE: 168

```
tacttgcaac aaagaaggag aatactgg                                          28
```

<210> SEQ ID NO 169
<211> LENGTH: 27
<212> TYPE: DNA
<213> ORGANISM: artificial sequence
<220> FEATURE:
<223> OTHER INFORMATION: The forward primer for SNP of specific position
      (chr14:21625262)

<400> SEQUENCE: 169

```
agtgagtctt tgtgaaaatg cctttc                                            27
```

<210> SEQ ID NO 170
<211> LENGTH: 25
<212> TYPE: DNA
<213> ORGANISM: artificial sequence
<220> FEATURE:
<223> OTHER INFORMATION: The reverse primer for SNP of specific position
      (chr14:21625262)

<400> SEQUENCE: 170
gtgtgttatt cgcttactct cctca                                          25

<210> SEQ ID NO 171
<211> LENGTH: 25
<212> TYPE: DNA
<213> ORGANISM: artificial sequence
<220> FEATURE:
<223> OTHER INFORMATION: The forward primer for SNP of specific position
      (chr14:21789092)

<400> SEQUENCE: 171
tgcttgagga cactttttgg aaaac                                          25

<210> SEQ ID NO 172
<211> LENGTH: 25
<212> TYPE: DNA
<213> ORGANISM: artificial sequence
<220> FEATURE:
<223> OTHER INFORMATION: The reverse primer for SNP of specific position
      (chr14:21789092)

<400> SEQUENCE: 172
gtaaaatgcc agcagcagaa actac                                          25

<210> SEQ ID NO 173
<211> LENGTH: 26
<212> TYPE: DNA
<213> ORGANISM: artificial sequence
<220> FEATURE:
<223> OTHER INFORMATION: The forward primer for SNP of specific position
      (chr14:21981923)

<400> SEQUENCE: 173
ttgtagaagg tacatggtac ctgagt                                         26

<210> SEQ ID NO 174
<211> LENGTH: 30
<212> TYPE: DNA
<213> ORGANISM: artificial sequence
<220> FEATURE:
<223> OTHER INFORMATION: The reverse primer for SNP of specific position
      (chr14:21981923)

<400> SEQUENCE: 174
cacatacatc tttcaatagc tcccttcata                                     30

<210> SEQ ID NO 175
<211> LENGTH: 27
<212> TYPE: DNA
<213> ORGANISM: artificial sequence
<220> FEATURE:
<223> OTHER INFORMATION: The forward primer for SNP of specific position
      (chr14:22053817)

<400> SEQUENCE: 175
tcaatagctt ctggcttcaa tctactg                                        27

<210> SEQ ID NO 176
<211> LENGTH: 25
<212> TYPE: DNA
<213> ORGANISM: artificial sequence
<220> FEATURE:
<223> OTHER INFORMATION: The reverse primer for SNP of specific position
      (chr14:22053817)

<400> SEQUENCE: 176
catgagagat tcttgggacc tgaaa                                            25

<210> SEQ ID NO 177
<211> LENGTH: 25
<212> TYPE: DNA
<213> ORGANISM: artificial sequence
<220> FEATURE:
<223> OTHER INFORMATION: The forward primer for SNP of specific position
      (chr14:22090208)

<400> SEQUENCE: 177
gggagctttc cttctctatg tttcc                                            25

<210> SEQ ID NO 178
<211> LENGTH: 24
<212> TYPE: DNA
<213> ORGANISM: artificial sequence
<220> FEATURE:
<223> OTHER INFORMATION: The reverse primer for SNP of specific position
      (chr14:22090208)

<400> SEQUENCE: 178
gatgcttcca tgtggtcaca aaag                                             24

<210> SEQ ID NO 179
<211> LENGTH: 23
<212> TYPE: DNA
<213> ORGANISM: artificial sequence
<220> FEATURE:
<223> OTHER INFORMATION: The forward primer for SNP of specific position
      (chr14:22138437)

<400> SEQUENCE: 179
gcgggaatag atgaagatgc agt                                              23

<210> SEQ ID NO 180
<211> LENGTH: 27
<212> TYPE: DNA
<213> ORGANISM: artificial sequence
<220> FEATURE:
<223> OTHER INFORMATION: The reverse primer for SNP of specific position
      (chr14:22138437)

<400> SEQUENCE: 180
ggtcctgatg agattgacaa cttcttc                                          27

<210> SEQ ID NO 181
<211> LENGTH: 30
<212> TYPE: DNA
<213> ORGANISM: artificial sequence
<220> FEATURE:
<223> OTHER INFORMATION: The forward primer for SNP of specific position
      (chr14:22210067)

<400> SEQUENCE: 181
atgaaaccat tagctcatca ggaattagtt                                       30

-continued

```
<210> SEQ ID NO 182
<211> LENGTH: 30
<212> TYPE: DNA
<213> ORGANISM: artificial sequence
<220> FEATURE:
<223> OTHER INFORMATION: The reverse primer for SNP of specific position
      (chr14:22210067)

<400> SEQUENCE: 182
cacactgcta ataaattcaa aatggcaaaa                                    30

<210> SEQ ID NO 183
<211> LENGTH: 27
<212> TYPE: DNA
<213> ORGANISM: artificial sequence
<220> FEATURE:
<223> OTHER INFORMATION: The forward primer for SNP of specific position
      (chr14:22244363)

<400> SEQUENCE: 183
catgagatac actacatact cacccaa                                       27

<210> SEQ ID NO 184
<211> LENGTH: 22
<212> TYPE: DNA
<213> ORGANISM: artificial sequence
<220> FEATURE:
<223> OTHER INFORMATION: The reverse primer for SNP of specific position
      (chr14:22244363)

<400> SEQUENCE: 184
ccctagccac ttcttgtctg tg                                            22

<210> SEQ ID NO 185
<211> LENGTH: 30
<212> TYPE: DNA
<213> ORGANISM: artificial sequence
<220> FEATURE:
<223> OTHER INFORMATION: The forward primer for SNP of specific position
      (chr14:22263821)

<400> SEQUENCE: 185
tcttataagt gagagacaat ctacaggcaa                                    30

<210> SEQ ID NO 186
<211> LENGTH: 25
<212> TYPE: DNA
<213> ORGANISM: artificial sequence
<220> FEATURE:
<223> OTHER INFORMATION: The reverse primer for SNP of specific position
      (chr14:22263821)

<400> SEQUENCE: 186
cctgttcttc tgaaagaggc ctttt                                         25

<210> SEQ ID NO 187
<211> LENGTH: 22
<212> TYPE: DNA
<213> ORGANISM: artificial sequence
<220> FEATURE:
<223> OTHER INFORMATION: The forward primer for SNP of specific position
      (chr14:22312275)

<400> SEQUENCE: 187
gggcaaatgt gagccaagag ta                                            22

<210> SEQ ID NO 188
```

```
<211> LENGTH: 28
<212> TYPE: DNA
<213> ORGANISM: artificial sequence
<220> FEATURE:
<223> OTHER INFORMATION: The reverse primer for SNP of specific position
      (chr14:22312275)

<400> SEQUENCE: 188
acttagatgg tttctgttaa caagtgct                                          28

<210> SEQ ID NO 189
<211> LENGTH: 22
<212> TYPE: DNA
<213> ORGANISM: artificial sequence
<220> FEATURE:
<223> OTHER INFORMATION: The forward primer for SNP of specific position
      (chr14:22324460)

<400> SEQUENCE: 189
tgtgcacacc attggctgat ta                                                22

<210> SEQ ID NO 190
<211> LENGTH: 29
<212> TYPE: DNA
<213> ORGANISM: artificial sequence
<220> FEATURE:
<223> OTHER INFORMATION: The reverse primer for SNP of specific position
      (chr14:22324460)

<400> SEQUENCE: 190
cacaaggaca caaagatgag aacaataag                                         29

<210> SEQ ID NO 191
<211> LENGTH: 29
<212> TYPE: DNA
<213> ORGANISM: artificial sequence
<220> FEATURE:
<223> OTHER INFORMATION: The forward primer for SNP of specific position
      (chr14:22351977)

<400> SEQUENCE: 191
gtacaataat tcctagagca gaacactca                                         29

<210> SEQ ID NO 192
<211> LENGTH: 30
<212> TYPE: DNA
<213> ORGANISM: artificial sequence
<220> FEATURE:
<223> OTHER INFORMATION: The reverse primer for SNP of specific position
      (chr14:22351977)

<400> SEQUENCE: 192
ccagaatcat tagctgtatg taacgagatg                                        30

<210> SEQ ID NO 193
<211> LENGTH: 30
<212> TYPE: DNA
<213> ORGANISM: artificial sequence
<220> FEATURE:
<223> OTHER INFORMATION: The forward primer for SNP of specific position
      (chr14:22361282)

<400> SEQUENCE: 193
tttgaatcag aagcacatcc tagtaacatt                                        30

<210> SEQ ID NO 194
<211> LENGTH: 30
```

```
<212> TYPE: DNA
<213> ORGANISM: artificial sequence
<220> FEATURE:
<223> OTHER INFORMATION: The reverse primer for SNP of specific position
      (chr14:22361282)

<400> SEQUENCE: 194
gcatagagat cattggaccc taaaacttaa                                      30

<210> SEQ ID NO 195
<211> LENGTH: 30
<212> TYPE: DNA
<213> ORGANISM: artificial sequence
<220> FEATURE:
<223> OTHER INFORMATION: The forward primer for SNP of specific position
      (chr14:22375208)

<400> SEQUENCE: 195
ttagtgtaaa ggtaacagaa ttttcaggct                                      30

<210> SEQ ID NO 196
<211> LENGTH: 26
<212> TYPE: DNA
<213> ORGANISM: artificial sequence
<220> FEATURE:
<223> OTHER INFORMATION: The reverse primer for SNP of specific position
      (chr14:22375208)

<400> SEQUENCE: 196
tcatgatcac agctcagtgt aacttt                                          26

<210> SEQ ID NO 197
<211> LENGTH: 22
<212> TYPE: DNA
<213> ORGANISM: artificial sequence
<220> FEATURE:
<223> OTHER INFORMATION: The forward primer for SNP of specific position
      (chr14:22393124)

<400> SEQUENCE: 197
gcgggaaatc aacatcacag ac                                              22

<210> SEQ ID NO 198
<211> LENGTH: 29
<212> TYPE: DNA
<213> ORGANISM: artificial sequence
<220> FEATURE:
<223> OTHER INFORMATION: The reverse primer for SNP of specific position
      (chr14:22393124)

<400> SEQUENCE: 198
cagtcacatg tttttgaatc cagttcaat                                       29

<210> SEQ ID NO 199
<211> LENGTH: 26
<212> TYPE: DNA
<213> ORGANISM: artificial sequence
<220> FEATURE:
<223> OTHER INFORMATION: The forward primer for SNP of specific position
      (chr14:22428984)

<400> SEQUENCE: 199
cctttagtga ggatttgtca ggtctt                                          26

<210> SEQ ID NO 200
<211> LENGTH: 25
<212> TYPE: DNA
```

```
<213> ORGANISM: artificial sequence
<220> FEATURE:
<223> OTHER INFORMATION: The reverse primer for SNP of specific position
      (chr14:22428984)

<400> SEQUENCE: 200
tgaacttcct aagctcagag ttcct                                          25

<210> SEQ ID NO 201
<211> LENGTH: 30
<212> TYPE: DNA
<213> ORGANISM: artificial sequence
<220> FEATURE:
<223> OTHER INFORMATION: The forward primer for SNP of specific position
      (chr14:22452496)

<400> SEQUENCE: 201
cctattagtg agctattgaa tttggtttgc                                     30

<210> SEQ ID NO 202
<211> LENGTH: 27
<212> TYPE: DNA
<213> ORGANISM: artificial sequence
<220> FEATURE:
<223> OTHER INFORMATION: The reverse primer for SNP of specific position
      (chr14:22452496)

<400> SEQUENCE: 202
acctcctaac aaagaagaca aaagacc                                        27

<210> SEQ ID NO 203
<211> LENGTH: 30
<212> TYPE: DNA
<213> ORGANISM: artificial sequence
<220> FEATURE:
<223> OTHER INFORMATION: The forward primer for SNP of specific position
      (chr14:22489611)

<400> SEQUENCE: 203
cctaggctcc aatattgaaa agtttcaaag                                     30

<210> SEQ ID NO 204
<211> LENGTH: 24
<212> TYPE: DNA
<213> ORGANISM: artificial sequence
<220> FEATURE:
<223> OTHER INFORMATION: The reverse primer for SNP of specific position
      (chr14:22489611)

<400> SEQUENCE: 204
tagtcctgtg gttagcttcc agaa                                           24

<210> SEQ ID NO 205
<211> LENGTH: 24
<212> TYPE: DNA
<213> ORGANISM: artificial sequence
<220> FEATURE:
<223> OTHER INFORMATION: The forward primer for SNP of specific position
      (chr14:22518909)

<400> SEQUENCE: 205
aggaaagagg tttcattggc tgtt                                           24

<210> SEQ ID NO 206
<211> LENGTH: 23
<212> TYPE: DNA
<213> ORGANISM: artificial sequence
```

<220> FEATURE:
<223> OTHER INFORMATION: The reverse primer for SNP of specific position
     (chr14:22518909)

<400> SEQUENCE: 206
gggtaaattt tccctttggt gct     23

<210> SEQ ID NO 207
<211> LENGTH: 26
<212> TYPE: DNA
<213> ORGANISM: artificial sequence
<220> FEATURE:
<223> OTHER INFORMATION: The forward primer for SNP of specific position
     (chr14:22526966)

<400> SEQUENCE: 207
tcagagaagg cctctctgag aaaata     26

<210> SEQ ID NO 208
<211> LENGTH: 27
<212> TYPE: DNA
<213> ORGANISM: artificial sequence
<220> FEATURE:
<223> OTHER INFORMATION: The reverse primer for SNP of specific position
     (chr14:22526966)

<400> SEQUENCE: 208
cctttccctt gaacagttag aagtcac     27

<210> SEQ ID NO 209
<211> LENGTH: 23
<212> TYPE: DNA
<213> ORGANISM: artificial sequence
<220> FEATURE:
<223> OTHER INFORMATION: The forward primer for SNP of specific position
     (chr14:22563283)

<400> SEQUENCE: 209
gcaactggag tcctagccat ttg     23

<210> SEQ ID NO 210
<211> LENGTH: 26
<212> TYPE: DNA
<213> ORGANISM: artificial sequence
<220> FEATURE:
<223> OTHER INFORMATION: The reverse primer for SNP of specific position
     (chr14:22563283)

<400> SEQUENCE: 210
aagaactttg tgcatgtcaa taccac     26

<210> SEQ ID NO 211
<211> LENGTH: 22
<212> TYPE: DNA
<213> ORGANISM: artificial sequence
<220> FEATURE:
<223> OTHER INFORMATION: The forward primer for SNP of specific position
     (chr14:22611651)

<400> SEQUENCE: 211
gtggctgatg aggctgatgt at     22

<210> SEQ ID NO 212
<211> LENGTH: 30
<212> TYPE: DNA
<213> ORGANISM: artificial sequence
<220> FEATURE:

```
<223> OTHER INFORMATION: The reverse primer for SNP of specific position
      (chr14:22611651)

<400> SEQUENCE: 212
ggctaggtca catcaaacaa tttacttaac                                     30

<210> SEQ ID NO 213
<211> LENGTH: 30
<212> TYPE: DNA
<213> ORGANISM: artificial sequence
<220> FEATURE:
<223> OTHER INFORMATION: The forward primer for SNP of specific position
      (chr14:22626948)

<400> SEQUENCE: 213
attcacaggt tatcaaagga gaagtatgac                                     30

<210> SEQ ID NO 214
<211> LENGTH: 25
<212> TYPE: DNA
<213> ORGANISM: artificial sequence
<220> FEATURE:
<223> OTHER INFORMATION: The reverse primer for SNP of specific position
      (chr14:22626948)

<400> SEQUENCE: 214
gttccctgct taatccagta caaac                                          25

<210> SEQ ID NO 215
<211> LENGTH: 29
<212> TYPE: DNA
<213> ORGANISM: artificial sequence
<220> FEATURE:
<223> OTHER INFORMATION: The forward primer for SNP of specific position
      (chr14:22657897)

<400> SEQUENCE: 215
agaaaacacc aagacaaaac agagatttg                                      29

<210> SEQ ID NO 216
<211> LENGTH: 23
<212> TYPE: DNA
<213> ORGANISM: artificial sequence
<220> FEATURE:
<223> OTHER INFORMATION: The reverse primer for SNP of specific position
      (chr14:22657897)

<400> SEQUENCE: 216
gcccataggt actgaagcca aag                                            23

<210> SEQ ID NO 217
<211> LENGTH: 27
<212> TYPE: DNA
<213> ORGANISM: artificial sequence
<220> FEATURE:
<223> OTHER INFORMATION: The forward primer for SNP of specific position
      (chr14:22702039)

<400> SEQUENCE: 217
atgcctttga actgtttgaa actgaat                                        27

<210> SEQ ID NO 218
<211> LENGTH: 30
<212> TYPE: DNA
<213> ORGANISM: artificial sequence
<220> FEATURE:
<223> OTHER INFORMATION: The reverse primer for SNP of specific position
```

(chr14:22702039)

<400> SEQUENCE: 218
attcattcga tattagtgtg agcatatggt                                              30

<210> SEQ ID NO 219
<211> LENGTH: 30
<212> TYPE: DNA
<213> ORGANISM: artificial sequence
<220> FEATURE:
<223> OTHER INFORMATION: The forward primer for SNP of specific position
      (chr14:22731529)

<400> SEQUENCE: 219
tcaacacaat cttagatagc agtagtggta                                              30

<210> SEQ ID NO 220
<211> LENGTH: 30
<212> TYPE: DNA
<213> ORGANISM: artificial sequence
<220> FEATURE:
<223> OTHER INFORMATION: The reverse primer for SNP of specific position
      (chr14:22731529)

<400> SEQUENCE: 220
gtagcttaat aactgataca agagccaaga                                              30

<210> SEQ ID NO 221
<211> LENGTH: 23
<212> TYPE: DNA
<213> ORGANISM: artificial sequence
<220> FEATURE:
<223> OTHER INFORMATION: The forward primer for SNP of specific position
      (chr14:22734948)

<400> SEQUENCE: 221
tcctgctctt ttctagggtc aga                                                     23

<210> SEQ ID NO 222
<211> LENGTH: 30
<212> TYPE: DNA
<213> ORGANISM: artificial sequence
<220> FEATURE:
<223> OTHER INFORMATION: The reverse primer for SNP of specific position
      (chr14:22734948)

<400> SEQUENCE: 222
cagctaatct attcatgggt ctattgttca                                              30

<210> SEQ ID NO 223
<211> LENGTH: 22
<212> TYPE: DNA
<213> ORGANISM: artificial sequence
<220> FEATURE:
<223> OTHER INFORMATION: The forward primer for SNP of specific position
      (chr14:22741160)

<400> SEQUENCE: 223
cctaggtcca ctgcagtaga ac                                                      22

<210> SEQ ID NO 224
<211> LENGTH: 26
<212> TYPE: DNA
<213> ORGANISM: artificial sequence
<220> FEATURE:
<223> OTHER INFORMATION: The reverse primer for SNP of specific position
      (chr14:22741160)

<400> SEQUENCE: 224
tctaatctag cagaacctag ggttgt                                      26

<210> SEQ ID NO 225
<211> LENGTH: 22
<212> TYPE: DNA
<213> ORGANISM: artificial sequence
<220> FEATURE:
<223> OTHER INFORMATION: The forward primer for SNP of specific position
      (chr14:22772663)

<400> SEQUENCE: 225
tcctcctgca ggaactatga ct                                          22

<210> SEQ ID NO 226
<211> LENGTH: 30
<212> TYPE: DNA
<213> ORGANISM: artificial sequence
<220> FEATURE:
<223> OTHER INFORMATION: The reverse primer for SNP of specific position
      (chr14:22772663)

<400> SEQUENCE: 226
gaattatttg tgacagttgc actacatgta                                  30

<210> SEQ ID NO 227
<211> LENGTH: 26
<212> TYPE: DNA
<213> ORGANISM: artificial sequence
<220> FEATURE:
<223> OTHER INFORMATION: The forward primer for SNP of specific position
      (chr14:22861948)

<400> SEQUENCE: 227
aacctggtgc tcaactgtct tattag                                      26

<210> SEQ ID NO 228
<211> LENGTH: 27
<212> TYPE: DNA
<213> ORGANISM: artificial sequence
<220> FEATURE:
<223> OTHER INFORMATION: The reverse primer for SNP of specific position
      (chr14:22861948)

<400> SEQUENCE: 228
ttgagcactc ttcttctgtt gagaaaa                                     27

<210> SEQ ID NO 229
<211> LENGTH: 25
<212> TYPE: DNA
<213> ORGANISM: artificial sequence
<220> FEATURE:
<223> OTHER INFORMATION: The forward primer for SNP of specific position
      (chr14:22972955)

<400> SEQUENCE: 229
gcaacacagg caaactaatc tttgg                                       25

<210> SEQ ID NO 230
<211> LENGTH: 28
<212> TYPE: DNA
<213> ORGANISM: artificial sequence
<220> FEATURE:
<223> OTHER INFORMATION: The reverse primer for SNP of specific position
      (chr14:22972955)

```
<400> SEQUENCE: 230
aattccagat ccaatacacc cttctttt                                          28

<210> SEQ ID NO 231
<211> LENGTH: 29
<212> TYPE: DNA
<213> ORGANISM: artificial sequence
<220> FEATURE:
<223> OTHER INFORMATION: The forward primer for SNP of specific position
      (chr15:20022190)

<400> SEQUENCE: 231
gaagatattt tctttccaca ttgtcctca                                         29

<210> SEQ ID NO 232
<211> LENGTH: 20
<212> TYPE: DNA
<213> ORGANISM: artificial sequence
<220> FEATURE:
<223> OTHER INFORMATION: The reverse primer for SNP of specific position
      (chr15:20022190)

<400> SEQUENCE: 232
aaggaagcca ctcaactgca                                                   20

<210> SEQ ID NO 233
<211> LENGTH: 20
<212> TYPE: DNA
<213> ORGANISM: artificial sequence
<220> FEATURE:
<223> OTHER INFORMATION: The forward primer for SNP of specific position
      (chr15:20049922)

<400> SEQUENCE: 233
cgatgtcgcc tctgttctga                                                   20

<210> SEQ ID NO 234
<211> LENGTH: 33
<212> TYPE: DNA
<213> ORGANISM: artificial sequence
<220> FEATURE:
<223> OTHER INFORMATION: The reverse primer for SNP of specific position
      (chr15:20049922)

<400> SEQUENCE: 234
aaatacaatg caaacttgta ttatctccat atg                                    33

<210> SEQ ID NO 235
<211> LENGTH: 28
<212> TYPE: DNA
<213> ORGANISM: artificial sequence
<220> FEATURE:
<223> OTHER INFORMATION: The forward primer for SNP of specific position
      (chr15:20189367)

<400> SEQUENCE: 235
tggaggtcta atatatggca atgttcct                                          28

<210> SEQ ID NO 236
<211> LENGTH: 30
<212> TYPE: DNA
<213> ORGANISM: artificial sequence
<220> FEATURE:
<223> OTHER INFORMATION: The reverse primer for SNP of specific position
      (chr15:20189367)

<400> SEQUENCE: 236
```
cccacattca ggattgagga ttataataca                                30

<210> SEQ ID NO 237
<211> LENGTH: 28
<212> TYPE: DNA
<213> ORGANISM: artificial sequence
<220> FEATURE:
<223> OTHER INFORMATION: The forward primer for SNP of specific position
      (chr15:20191854)

<400> SEQUENCE: 237
ataaagagac atcagcattc cgtatcag                                  28

<210> SEQ ID NO 238
<211> LENGTH: 30
<212> TYPE: DNA
<213> ORGANISM: artificial sequence
<220> FEATURE:
<223> OTHER INFORMATION: The reverse primer for SNP of specific position
      (chr15:20191854)

<400> SEQUENCE: 238
gttgttgtac caaataaaca caaaaacact                                30

<210> SEQ ID NO 239
<211> LENGTH: 24
<212> TYPE: DNA
<213> ORGANISM: artificial sequence
<220> FEATURE:
<223> OTHER INFORMATION: The forward primer for SNP of specific position
      (chr15:20192138)

<400> SEQUENCE: 239
gaggcctaat ccaaggagag agat                                      24

<210> SEQ ID NO 240
<211> LENGTH: 30
<212> TYPE: DNA
<213> ORGANISM: artificial sequence
<220> FEATURE:
<223> OTHER INFORMATION: The reverse primer for SNP of specific position
      (chr15:20192138)

<400> SEQUENCE: 240
gctttgcagg ccataaatat atacaacaaa                                30

<210> SEQ ID NO 241
<211> LENGTH: 22
<212> TYPE: DNA
<213> ORGANISM: artificial sequence
<220> FEATURE:
<223> OTHER INFORMATION: The forward primer for SNP of specific position
      (chr15:20454253)

<400> SEQUENCE: 241
tcacaaggca tttgggatcc tc                                        22

<210> SEQ ID NO 242
<211> LENGTH: 21
<212> TYPE: DNA
<213> ORGANISM: artificial sequence
<220> FEATURE:
<223> OTHER INFORMATION: The reverse primer for SNP of specific position
      (chr15:20454253)

<400> SEQUENCE: 242
acagagtgag accacactcc a                                              21

<210> SEQ ID NO 243
<211> LENGTH: 25
<212> TYPE: DNA
<213> ORGANISM: artificial sequence
<220> FEATURE:
<223> OTHER INFORMATION: The forward primer for SNP of specific position
      (chr15:20470948)

<400> SEQUENCE: 243
aaaaatccta actgaaaccc actgt                                          25

<210> SEQ ID NO 244
<211> LENGTH: 29
<212> TYPE: DNA
<213> ORGANISM: artificial sequence
<220> FEATURE:
<223> OTHER INFORMATION: The reverse primer for SNP of specific position
      (chr15:20470948)

<400> SEQUENCE: 244
tttataaaca tgctgttgtg ttgcaaaaa                                      29

<210> SEQ ID NO 245
<211> LENGTH: 24
<212> TYPE: DNA
<213> ORGANISM: artificial sequence
<220> FEATURE:
<223> OTHER INFORMATION: The forward primer for SNP of specific position
      (chr15:20564500)

<400> SEQUENCE: 245
gggagggtaa tcacaccaat agag                                           24

<210> SEQ ID NO 246
<211> LENGTH: 30
<212> TYPE: DNA
<213> ORGANISM: artificial sequence
<220> FEATURE:
<223> OTHER INFORMATION: The reverse primer for SNP of specific position
      (chr15:20564500)

<400> SEQUENCE: 246
cttccatcta agaaacacc aatttaggag                                      30

<210> SEQ ID NO 247
<211> LENGTH: 22
<212> TYPE: DNA
<213> ORGANISM: artificial sequence
<220> FEATURE:
<223> OTHER INFORMATION: The forward primer for SNP of specific position
      (chr15:20569241)

<400> SEQUENCE: 247
ctctctttgg ccacatgacc at                                             22

<210> SEQ ID NO 248
<211> LENGTH: 27
<212> TYPE: DNA
<213> ORGANISM: artificial sequence
<220> FEATURE:
<223> OTHER INFORMATION: The reverse primer for SNP of specific position
      (chr15:20569241)

<400> SEQUENCE: 248
taccttgtgt gctaagctgt tcttatg                                        27

<210> SEQ ID NO 249
<211> LENGTH: 22
<212> TYPE: DNA
<213> ORGANISM: artificial sequence
<220> FEATURE:
<223> OTHER INFORMATION: The forward primer for SNP of specific position
      (chr15:20586537)

<400> SEQUENCE: 249
gagtggtgtg actgtggtga at                                              22

<210> SEQ ID NO 250
<211> LENGTH: 25
<212> TYPE: DNA
<213> ORGANISM: artificial sequence
<220> FEATURE:
<223> OTHER INFORMATION: The reverse primer for SNP of specific position
      (chr15:20586537)

<400> SEQUENCE: 250
cactgacctt cataggagac aactg                                           25

<210> SEQ ID NO 251
<211> LENGTH: 32
<212> TYPE: DNA
<213> ORGANISM: artificial sequence
<220> FEATURE:
<223> OTHER INFORMATION: The forward primer for SNP of specific position
      (chr15:20586966)

<400> SEQUENCE: 251
ttgtgtcaca aacaagaagt cttttattaa at                                   32

<210> SEQ ID NO 252
<211> LENGTH: 33
<212> TYPE: DNA
<213> ORGANISM: artificial sequence
<220> FEATURE:
<223> OTHER INFORMATION: The reverse primer for SNP of specific position
      (chr15:20586966)

<400> SEQUENCE: 252
aattaaacat atcacaaaca tgcttggaat ctt                                  33

<210> SEQ ID NO 253
<211> LENGTH: 28
<212> TYPE: DNA
<213> ORGANISM: artificial sequence
<220> FEATURE:
<223> OTHER INFORMATION: The forward primer for SNP of specific position
      (chr15:20590656)

<400> SEQUENCE: 253
cagaatctgt aaacatgcta gtttgcat                                        28

<210> SEQ ID NO 254
<211> LENGTH: 23
<212> TYPE: DNA
<213> ORGANISM: artificial sequence
<220> FEATURE:
<223> OTHER INFORMATION: The reverse primer for SNP of specific position
      (chr15:20590656)

<400> SEQUENCE: 254
gtcttttgca gctcctagaa ggt                                             23

<210> SEQ ID NO 255
<211> LENGTH: 22
<212> TYPE: DNA
<213> ORGANISM: artificial sequence
<220> FEATURE:
<223> OTHER INFORMATION: The forward primer for SNP of specific position
      (chr15:20616721)

<400> SEQUENCE: 255
aggagcatgc catcaggaaa aa                                              22

<210> SEQ ID NO 256
<211> LENGTH: 28
<212> TYPE: DNA
<213> ORGANISM: artificial sequence
<220> FEATURE:
<223> OTHER INFORMATION: The reverse primer for SNP of specific position
      (chr15:20616721)

<400> SEQUENCE: 256
cgaaaggatt atggaagtgt catggtta                                        28

<210> SEQ ID NO 257
<211> LENGTH: 23
<212> TYPE: DNA
<213> ORGANISM: artificial sequence
<220> FEATURE:
<223> OTHER INFORMATION: The forward primer for SNP of specific position
      (chr15:20626721)

<400> SEQUENCE: 257
gttatggcag gaccatcttt cca                                             23

<210> SEQ ID NO 258
<211> LENGTH: 28
<212> TYPE: DNA
<213> ORGANISM: artificial sequence
<220> FEATURE:
<223> OTHER INFORMATION: The reverse primer for SNP of specific position
      (chr15:20626721)

<400> SEQUENCE: 258
agcacacatt ctaaaggaaa tcactcaa                                        28

<210> SEQ ID NO 259
<211> LENGTH: 22
<212> TYPE: DNA
<213> ORGANISM: artificial sequence
<220> FEATURE:
<223> OTHER INFORMATION: The forward primer for SNP of specific position
      (chr15:20646773)

<400> SEQUENCE: 259
caggactcca ctactccctg aa                                              22

<210> SEQ ID NO 260
<211> LENGTH: 30
<212> TYPE: DNA
<213> ORGANISM: artificial sequence
<220> FEATURE:
<223> OTHER INFORMATION: The reverse primer for SNP of specific position
      (chr15:20646773)

<400> SEQUENCE: 260
cccatgagtg tgtctgaata acttagtatc                                      30

```
<210> SEQ ID NO 261
<211> LENGTH: 28
<212> TYPE: DNA
<213> ORGANISM: artificial sequence
<220> FEATURE:
<223> OTHER INFORMATION: The forward primer for SNP of specific position
      (chr15:20848359)

<400> SEQUENCE: 261
tatggtaaga atgtgggtga tgattgac                                      28

<210> SEQ ID NO 262
<211> LENGTH: 25
<212> TYPE: DNA
<213> ORGANISM: artificial sequence
<220> FEATURE:
<223> OTHER INFORMATION: The reverse primer for SNP of specific position
      (chr15:20848359)

<400> SEQUENCE: 262
agaactgagt ccatccctgt agtac                                         25

<210> SEQ ID NO 263
<211> LENGTH: 23
<212> TYPE: DNA
<213> ORGANISM: artificial sequence
<220> FEATURE:
<223> OTHER INFORMATION: The forward primer for SNP of specific position
      (chr15:20849625)

<400> SEQUENCE: 263
ccttcctgtc tgactcctaa gca                                           23

<210> SEQ ID NO 264
<211> LENGTH: 29
<212> TYPE: DNA
<213> ORGANISM: artificial sequence
<220> FEATURE:
<223> OTHER INFORMATION: The reverse primer for SNP of specific position
      (chr15:20849625)

<400> SEQUENCE: 264
actatgttga gatttgactg aatttgcct                                     29

<210> SEQ ID NO 265
<211> LENGTH: 22
<212> TYPE: DNA
<213> ORGANISM: artificial sequence
<220> FEATURE:
<223> OTHER INFORMATION: The forward primer for SNP of specific position
      (chr15:20852181)

<400> SEQUENCE: 265
cacaattgac ggtcgcaagt ac                                            22

<210> SEQ ID NO 266
<211> LENGTH: 22
<212> TYPE: DNA
<213> ORGANISM: artificial sequence
<220> FEATURE:
<223> OTHER INFORMATION: The reverse primer for SNP of specific position
      (chr15:20852181)

<400> SEQUENCE: 266
cagcactggc tcctacctaa aa                                            22

<210> SEQ ID NO 267
```

```
<211> LENGTH: 30
<212> TYPE: DNA
<213> ORGANISM: artificial sequence
<220> FEATURE:
<223> OTHER INFORMATION: The forward primer for SNP of specific position
      (chr15:20862156)

<400> SEQUENCE: 267
ggctacaatc ctttaacttt ctccaatcaa                                          30

<210> SEQ ID NO 268
<211> LENGTH: 29
<212> TYPE: DNA
<213> ORGANISM: artificial sequence
<220> FEATURE:
<223> OTHER INFORMATION: The reverse primer for SNP of specific position
      (chr15:20862156)

<400> SEQUENCE: 268
ttttggtacc aaacaatgat taagggaga                                           29

<210> SEQ ID NO 269
<211> LENGTH: 25
<212> TYPE: DNA
<213> ORGANISM: artificial sequence
<220> FEATURE:
<223> OTHER INFORMATION: The forward primer for SNP of specific position
      (chr15:20863958)

<400> SEQUENCE: 269
tagaacagca acgttttgtt tctgc                                               25

<210> SEQ ID NO 270
<211> LENGTH: 28
<212> TYPE: DNA
<213> ORGANISM: artificial sequence
<220> FEATURE:
<223> OTHER INFORMATION: The reverse primer for SNP of specific position
      (chr15:20863958)

<400> SEQUENCE: 270
cgccctactt ttatgtagta cttgaagt                                            28

<210> SEQ ID NO 271
<211> LENGTH: 21
<212> TYPE: DNA
<213> ORGANISM: artificial sequence
<220> FEATURE:
<223> OTHER INFORMATION: The forward primer for SNP of specific position
      (chr15:21905797)

<400> SEQUENCE: 271
caaccacagc gaaacagtgt c                                                   21

<210> SEQ ID NO 272
<211> LENGTH: 26
<212> TYPE: DNA
<213> ORGANISM: artificial sequence
<220> FEATURE:
<223> OTHER INFORMATION: The reverse primer for SNP of specific position
      (chr15:21905797)

<400> SEQUENCE: 272
tcttctgtgt ctagaggaag agctac                                              26

<210> SEQ ID NO 273
<211> LENGTH: 26
```

```
<212> TYPE: DNA
<213> ORGANISM: artificial sequence
<220> FEATURE:
<223> OTHER INFORMATION: The forward primer for SNP of specific position
      (chr15:21928397)

<400> SEQUENCE: 273
ggtttgatca ggtgtgaagt ttacag                                        26

<210> SEQ ID NO 274
<211> LENGTH: 29
<212> TYPE: DNA
<213> ORGANISM: artificial sequence
<220> FEATURE:
<223> OTHER INFORMATION: The reverse primer for SNP of specific position
      (chr15:21928397)

<400> SEQUENCE: 274
gaagttgtgc caataggaaa atactacct                                     29

<210> SEQ ID NO 275
<211> LENGTH: 23
<212> TYPE: DNA
<213> ORGANISM: artificial sequence
<220> FEATURE:
<223> OTHER INFORMATION: The forward primer for SNP of specific position
      (chr15:21938184)

<400> SEQUENCE: 275
cttcctttct ctgtgcctga gaa                                           23

<210> SEQ ID NO 276
<211> LENGTH: 19
<212> TYPE: DNA
<213> ORGANISM: artificial sequence
<220> FEATURE:
<223> OTHER INFORMATION: The reverse primer for SNP of specific position
      (chr15:21938184)

<400> SEQUENCE: 276
tcccaggagc tctgaccaa                                                19

<210> SEQ ID NO 277
<211> LENGTH: 29
<212> TYPE: DNA
<213> ORGANISM: artificial sequence
<220> FEATURE:
<223> OTHER INFORMATION: The forward primer for SNP of specific position
      (chr15:21940649)

<400> SEQUENCE: 277
ccagtataaa aaggaacact ttacagggt                                     29

<210> SEQ ID NO 278
<211> LENGTH: 30
<212> TYPE: DNA
<213> ORGANISM: artificial sequence
<220> FEATURE:
<223> OTHER INFORMATION: The reverse primer for SNP of specific position
      (chr15:21940649)

<400> SEQUENCE: 278
cacagtgaaa gtaaaactag gaaaatctgc                                    30

<210> SEQ ID NO 279
<211> LENGTH: 20
<212> TYPE: DNA
```

```
<213> ORGANISM: artificial sequence
<220> FEATURE:
<223> OTHER INFORMATION: The forward primer for SNP of specific position
      (chr15:22013203)

<400> SEQUENCE: 279
gcggcacctg agaatccatg                                               20

<210> SEQ ID NO 280
<211> LENGTH: 21
<212> TYPE: DNA
<213> ORGANISM: artificial sequence
<220> FEATURE:
<223> OTHER INFORMATION: The reverse primer for SNP of specific position
      (chr15:22013203)

<400> SEQUENCE: 280
ggtgaggctc cttcagtagc t                                             21

<210> SEQ ID NO 281
<211> LENGTH: 30
<212> TYPE: DNA
<213> ORGANISM: artificial sequence
<220> FEATURE:
<223> OTHER INFORMATION: The forward primer for SNP of specific position
      (chr15:22299435)

<400> SEQUENCE: 281
aggtaaactt cctcctacat tcttctaaaa                                    30

<210> SEQ ID NO 282
<211> LENGTH: 23
<212> TYPE: DNA
<213> ORGANISM: artificial sequence
<220> FEATURE:
<223> OTHER INFORMATION: The reverse primer for SNP of specific position
      (chr15:22299435)

<400> SEQUENCE: 282
tctcaaaatg caagccctct tga                                           23

<210> SEQ ID NO 283
<211> LENGTH: 26
<212> TYPE: DNA
<213> ORGANISM: artificial sequence
<220> FEATURE:
<223> OTHER INFORMATION: The forward primer for SNP of specific position
      (chr15:22302182)

<400> SEQUENCE: 283
gggctgaact ttaagctcta ttcact                                        26

<210> SEQ ID NO 284
<211> LENGTH: 26
<212> TYPE: DNA
<213> ORGANISM: artificial sequence
<220> FEATURE:
<223> OTHER INFORMATION: The reverse primer for SNP of specific position
      (chr15:22302182)

<400> SEQUENCE: 284
gtttcagtca gtgtgaatga gacagt                                        26

<210> SEQ ID NO 285
<211> LENGTH: 27
<212> TYPE: DNA
<213> ORGANISM: artificial sequence
```

```
<220> FEATURE:
<223> OTHER INFORMATION: The forward primer for SNP of specific position
      (chr15:22376163)

<400> SEQUENCE: 285
aaccaagaat ttattttcat gcttgct                                           27

<210> SEQ ID NO 286
<211> LENGTH: 32
<212> TYPE: DNA
<213> ORGANISM: artificial sequence
<220> FEATURE:
<223> OTHER INFORMATION: The reverse primer for SNP of specific position
      (chr15:22376163)

<400> SEQUENCE: 286
ctcagaattt ttaatggcat taccataagg tt                                     32

<210> SEQ ID NO 287
<211> LENGTH: 22
<212> TYPE: DNA
<213> ORGANISM: artificial sequence
<220> FEATURE:
<223> OTHER INFORMATION: The forward primer for SNP of specific position
      (chr15:22427155)

<400> SEQUENCE: 287
ggtgtctttc ttgggtcaag gt                                                22

<210> SEQ ID NO 288
<211> LENGTH: 24
<212> TYPE: DNA
<213> ORGANISM: artificial sequence
<220> FEATURE:
<223> OTHER INFORMATION: The reverse primer for SNP of specific position
      (chr15:22427155)

<400> SEQUENCE: 288
tgaaaatcag cagaggtcat tgct                                              24

<210> SEQ ID NO 289
<211> LENGTH: 22
<212> TYPE: DNA
<213> ORGANISM: artificial sequence
<220> FEATURE:
<223> OTHER INFORMATION: The forward primer for SNP of specific position
      (chr15:22441959)

<400> SEQUENCE: 289
catggtgaac acaagcttgc ta                                                22

<210> SEQ ID NO 290
<211> LENGTH: 22
<212> TYPE: DNA
<213> ORGANISM: artificial sequence
<220> FEATURE:
<223> OTHER INFORMATION: The reverse primer for SNP of specific position
      (chr15:22441959)

<400> SEQUENCE: 290
ttcagtgccg acagccaaga ga                                                22

<210> SEQ ID NO 291
<211> LENGTH: 22
<212> TYPE: DNA
<213> ORGANISM: artificial sequence
<220> FEATURE:
```

```
<223> OTHER INFORMATION: The forward primer for SNP of specific position
      (chr15:22476195)

<400> SEQUENCE: 291
cactcacatc ctggtgtctt gt                                              22

<210> SEQ ID NO 292
<211> LENGTH: 26
<212> TYPE: DNA
<213> ORGANISM: artificial sequence
<220> FEATURE:
<223> OTHER INFORMATION: The reverse primer for SNP of specific position
      (chr15:22476195)

<400> SEQUENCE: 292
gctgtgaatg caatcttggt aatctg                                          26

<210> SEQ ID NO 293
<211> LENGTH: 22
<212> TYPE: DNA
<213> ORGANISM: artificial sequence
<220> FEATURE:
<223> OTHER INFORMATION: The forward primer for SNP of specific position
      (chr15:22520388)

<400> SEQUENCE: 293
cttaggagtg agcatggtcc tt                                              22

<210> SEQ ID NO 294
<211> LENGTH: 30
<212> TYPE: DNA
<213> ORGANISM: artificial sequence
<220> FEATURE:
<223> OTHER INFORMATION: The reverse primer for SNP of specific position
      (chr15:22520388)

<400> SEQUENCE: 294
tacaattagg gttagtgtta gggttaggat                                      30

<210> SEQ ID NO 295
<211> LENGTH: 22
<212> TYPE: DNA
<213> ORGANISM: artificial sequence
<220> FEATURE:
<223> OTHER INFORMATION: The forward primer for SNP of specific position
      (chr15:22539952)

<400> SEQUENCE: 295
acatagcaca tgtgtgtggc at                                              22

<210> SEQ ID NO 296
<211> LENGTH: 28
<212> TYPE: DNA
<213> ORGANISM: artificial sequence
<220> FEATURE:
<223> OTHER INFORMATION: The reverse primer for SNP of specific position
      (chr15:22539952)

<400> SEQUENCE: 296
gatgcattac atgttcctta tgaacagc                                        28

<210> SEQ ID NO 297
<211> LENGTH: 22
<212> TYPE: DNA
<213> ORGANISM: artificial sequence
<220> FEATURE:
<223> OTHER INFORMATION: The forward primer for SNP of specific position
```

(chr15:22780065)

<400> SEQUENCE: 297
gtgtaggttg gttggacagg aa                                          22

<210> SEQ ID NO 298
<211> LENGTH: 25
<212> TYPE: DNA
<213> ORGANISM: artificial sequence
<220> FEATURE:
<223> OTHER INFORMATION: The reverse primer for SNP of specific position
      (chr15:22780065)

<400> SEQUENCE: 298
ttcacttctc acgtgaggat caaag                                       25

<210> SEQ ID NO 299
<211> LENGTH: 25
<212> TYPE: DNA
<213> ORGANISM: artificial sequence
<220> FEATURE:
<223> OTHER INFORMATION: The forward primer for SNP of specific position
      (chr15:22798800)

<400> SEQUENCE: 299
gctttatcaa tcacccgtac agtga                                       25

<210> SEQ ID NO 300
<211> LENGTH: 27
<212> TYPE: DNA
<213> ORGANISM: artificial sequence
<220> FEATURE:
<223> OTHER INFORMATION: The reverse primer for SNP of specific position
      (chr15:22798800)

<400> SEQUENCE: 300
tagagctcac aacctatgat ttaacgc                                     27

<210> SEQ ID NO 301
<211> LENGTH: 22
<212> TYPE: DNA
<213> ORGANISM: artificial sequence
<220> FEATURE:
<223> OTHER INFORMATION: The forward primer for SNP of specific position
      (chr15:22833272)

<400> SEQUENCE: 301
catggatgtg tgtagcgtga ct                                          22

<210> SEQ ID NO 302
<211> LENGTH: 22
<212> TYPE: DNA
<213> ORGANISM: artificial sequence
<220> FEATURE:
<223> OTHER INFORMATION: The reverse primer for SNP of specific position
      (chr15:22833272)

<400> SEQUENCE: 302
cccgacggta cgttttctac tg                                          22

<210> SEQ ID NO 303
<211> LENGTH: 28
<212> TYPE: DNA
<213> ORGANISM: artificial sequence
<220> FEATURE:
<223> OTHER INFORMATION: The forward primer for SNP of specific position
      (chr15:22854479)

-continued

<400> SEQUENCE: 303
gtagagctat ttgtactctt ttagccca                                          28

<210> SEQ ID NO 304
<211> LENGTH: 27
<212> TYPE: DNA
<213> ORGANISM: artificial sequence
<220> FEATURE:
<223> OTHER INFORMATION: The reverse primer for SNP of specific position
      (chr15:22854479)

<400> SEQUENCE: 304
catattgcta cccttccaga acactaa                                           27

<210> SEQ ID NO 305
<211> LENGTH: 30
<212> TYPE: DNA
<213> ORGANISM: artificial sequence
<220> FEATURE:
<223> OTHER INFORMATION: The forward primer for SNP of specific position
      (chr15:22869870)

<400> SEQUENCE: 305
gtcctagttt cattggtgaa tttaaatggc                                        30

<210> SEQ ID NO 306
<211> LENGTH: 28
<212> TYPE: DNA
<213> ORGANISM: artificial sequence
<220> FEATURE:
<223> OTHER INFORMATION: The reverse primer for SNP of specific position
      (chr15:22869870)

<400> SEQUENCE: 306
cagaacacaa actgtgtaac taggtttg                                          28

<210> SEQ ID NO 307
<211> LENGTH: 22
<212> TYPE: DNA
<213> ORGANISM: artificial sequence
<220> FEATURE:
<223> OTHER INFORMATION: The forward primer for SNP of specific position
      (chr15:22893990)

<400> SEQUENCE: 307
cagcggtttt ccaagtgatg tc                                                22

<210> SEQ ID NO 308
<211> LENGTH: 22
<212> TYPE: DNA
<213> ORGANISM: artificial sequence
<220> FEATURE:
<223> OTHER INFORMATION: The reverse primer for SNP of specific position
      (chr15:22893990)

<400> SEQUENCE: 308
gacacctgtc ttaacgcagg aa                                                22

<210> SEQ ID NO 309
<211> LENGTH: 23
<212> TYPE: DNA
<213> ORGANISM: artificial sequence
<220> FEATURE:
<223> OTHER INFORMATION: The forward primer for SNP of specific position
      (chr15:22905599)

```
<400> SEQUENCE: 309
actggtcaca tggaattgac tgt                                          23

<210> SEQ ID NO 310
<211> LENGTH: 22
<212> TYPE: DNA
<213> ORGANISM: artificial sequence
<220> FEATURE:
<223> OTHER INFORMATION: The reverse primer for SNP of specific position
      (chr15:22905599)

<400> SEQUENCE: 310
ggccgacata tgtgaagagg aa                                           22

<210> SEQ ID NO 311
<211> LENGTH: 23
<212> TYPE: DNA
<213> ORGANISM: artificial sequence
<220> FEATURE:
<223> OTHER INFORMATION: The forward primer for SNP of specific position
      (chr15:22916637)

<400> SEQUENCE: 311
ccctgacttg tttgactcct ttg                                          23

<210> SEQ ID NO 312
<211> LENGTH: 25
<212> TYPE: DNA
<213> ORGANISM: artificial sequence
<220> FEATURE:
<223> OTHER INFORMATION: The reverse primer for SNP of specific position
      (chr15:22916637)

<400> SEQUENCE: 312
agcagccaag actaacttta acctg                                        25

<210> SEQ ID NO 313
<211> LENGTH: 22
<212> TYPE: DNA
<213> ORGANISM: artificial sequence
<220> FEATURE:
<223> OTHER INFORMATION: The forward primer for SNP of specific position
      (chr15:22923869)

<400> SEQUENCE: 313
ggccagcatg ctctttgttt tc                                           22

<210> SEQ ID NO 314
<211> LENGTH: 22
<212> TYPE: DNA
<213> ORGANISM: artificial sequence
<220> FEATURE:
<223> OTHER INFORMATION: The reverse primer for SNP of specific position
      (chr15:22923869)

<400> SEQUENCE: 314
atgacgctca gcagagcaca ga                                           22

<210> SEQ ID NO 315
<211> LENGTH: 22
<212> TYPE: DNA
<213> ORGANISM: artificial sequence
<220> FEATURE:
<223> OTHER INFORMATION: The forward primer for SNP of specific position
      (chr15:22940961)

<400> SEQUENCE: 315
```
gctttctctc tgcacagatg ga                                               22

<210> SEQ ID NO 316
<211> LENGTH: 24
<212> TYPE: DNA
<213> ORGANISM: artificial sequence
<220> FEATURE:
<223> OTHER INFORMATION: The reverse primer for SNP of specific position
      (chr15:22940961)

<400> SEQUENCE: 316
gaacctgtcc ctgtcattat gtga                                             24

<210> SEQ ID NO 317
<211> LENGTH: 22
<212> TYPE: DNA
<213> ORGANISM: artificial sequence
<220> FEATURE:
<223> OTHER INFORMATION: The forward primer for SNP of specific position
      (chr15:22971662)

<400> SEQUENCE: 317
ggtggtctgc gactggaatt ta                                               22

<210> SEQ ID NO 318
<211> LENGTH: 27
<212> TYPE: DNA
<213> ORGANISM: artificial sequence
<220> FEATURE:
<223> OTHER INFORMATION: The reverse primer for SNP of specific position
      (chr15:22971662)

<400> SEQUENCE: 318
agaaaaatgg taacatgaca gtgggaa                                          27

<210> SEQ ID NO 319
<211> LENGTH: 22
<212> TYPE: DNA
<213> ORGANISM: artificial sequence
<220> FEATURE:
<223> OTHER INFORMATION: The forward primer for SNP of specific position
      (chr15:23000363)

<400> SEQUENCE: 319
ggctggctgt atgatcatcg ta                                               22

<210> SEQ ID NO 320
<211> LENGTH: 29
<212> TYPE: DNA
<213> ORGANISM: artificial sequence
<220> FEATURE:
<223> OTHER INFORMATION: The reverse primer for SNP of specific position
      (chr15:23000363)

<400> SEQUENCE: 320
gattcatttt gggaacgaaa agaaagttt                                        29

<210> SEQ ID NO 321
<211> LENGTH: 23
<212> TYPE: DNA
<213> ORGANISM: artificial sequence
<220> FEATURE:
<223> OTHER INFORMATION: The forward primer for SNP of specific position
      (chr15:23010627)

<400> SEQUENCE: 321
caggaggccc acaaagaatt cta                                        23

<210> SEQ ID NO 322
<211> LENGTH: 30
<212> TYPE: DNA
<213> ORGANISM: artificial sequence
<220> FEATURE:
<223> OTHER INFORMATION: The reverse primer for SNP of specific position
      (chr15:23010627)

<400> SEQUENCE: 322
tgctctttgt gagattctta ttcatctgtt                                 30

<210> SEQ ID NO 323
<211> LENGTH: 25
<212> TYPE: DNA
<213> ORGANISM: artificial sequence
<220> FEATURE:
<223> OTHER INFORMATION: The forward primer for SNP of specific position
      (chr15:23020535)

<400> SEQUENCE: 323
agccaggata gaatgatgga atgtg                                      25

<210> SEQ ID NO 324
<211> LENGTH: 23
<212> TYPE: DNA
<213> ORGANISM: artificial sequence
<220> FEATURE:
<223> OTHER INFORMATION: The reverse primer for SNP of specific position
      (chr15:23020535)

<400> SEQUENCE: 324
ggctgggatc ttttgtccat gat                                        23

<210> SEQ ID NO 325
<211> LENGTH: 22
<212> TYPE: DNA
<213> ORGANISM: artificial sequence
<220> FEATURE:
<223> OTHER INFORMATION: The forward primer for SNP of specific position
      (chr15:23044004)

<400> SEQUENCE: 325
tgcttggaag caggaagttc ag                                         22

<210> SEQ ID NO 326
<211> LENGTH: 27
<212> TYPE: DNA
<213> ORGANISM: artificial sequence
<220> FEATURE:
<223> OTHER INFORMATION: The reverse primer for SNP of specific position
      (chr15:23044004)

<400> SEQUENCE: 326
ggtgtaaagt ttgcatgatt ccatgaa                                    27

<210> SEQ ID NO 327
<211> LENGTH: 30
<212> TYPE: DNA
<213> ORGANISM: artificial sequence
<220> FEATURE:
<223> OTHER INFORMATION: The forward primer for SNP of specific position
      (chr15:23053813)

<400> SEQUENCE: 327
acatctataa tctccaggct tctaacttgt                                 30

<210> SEQ ID NO 328
<211> LENGTH: 23
<212> TYPE: DNA
<213> ORGANISM: artificial sequence
<220> FEATURE:
<223> OTHER INFORMATION: The reverse primer for SNP of specific position
      (chr15:23053813)

<400> SEQUENCE: 328
ccttaggttc aatgctgacc ctt                                          23

<210> SEQ ID NO 329
<211> LENGTH: 22
<212> TYPE: DNA
<213> ORGANISM: artificial sequence
<220> FEATURE:
<223> OTHER INFORMATION: The forward primer for SNP of specific position
      (chr15:23064687)

<400> SEQUENCE: 329
tactgagtca cctccatggg tt                                           22

<210> SEQ ID NO 330
<211> LENGTH: 24
<212> TYPE: DNA
<213> ORGANISM: artificial sequence
<220> FEATURE:
<223> OTHER INFORMATION: The reverse primer for SNP of specific position
      (chr15:23064687)

<400> SEQUENCE: 330
atacactgag agggacacca gaca                                         24

<210> SEQ ID NO 331
<211> LENGTH: 28
<212> TYPE: DNA
<213> ORGANISM: artificial sequence
<220> FEATURE:
<223> OTHER INFORMATION: The forward primer for SNP of specific position
      (chr15:23721906)

<400> SEQUENCE: 331
cgtctaacct gcaaaatgct aatatctg                                     28

<210> SEQ ID NO 332
<211> LENGTH: 29
<212> TYPE: DNA
<213> ORGANISM: artificial sequence
<220> FEATURE:
<223> OTHER INFORMATION: The reverse primer for SNP of specific position
      (chr15:23721906)

<400> SEQUENCE: 332
gccgatgtta atcttttac atctctctc                                     29

<210> SEQ ID NO 333
<211> LENGTH: 30
<212> TYPE: DNA
<213> ORGANISM: artificial sequence
<220> FEATURE:
<223> OTHER INFORMATION: The forward primer for SNP of specific position
      (chr15:23730971)

<400> SEQUENCE: 333
caataactgc acaaagaaga gagaaaatgg                                   30

<210> SEQ ID NO 334
<211> LENGTH: 30
<212> TYPE: DNA
<213> ORGANISM: artificial sequence
<220> FEATURE:
<223> OTHER INFORMATION: The reverse primer for SNP of specific position
      (chr15:23730971)

<400> SEQUENCE: 334
accatattgc tgctttctgt aattttcatg                                      30

<210> SEQ ID NO 335
<211> LENGTH: 25
<212> TYPE: DNA
<213> ORGANISM: artificial sequence
<220> FEATURE:
<223> OTHER INFORMATION: The forward primer for SNP of specific position
      (chr15:23746510)

<400> SEQUENCE: 335
tgccctaata aacagactcc agaga                                           25

<210> SEQ ID NO 336
<211> LENGTH: 30
<212> TYPE: DNA
<213> ORGANISM: artificial sequence
<220> FEATURE:
<223> OTHER INFORMATION: The reverse primer for SNP of specific position
      (chr15:23746510)

<400> SEQUENCE: 336
cattcaggct gccataacaa aatagtaaag                                      30

<210> SEQ ID NO 337
<211> LENGTH: 27
<212> TYPE: DNA
<213> ORGANISM: artificial sequence
<220> FEATURE:
<223> OTHER INFORMATION: The forward primer for SNP of specific position
      (chr15:23767135)

<400> SEQUENCE: 337
gcctatttct ccaaattctt tcagcct                                         27

<210> SEQ ID NO 338
<211> LENGTH: 30
<212> TYPE: DNA
<213> ORGANISM: artificial sequence
<220> FEATURE:
<223> OTHER INFORMATION: The reverse primer for SNP of specific position
      (chr15:23767135)

<400> SEQUENCE: 338
acctttcttt atgttatgat tcagccagaa                                      30

<210> SEQ ID NO 339
<211> LENGTH: 25
<212> TYPE: DNA
<213> ORGANISM: artificial sequence
<220> FEATURE:
<223> OTHER INFORMATION: The forward primer for SNP of specific position
      (chr15:23781336)

<400> SEQUENCE: 339
caaacctgga aaggagttct cttga                                           25

-continued

```
<210> SEQ ID NO 340
<211> LENGTH: 29
<212> TYPE: DNA
<213> ORGANISM: artificial sequence
<220> FEATURE:
<223> OTHER INFORMATION: The reverse primer for SNP of specific position
      (chr15:23781336)

<400> SEQUENCE: 340
gaataaatca gctcaatagg ctgaattgc                                    29

<210> SEQ ID NO 341
<211> LENGTH: 26
<212> TYPE: DNA
<213> ORGANISM: artificial sequence
<220> FEATURE:
<223> OTHER INFORMATION: The forward primer for SNP of specific position
      (chr15:23793989)

<400> SEQUENCE: 341
gtcctgcctc ctagttttta ttgact                                       26

<210> SEQ ID NO 342
<211> LENGTH: 24
<212> TYPE: DNA
<213> ORGANISM: artificial sequence
<220> FEATURE:
<223> OTHER INFORMATION: The reverse primer for SNP of specific position
      (chr15:23793989)

<400> SEQUENCE: 342
tggaggtaaa ggcaaacact gatc                                         24

<210> SEQ ID NO 343
<211> LENGTH: 27
<212> TYPE: DNA
<213> ORGANISM: artificial sequence
<220> FEATURE:
<223> OTHER INFORMATION: The forward primer for SNP of specific position
      (chr15:23816231)

<400> SEQUENCE: 343
catgtgtctc gatttgatgg atatcca                                      27

<210> SEQ ID NO 344
<211> LENGTH: 23
<212> TYPE: DNA
<213> ORGANISM: artificial sequence
<220> FEATURE:
<223> OTHER INFORMATION: The reverse primer for SNP of specific position
      (chr15:23816231)

<400> SEQUENCE: 344
ctaactctat cccgcactga agt                                          23

<210> SEQ ID NO 345
<211> LENGTH: 22
<212> TYPE: DNA
<213> ORGANISM: artificial sequence
<220> FEATURE:
<223> OTHER INFORMATION: The forward primer for SNP of specific position
      (chr15:23893430)

<400> SEQUENCE: 345
cagaccagtc agactccaca tg                                           22

<210> SEQ ID NO 346
```

<211> LENGTH: 24
<212> TYPE: DNA
<213> ORGANISM: artificial sequence
<220> FEATURE:
<223> OTHER INFORMATION: The reverse primer for SNP of specific position (chr15:23893430)

<400> SEQUENCE: 346
gccttttcca tgtctttgac tcct                                         24

<210> SEQ ID NO 347
<211> LENGTH: 23
<212> TYPE: DNA
<213> ORGANISM: artificial sequence
<220> FEATURE:
<223> OTHER INFORMATION: The forward primer for SNP of specific position (chr15:23929209)

<400> SEQUENCE: 347
ctctgacagc agagaggaaa gtg                                          23

<210> SEQ ID NO 348
<211> LENGTH: 27
<212> TYPE: DNA
<213> ORGANISM: artificial sequence
<220> FEATURE:
<223> OTHER INFORMATION: The reverse primer for SNP of specific position (chr15:23929209)

<400> SEQUENCE: 348
gatgtttcat ttctggagta ggactgt                                      27

<210> SEQ ID NO 349
<211> LENGTH: 23
<212> TYPE: DNA
<213> ORGANISM: artificial sequence
<220> FEATURE:
<223> OTHER INFORMATION: The forward primer for SNP of specific position (chr15:24006330)

<400> SEQUENCE: 349
gggatgttgg cttgtgtgtt ttt                                          23

<210> SEQ ID NO 350
<211> LENGTH: 27
<212> TYPE: DNA
<213> ORGANISM: artificial sequence
<220> FEATURE:
<223> OTHER INFORMATION: The reverse primer for SNP of specific position (chr15:24006330)

<400> SEQUENCE: 350
aacttccttt cctcttttg cattgtc                                       27

<210> SEQ ID NO 351
<211> LENGTH: 28
<212> TYPE: DNA
<213> ORGANISM: artificial sequence
<220> FEATURE:
<223> OTHER INFORMATION: The forward primer for SNP of specific position (chr15:24055535)

<400> SEQUENCE: 351
gtgaatgccc tcttcaatgt aatgaaat                                     28

<210> SEQ ID NO 352
<211> LENGTH: 22

-continued

```
<212> TYPE: DNA
<213> ORGANISM: artificial sequence
<220> FEATURE:
<223> OTHER INFORMATION: The reverse primer for SNP of specific position
      (chr15:24055535)

<400> SEQUENCE: 352
ggttacttga ggtgcagact ga                                              22

<210> SEQ ID NO 353
<211> LENGTH: 30
<212> TYPE: DNA
<213> ORGANISM: artificial sequence
<220> FEATURE:
<223> OTHER INFORMATION: The forward primer for SNP of specific position
      (chr15:24129894)

<400> SEQUENCE: 353
agacctcttg catttccata tagattttca                                      30

<210> SEQ ID NO 354
<211> LENGTH: 33
<212> TYPE: DNA
<213> ORGANISM: artificial sequence
<220> FEATURE:
<223> OTHER INFORMATION: The reverse primer for SNP of specific position
      (chr15:24129894)

<400> SEQUENCE: 354
acagttcatt taaacaagca tcaagaagaa aaa                                  33

<210> SEQ ID NO 355
<211> LENGTH: 25
<212> TYPE: DNA
<213> ORGANISM: artificial sequence
<220> FEATURE:
<223> OTHER INFORMATION: The forward primer for SNP of specific position
      (chr15:24166516)

<400> SEQUENCE: 355
tggtttgttg gttgattgtt tgtgt                                           25

<210> SEQ ID NO 356
<211> LENGTH: 30
<212> TYPE: DNA
<213> ORGANISM: artificial sequence
<220> FEATURE:
<223> OTHER INFORMATION: The reverse primer for SNP of specific position
      (chr15:24166516)

<400> SEQUENCE: 356
acatacatat tctttgctat cagctgacaa                                      30

<210> SEQ ID NO 357
<211> LENGTH: 30
<212> TYPE: DNA
<213> ORGANISM: artificial sequence
<220> FEATURE:
<223> OTHER INFORMATION: The forward primer for SNP of specific position
      (chr15:24196094)

<400> SEQUENCE: 357
aaactttgtt tagtggttaa actaggcaat                                      30

<210> SEQ ID NO 358
<211> LENGTH: 24
<212> TYPE: DNA
```

-continued

```
<213> ORGANISM: artificial sequence
<220> FEATURE:
<223> OTHER INFORMATION: The reverse primer for SNP of specific position
      (chr15:24196094)

<400> SEQUENCE: 358
acttgacaga aagtgtgaac acct                                              24

<210> SEQ ID NO 359
<211> LENGTH: 25
<212> TYPE: DNA
<213> ORGANISM: artificial sequence
<220> FEATURE:
<223> OTHER INFORMATION: The forward primer for SNP of specific position
      (chr15:24236177)

<400> SEQUENCE: 359
ggtttgatac ttgtagagcc aggta                                             25

<210> SEQ ID NO 360
<211> LENGTH: 23
<212> TYPE: DNA
<213> ORGANISM: artificial sequence
<220> FEATURE:
<223> OTHER INFORMATION: The reverse primer for SNP of specific position
      (chr15:24236177)

<400> SEQUENCE: 360
cacaatgcaa gaggagatgt cct                                               23

<210> SEQ ID NO 361
<211> LENGTH: 30
<212> TYPE: DNA
<213> ORGANISM: artificial sequence
<220> FEATURE:
<223> OTHER INFORMATION: The forward primer for SNP of specific position
      (chr15:24278723)

<400> SEQUENCE: 361
tgcttattgt atgtgactat cacttccttg                                        30

<210> SEQ ID NO 362
<211> LENGTH: 29
<212> TYPE: DNA
<213> ORGANISM: artificial sequence
<220> FEATURE:
<223> OTHER INFORMATION: The reverse primer for SNP of specific position
      (chr15:24278723)

<400> SEQUENCE: 362
atgcacaagc ataagaaaca gatgaaaaa                                         29

<210> SEQ ID NO 363
<211> LENGTH: 23
<212> TYPE: DNA
<213> ORGANISM: artificial sequence
<220> FEATURE:
<223> OTHER INFORMATION: The forward primer for SNP of specific position
      (chr15:24319610)

<400> SEQUENCE: 363
cccatgcaga caatctttgg ttg                                               23

<210> SEQ ID NO 364
<211> LENGTH: 26
<212> TYPE: DNA
<213> ORGANISM: artificial sequence
```

<220> FEATURE:
<223> OTHER INFORMATION: The reverse primer for SNP of specific position
      (chr15:24319610)

<400> SEQUENCE: 364
agctccatca tattctcatg agacct                                          26

<210> SEQ ID NO 365
<211> LENGTH: 32
<212> TYPE: DNA
<213> ORGANISM: artificial sequence
<220> FEATURE:
<223> OTHER INFORMATION: The forward primer for SNP of specific position
      (chr15:24350583)

<400> SEQUENCE: 365
aggttttatg gtttttatgg tttttatggt tt                                   32

<210> SEQ ID NO 366
<211> LENGTH: 33
<212> TYPE: DNA
<213> ORGANISM: artificial sequence
<220> FEATURE:
<223> OTHER INFORMATION: The reverse primer for SNP of specific position
      (chr15:24350583)

<400> SEQUENCE: 366
aacaaaacta tacatgtatc cacaaaccta aat                                  33

<210> SEQ ID NO 367
<211> LENGTH: 23
<212> TYPE: DNA
<213> ORGANISM: artificial sequence
<220> FEATURE:
<223> OTHER INFORMATION: The forward primer for SNP of specific position
      (chr15:24471640)

<400> SEQUENCE: 367
acctgggtga caagaaagag aga                                             23

<210> SEQ ID NO 368
<211> LENGTH: 25
<212> TYPE: DNA
<213> ORGANISM: artificial sequence
<220> FEATURE:
<223> OTHER INFORMATION: The reverse primer for SNP of specific position
      (chr15:24471640)

<400> SEQUENCE: 368
gtcttgtccc ttcagagttt acagt                                           25

<210> SEQ ID NO 369
<211> LENGTH: 29
<212> TYPE: DNA
<213> ORGANISM: artificial sequence
<220> FEATURE:
<223> OTHER INFORMATION: The forward primer for SNP of specific position
      (chr15:24824114)

<400> SEQUENCE: 369
aaaaatagaa agaagtgtcc ctcatctgt                                       29

<210> SEQ ID NO 370
<211> LENGTH: 22
<212> TYPE: DNA
<213> ORGANISM: artificial sequence
<220> FEATURE:

<223> OTHER INFORMATION: The reverse primer for SNP of specific position
      (chr15:24824114)

<400> SEQUENCE: 370
ccttctgcat gccctgtata cc                                           22

<210> SEQ ID NO 371
<211> LENGTH: 27
<212> TYPE: DNA
<213> ORGANISM: artificial sequence
<220> FEATURE:
<223> OTHER INFORMATION: The forward primer for SNP of specific position
      (chr15:24870875)

<400> SEQUENCE: 371
tctgtcattt cttgtttgct tttgagg                                      27

<210> SEQ ID NO 372
<211> LENGTH: 30
<212> TYPE: DNA
<213> ORGANISM: artificial sequence
<220> FEATURE:
<223> OTHER INFORMATION: The reverse primer for SNP of specific position
      (chr15:24870875)

<400> SEQUENCE: 372
gaaaggagcc ataaggatgt attccaatat                                   30

<210> SEQ ID NO 373
<211> LENGTH: 26
<212> TYPE: DNA
<213> ORGANISM: artificial sequence
<220> FEATURE:
<223> OTHER INFORMATION: The forward primer for SNP of specific position
      (chr15:24913763)

<400> SEQUENCE: 373
agaagttcag gtgattactt ggcatt                                       26

<210> SEQ ID NO 374
<211> LENGTH: 25
<212> TYPE: DNA
<213> ORGANISM: artificial sequence
<220> FEATURE:
<223> OTHER INFORMATION: The reverse primer for SNP of specific position
      (chr15:24913763)

<400> SEQUENCE: 374
aaatggcaga gatagagcag aagtg                                        25

<210> SEQ ID NO 375
<211> LENGTH: 29
<212> TYPE: DNA
<213> ORGANISM: artificial sequence
<220> FEATURE:
<223> OTHER INFORMATION: The forward primer for SNP of specific position
      (chr15:24943341)

<400> SEQUENCE: 375
tctgctgtat gtttccattt ctgatagag                                    29

<210> SEQ ID NO 376
<211> LENGTH: 30
<212> TYPE: DNA
<213> ORGANISM: artificial sequence
<220> FEATURE:
<223> OTHER INFORMATION: The reverse primer for SNP of specific position (chr15:24943341)

<400> SEQUENCE: 376
gctagcatta aaagaaagta cgtgtatctg                              30

<210> SEQ ID NO 377
<211> LENGTH: 22
<212> TYPE: DNA
<213> ORGANISM: artificial sequence
<220> FEATURE:
<223> OTHER INFORMATION: The forward primer for SNP of specific position
      (chr15:24974072)

<400> SEQUENCE: 377
acctccatga tgcctatgag ct                                      22

<210> SEQ ID NO 378
<211> LENGTH: 23
<212> TYPE: DNA
<213> ORGANISM: artificial sequence
<220> FEATURE:
<223> OTHER INFORMATION: The reverse primer for SNP of specific position
      (chr15:24974072)

<400> SEQUENCE: 378
tgctgtgcac cagccaatta ata                                     23

<210> SEQ ID NO 379
<211> LENGTH: 33
<212> TYPE: DNA
<213> ORGANISM: artificial sequence
<220> FEATURE:
<223> OTHER INFORMATION: The forward primer for SNP of specific position
      (chr21:14640496)

<400> SEQUENCE: 379
ccttcggatg aaaatgagga taagataata tga                          33

<210> SEQ ID NO 380
<211> LENGTH: 32
<212> TYPE: DNA
<213> ORGANISM: artificial sequence
<220> FEATURE:
<223> OTHER INFORMATION: The reverse primer for SNP of specific position
      (chr21:14640496)

<400> SEQUENCE: 380
ggagctttca atgtaatttc tactagaatt gg                           32

<210> SEQ ID NO 381
<211> LENGTH: 33
<212> TYPE: DNA
<213> ORGANISM: artificial sequence
<220> FEATURE:
<223> OTHER INFORMATION: The forward primer for SNP of specific position
      (chr21:14643423)

<400> SEQUENCE: 381
actctttatc tcatttatct gaagaaaatg cac                          33

<210> SEQ ID NO 382
<211> LENGTH: 24
<212> TYPE: DNA
<213> ORGANISM: artificial sequence
<220> FEATURE:
<223> OTHER INFORMATION: The reverse primer for SNP of specific position
      (chr21:14643423)

-continued

<400> SEQUENCE: 382
ccctgtaaca gggcttactt catt                                          24

<210> SEQ ID NO 383
<211> LENGTH: 24
<212> TYPE: DNA
<213> ORGANISM: artificial sequence
<220> FEATURE:
<223> OTHER INFORMATION: The forward primer for SNP of specific position
      (chr21:14695894)

<400> SEQUENCE: 383
cagacttgca tagagcctgt atgt                                          24

<210> SEQ ID NO 384
<211> LENGTH: 26
<212> TYPE: DNA
<213> ORGANISM: artificial sequence
<220> FEATURE:
<223> OTHER INFORMATION: The reverse primer for SNP of specific position
      (chr21:14695894)

<400> SEQUENCE: 384
cttagcctcc aacctacatc tttctc                                        26

<210> SEQ ID NO 385
<211> LENGTH: 29
<212> TYPE: DNA
<213> ORGANISM: artificial sequence
<220> FEATURE:
<223> OTHER INFORMATION: The forward primer for SNP of specific position
      (chr21:14756515)

<400> SEQUENCE: 385
tctcttagct ttcaatttgg tggaaatga                                     29

<210> SEQ ID NO 386
<211> LENGTH: 24
<212> TYPE: DNA
<213> ORGANISM: artificial sequence
<220> FEATURE:
<223> OTHER INFORMATION: The reverse primer for SNP of specific position
      (chr21:14756515)

<400> SEQUENCE: 386
accttcctga aagaaaatgg cctt                                          24

<210> SEQ ID NO 387
<211> LENGTH: 22
<212> TYPE: DNA
<213> ORGANISM: artificial sequence
<220> FEATURE:
<223> OTHER INFORMATION: The forward primer for SNP of specific position
      (chr21:14818516)

<400> SEQUENCE: 387
caaggtggta acagcctacc aa                                            22

<210> SEQ ID NO 388
<211> LENGTH: 28
<212> TYPE: DNA
<213> ORGANISM: artificial sequence
<220> FEATURE:
<223> OTHER INFORMATION: The reverse primer for SNP of specific position
      (chr21:14818516)

<400> SEQUENCE: 388
cctgtatctt cgcttctgtt cttaacat                                    28

<210> SEQ ID NO 389
<211> LENGTH: 28
<212> TYPE: DNA
<213> ORGANISM: artificial sequence
<220> FEATURE:
<223> OTHER INFORMATION: The forward primer for SNP of specific position
      (chr21:14890028)

<400> SEQUENCE: 389
gaggatggta aggatagagg aaagaaga                                    28

<210> SEQ ID NO 390
<211> LENGTH: 25
<212> TYPE: DNA
<213> ORGANISM: artificial sequence
<220> FEATURE:
<223> OTHER INFORMATION: The reverse primer for SNP of specific position
      (chr21:14890028)

<400> SEQUENCE: 390
caccttcttt tctcaaccac ctttg                                       25

<210> SEQ ID NO 391
<211> LENGTH: 23
<212> TYPE: DNA
<213> ORGANISM: artificial sequence
<220> FEATURE:
<223> OTHER INFORMATION: The forward primer for SNP of specific position
      (chr21:15012159)

<400> SEQUENCE: 391
gcagatagaa gtggctgaac aga                                         23

<210> SEQ ID NO 392
<211> LENGTH: 33
<212> TYPE: DNA
<213> ORGANISM: artificial sequence
<220> FEATURE:
<223> OTHER INFORMATION: The reverse primer for SNP of specific position
      (chr21:15012159)

<400> SEQUENCE: 392
tgcagttgaa ttaagaacat ggttttatcc tat                              33

<210> SEQ ID NO 393
<211> LENGTH: 33
<212> TYPE: DNA
<213> ORGANISM: artificial sequence
<220> FEATURE:
<223> OTHER INFORMATION: The forward primer for SNP of specific position
      (chr21:15026905)

<400> SEQUENCE: 393
caaatccctt tacaggttag tttgtaaaat cag                              33

<210> SEQ ID NO 394
<211> LENGTH: 30
<212> TYPE: DNA
<213> ORGANISM: artificial sequence
<220> FEATURE:
<223> OTHER INFORMATION: The reverse primer for SNP of specific position
      (chr21:15026905)

<400> SEQUENCE: 394
tcaatgggtc ttaataatca aatgactcca                        30

<210> SEQ ID NO 395
<211> LENGTH: 25
<212> TYPE: DNA
<213> ORGANISM: artificial sequence
<220> FEATURE:
<223> OTHER INFORMATION: The forward primer for SNP of specific position
      (chr21:15170049)

<400> SEQUENCE: 395 cttttccac cttgaatgca tgaga                              25

<210> SEQ ID NO 396
<211> LENGTH: 25
<212> TYPE: DNA
<213> ORGANISM: artificial sequence
<220> FEATURE:
<223> OTHER INFORMATION: The reverse primer for SNP of specific position
      (chr21:15170049)

<400> SEQUENCE: 396
gggttttctg gagagatagt ggtag                             25

<210> SEQ ID NO 397
<211> LENGTH: 24
<212> TYPE: DNA
<213> ORGANISM: artificial sequence
<220> FEATURE:
<223> OTHER INFORMATION: The forward primer for SNP of specific position
      (chr21:15280687)

<400> SEQUENCE: 397
cctcatcact gtcaccttag agtg                              24

<210> SEQ ID NO 398
<211> LENGTH: 30
<212> TYPE: DNA
<213> ORGANISM: artificial sequence
<220> FEATURE:
<223> OTHER INFORMATION: The reverse primer for SNP of specific position
      (chr21:15280687)

<400> SEQUENCE: 398
gaaagagaaa gtgagaagat gtgttgaatg                        30

<210> SEQ ID NO 399
<211> LENGTH: 30
<212> TYPE: DNA
<213> ORGANISM: artificial sequence
<220> FEATURE:
<223> OTHER INFORMATION: The forward primer for SNP of specific position
      (chr21:15300595)

<400> SEQUENCE: 399
acacatggtc tcatccagaa atctattttt                        30

<210> SEQ ID NO 400
<211> LENGTH: 30
<212> TYPE: DNA
<213> ORGANISM: artificial sequence
<220> FEATURE:
<223> OTHER INFORMATION: The reverse primer for SNP of specific position
      (chr21:15300595)

<400> SEQUENCE: 400
caaacaaaca aacagaaagg aataggactg                                30

<210> SEQ ID NO 401
<211> LENGTH: 21
<212> TYPE: DNA
<213> ORGANISM: artificial sequence
<220> FEATURE:
<223> OTHER INFORMATION: The forward primer for SNP of specific position
      (chr21:15445542)

<400> SEQUENCE: 401
gacctgcctc gctacctttt a                                         21

<210> SEQ ID NO 402
<211> LENGTH: 24
<212> TYPE: DNA
<213> ORGANISM: artificial sequence
<220> FEATURE:
<223> OTHER INFORMATION: The reverse primer for SNP of specific position
      (chr21:15445542)

<400> SEQUENCE: 402
gcttgtactc agaatgcatg tctc                                      24

<210> SEQ ID NO 403
<211> LENGTH: 29
<212> TYPE: DNA
<213> ORGANISM: artificial sequence
<220> FEATURE:
<223> OTHER INFORMATION: The forward primer for SNP of specific position
      (chr21:15479041)

<400> SEQUENCE: 403
tgagttattc tggaagactg ttatcacct                                 29

<210> SEQ ID NO 404
<211> LENGTH: 29
<212> TYPE: DNA
<213> ORGANISM: artificial sequence
<220> FEATURE:
<223> OTHER INFORMATION: The reverse primer for SNP of specific position
      (chr21:15479041)

<400> SEQUENCE: 404
cacacaacct catgctattt tacttttct                                 29

<210> SEQ ID NO 405
<211> LENGTH: 27
<212> TYPE: DNA
<213> ORGANISM: artificial sequence
<220> FEATURE:
<223> OTHER INFORMATION: The forward primer for SNP of specific position
      (chr21:15501432)

<400> SEQUENCE: 405
cagagccttc ctatatcctt aacaacg                                   27

<210> SEQ ID NO 406
<211> LENGTH: 23
<212> TYPE: DNA
<213> ORGANISM: artificial sequence
<220> FEATURE:
<223> OTHER INFORMATION: The reverse primer for SNP of specific position
      (chr21:15501432)

<400> SEQUENCE: 406
aacaggctga ccacgtcata att                                       23

<210> SEQ ID NO 407
<211> LENGTH: 29
<212> TYPE: DNA
<213> ORGANISM: artificial sequence
<220> FEATURE:
<223> OTHER INFORMATION: The forward primer for SNP of specific position
      (chr21:15548748)

<400> SEQUENCE: 407
tgcaaaattt ggcttttaa atcatctgc                                    29

<210> SEQ ID NO 408
<211> LENGTH: 30
<212> TYPE: DNA
<213> ORGANISM: artificial sequence
<220> FEATURE:
<223> OTHER INFORMATION: The reverse primer for SNP of specific position
      (chr21:15548748)

<400> SEQUENCE: 408
gccatggcta gaagttaatg tatagttttg                                  30

<210> SEQ ID NO 409
<211> LENGTH: 30
<212> TYPE: DNA
<213> ORGANISM: artificial sequence
<220> FEATURE:
<223> OTHER INFORMATION: The forward primer for SNP of specific position
      (chr21:15566056)

<400> SEQUENCE: 409
caatgcaaaa tgtaactaaa agtgagcaga                                  30

<210> SEQ ID NO 410
<211> LENGTH: 22
<212> TYPE: DNA
<213> ORGANISM: artificial sequence
<220> FEATURE:
<223> OTHER INFORMATION: The reverse primer for SNP of specific position
      (chr21:15566056)

<400> SEQUENCE: 410
cgcctgtggt tctgttcttg ta                                          22

<210> SEQ ID NO 411
<211> LENGTH: 22
<212> TYPE: DNA
<213> ORGANISM: artificial sequence
<220> FEATURE:
<223> OTHER INFORMATION: The forward primer for SNP of specific position
      (chr21:15588845)

<400> SEQUENCE: 411
gttccttcag gtaccgtctc tg                                          22

<210> SEQ ID NO 412
<211> LENGTH: 23
<212> TYPE: DNA
<213> ORGANISM: artificial sequence
<220> FEATURE:
<223> OTHER INFORMATION: The reverse primer for SNP of specific position
      (chr21:15588845)

<400> SEQUENCE: 412 ggaagcccctt aatcagaaac ggg                                         23

<210> SEQ ID NO 413
<211> LENGTH: 22
<212> TYPE: DNA
<213> ORGANISM: artificial sequence
<220> FEATURE:
<223> OTHER INFORMATION: The forward primer for SNP of specific position
      (chr21:15625530)

<400> SEQUENCE: 413
ctggcggtat ctcatccatc aa                                              22

<210> SEQ ID NO 414
<211> LENGTH: 27
<212> TYPE: DNA
<213> ORGANISM: artificial sequence
<220> FEATURE:
<223> OTHER INFORMATION: The reverse primer for SNP of specific position
      (chr21:15625530)

<400> SEQUENCE: 414
cctctgagat acatttcaag aagggtt                                         27

<210> SEQ ID NO 415
<211> LENGTH: 27
<212> TYPE: DNA
<213> ORGANISM: artificial sequence
<220> FEATURE:
<223> OTHER INFORMATION: The forward primer for SNP of specific position
      (chr21:15654618)

<400> SEQUENCE: 415
ggaagaacct attgaatagg ctgaaca                                         27

<210> SEQ ID NO 416
<211> LENGTH: 30
<212> TYPE: DNA
<213> ORGANISM: artificial sequence
<220> FEATURE:
<223> OTHER INFORMATION: The reverse primer for SNP of specific position
      (chr21:15654618)

<400> SEQUENCE: 416
gatcttcatg ttgccaaatt taatggagaa                                      30

<210> SEQ ID NO 417
<211> LENGTH: 30
<212> TYPE: DNA
<213> ORGANISM: artificial sequence
<220> FEATURE:
<223> OTHER INFORMATION: The forward primer for SNP of specific position
      (chr21:15681452)

<400> SEQUENCE: 417
acaaccacaa aaagaatttc ctatgttgtc                                      30

<210> SEQ ID NO 418
<211> LENGTH: 30
<212> TYPE: DNA
<213> ORGANISM: artificial sequence
<220> FEATURE:
<223> OTHER INFORMATION: The reverse primer for SNP of specific position
      (chr21:15681452)

<400> SEQUENCE: 418
atgacaagtt ggctatagct tgttacatta                                      30

-continued

<210> SEQ ID NO 419
<211> LENGTH: 30
<212> TYPE: DNA
<213> ORGANISM: artificial sequence
<220> FEATURE:
<223> OTHER INFORMATION: The forward primer for SNP of specific position
      (chr21:15720558)

<400> SEQUENCE: 419
tgacctaata tcaaattttt cagggcgtat                                    30

<210> SEQ ID NO 420
<211> LENGTH: 25
<212> TYPE: DNA
<213> ORGANISM: artificial sequence
<220> FEATURE:
<223> OTHER INFORMATION: The reverse primer for SNP of specific position
      (chr21:15720558)

<400> SEQUENCE: 420
cctggacaaa gaggaggttt aagtg                                         25

<210> SEQ ID NO 421
<211> LENGTH: 30
<212> TYPE: DNA
<213> ORGANISM: artificial sequence
<220> FEATURE:
<223> OTHER INFORMATION: The forward primer for SNP of specific position
      (chr21:15763305)

<400> SEQUENCE: 421
agctatggat atagatcaat gcatggattt                                    30

<210> SEQ ID NO 422
<211> LENGTH: 30
<212> TYPE: DNA
<213> ORGANISM: artificial sequence
<220> FEATURE:
<223> OTHER INFORMATION: The reverse primer for SNP of specific position
      (chr21:15763305)

<400> SEQUENCE: 422
gcatccttca agacatgata aaaggactaa                                    30

<210> SEQ ID NO 423
<211> LENGTH: 24
<212> TYPE: DNA
<213> ORGANISM: artificial sequence
<220> FEATURE:
<223> OTHER INFORMATION: The forward primer for SNP of specific position
      (chr21:15842397)

<400> SEQUENCE: 423
ccaacttgca atgagatggt tctt                                          24

<210> SEQ ID NO 424
<211> LENGTH: 30
<212> TYPE: DNA
<213> ORGANISM: artificial sequence
<220> FEATURE:
<223> OTHER INFORMATION: The reverse primer for SNP of specific position
      (chr21:15842397)

<400> SEQUENCE: 424
gcacagggtt ttgctacaat tttacttaaa                                    30

<210> SEQ ID NO 425

```
<211> LENGTH: 29
<212> TYPE: DNA
<213> ORGANISM: artificial sequence
<220> FEATURE:
<223> OTHER INFORMATION: The forward primer for SNP of specific position
      (chr21:15884516)

<400> SEQUENCE: 425
aattgatgca aatgtgctac atttttcag                                          29

<210> SEQ ID NO 426
<211> LENGTH: 22
<212> TYPE: DNA
<213> ORGANISM: artificial sequence
<220> FEATURE:
<223> OTHER INFORMATION: The reverse primer for SNP of specific position
      (chr21:15884516)

<400> SEQUENCE: 426
gctcctcggg atactcctca aa                                                 22

<210> SEQ ID NO 427
<211> LENGTH: 28
<212> TYPE: DNA
<213> ORGANISM: artificial sequence
<220> FEATURE:
<223> OTHER INFORMATION: The forward primer for SNP of specific position
      (chr21:15916232)

<400> SEQUENCE: 427
ggtcacttga aatagaacca atgacagt                                           28

<210> SEQ ID NO 428
<211> LENGTH: 26
<212> TYPE: DNA
<213> ORGANISM: artificial sequence
<220> FEATURE:
<223> OTHER INFORMATION: The reverse primer for SNP of specific position
      (chr21:15916232)

<400> SEQUENCE: 428
acagaaccat caagaaattg gtctga                                             26

<210> SEQ ID NO 429
<211> LENGTH: 28
<212> TYPE: DNA
<213> ORGANISM: artificial sequence
<220> FEATURE:
<223> OTHER INFORMATION: The forward primer for SNP of specific position
      (chr21:15942816)

<400> SEQUENCE: 429
cacaaatgaa agccaccctt aatattca                                           28

<210> SEQ ID NO 430
<211> LENGTH: 23
<212> TYPE: DNA
<213> ORGANISM: artificial sequence
<220> FEATURE:
<223> OTHER INFORMATION: The reverse primer for SNP of specific position
      (chr21:15942816)

<400> SEQUENCE: 430
cgactgcaca ttccaaatct gtc                                                23

<210> SEQ ID NO 431
<211> LENGTH: 22
```

```
<212> TYPE: DNA
<213> ORGANISM: artificial sequence
<220> FEATURE:
<223> OTHER INFORMATION: The forward primer for SNP of specific position
      (chr21:15984234)

<400> SEQUENCE: 431
actgcaggac cctgatagga tc                                          22

<210> SEQ ID NO 432
<211> LENGTH: 29
<212> TYPE: DNA
<213> ORGANISM: artificial sequence
<220> FEATURE:
<223> OTHER INFORMATION: The reverse primer for SNP of specific position
      (chr21:15984234)

<400> SEQUENCE: 432
tttttaatgt agtgtgccaa acttatggg                                   29

<210> SEQ ID NO 433
<211> LENGTH: 33
<212> TYPE: DNA
<213> ORGANISM: artificial sequence
<220> FEATURE:
<223> OTHER INFORMATION: The forward primer for SNP of specific position
      (chr21:16027704)

<400> SEQUENCE: 433
ctagaccttt cataagagag aattagaaaa tgc                              33

<210> SEQ ID NO 434
<211> LENGTH: 32
<212> TYPE: DNA
<213> ORGANISM: artificial sequence
<220> FEATURE:
<223> OTHER INFORMATION: The reverse primer for SNP of specific position
      (chr21:16027704)

<400> SEQUENCE: 434
acctaaaatt gatctgttgt tttcttgcat ta                               32

<210> SEQ ID NO 435
<211> LENGTH: 23
<212> TYPE: DNA
<213> ORGANISM: artificial sequence
<220> FEATURE:
<223> OTHER INFORMATION: The forward primer for SNP of specific position
      (chr21:16063848)

<400> SEQUENCE: 435
aagttggttg ctgcagtttt ctg                                         23

<210> SEQ ID NO 436
<211> LENGTH: 29
<212> TYPE: DNA
<213> ORGANISM: artificial sequence
<220> FEATURE:
<223> OTHER INFORMATION: The reverse primer for SNP of specific position
      (chr21:16063848)

<400> SEQUENCE: 436
agttttacag tcacctgctg ataatttga                                   29

<210> SEQ ID NO 437
<211> LENGTH: 22
<212> TYPE: DNA
```

<210> SEQ ID NO 437
<211> LENGTH: 22
<212> TYPE: DNA
<213> ORGANISM: artificial sequence
<220> FEATURE:
<223> OTHER INFORMATION: The forward primer for SNP of specific position (chr21:16122140)

<400> SEQUENCE: 437
gggaggcttt gataaaagcc ca                                    22

<210> SEQ ID NO 438
<211> LENGTH: 29
<212> TYPE: DNA
<213> ORGANISM: artificial sequence
<220> FEATURE:
<223> OTHER INFORMATION: The reverse primer for SNP of specific position (chr21:16122140)

<400> SEQUENCE: 438
cacatcattt actttgaaca cttctgtct                             29

<210> SEQ ID NO 439
<211> LENGTH: 22
<212> TYPE: DNA
<213> ORGANISM: artificial sequence
<220> FEATURE:
<223> OTHER INFORMATION: The forward primer for SNP of specific position (chr21:16160041)

<400> SEQUENCE: 439
tctacatggc ccatcagagg aa                                    22

<210> SEQ ID NO 440
<211> LENGTH: 30
<212> TYPE: DNA
<213> ORGANISM: artificial sequence
<220> FEATURE:
<223> OTHER INFORMATION: The reverse primer for SNP of specific position (chr21:16160041)

<400> SEQUENCE: 440
gggatgtaca tggacataat ataagccatg                            30

<210> SEQ ID NO 441
<211> LENGTH: 28
<212> TYPE: DNA
<213> ORGANISM: artificial sequence
<220> FEATURE:
<223> OTHER INFORMATION: The forward primer for SNP of specific position (chr21:16193235)

<400> SEQUENCE: 441
gcaatggttg aggaaatttc aaaatagc                              28

<210> SEQ ID NO 442
<211> LENGTH: 24
<212> TYPE: DNA
<213> ORGANISM: artificial sequence
<220> FEATURE:
<223> OTHER INFORMATION: The reverse primer for SNP of specific position (chr21:16193235)

<400> SEQUENCE: 442
gccaactgat gttccttaat ggca                                  24

<210> SEQ ID NO 443
<211> LENGTH: 27
<212> TYPE: DNA
<213> ORGANISM: artificial sequence

```
<220> FEATURE:
<223> OTHER INFORMATION: The forward primer for SNP of specific position
      (chr21:16238898)

<400> SEQUENCE: 443
ctgatccaat attactggca tccttct                                            27

<210> SEQ ID NO 444
<211> LENGTH: 28
<212> TYPE: DNA
<213> ORGANISM: artificial sequence
<220> FEATURE:
<223> OTHER INFORMATION: The reverse primer for SNP of specific position
      (chr21:16238898)

<400> SEQUENCE: 444
aagaaattga tcacatcaca gttctgga                                           28

<210> SEQ ID NO 445
<211> LENGTH: 26
<212> TYPE: DNA
<213> ORGANISM: artificial sequence
<220> FEATURE:
<223> OTHER INFORMATION: The forward primer for SNP of specific position
      (chr21:16315932)

<400> SEQUENCE: 445
cttgttggag acaaagtgaa taagcc                                             26

<210> SEQ ID NO 446
<211> LENGTH: 30
<212> TYPE: DNA
<213> ORGANISM: artificial sequence
<220> FEATURE:
<223> OTHER INFORMATION: The reverse primer for SNP of specific position
      (chr21:16315932)

<400> SEQUENCE: 446
aatgcttcag atttaggaag aattaggagt                                         30

<210> SEQ ID NO 447
<211> LENGTH: 28
<212> TYPE: DNA
<213> ORGANISM: artificial sequence
<220> FEATURE:
<223> OTHER INFORMATION: The forward primer for SNP of specific position
      (chr21:16353639)

<400> SEQUENCE: 447
agagtcaata aatctgacta ggtcccat                                           28

<210> SEQ ID NO 448
<211> LENGTH: 25
<212> TYPE: DNA
<213> ORGANISM: artificial sequence
<220> FEATURE:
<223> OTHER INFORMATION: The reverse primer for SNP of specific position
      (chr21:16353639)

<400> SEQUENCE: 448
ttggttgtat ggatagatgg gcaaa                                              25

<210> SEQ ID NO 449
<211> LENGTH: 30
<212> TYPE: DNA
<213> ORGANISM: artificial sequence
<220> FEATURE:
```

<223> OTHER INFORMATION: The forward primer for SNP of specific position
      (chr21:16384555)

<400> SEQUENCE: 449
catccttttt cctcccaatc attatctttg                                           30

<210> SEQ ID NO 450
<211> LENGTH: 25
<212> TYPE: DNA
<213> ORGANISM: artificial sequence
<220> FEATURE:
<223> OTHER INFORMATION: The reverse primer for SNP of specific position
      (chr21:16384555)

<400> SEQUENCE: 450
ggtcaaataa gcttgggaga tgttg                                                25

<210> SEQ ID NO 451
<211> LENGTH: 30
<212> TYPE: DNA
<213> ORGANISM: artificial sequence
<220> FEATURE:
<223> OTHER INFORMATION: The forward primer for SNP of specific position
      (chr21:16448591)

<400> SEQUENCE: 451 cctttcata ggcattgaaa aatcgttttc                                            30

<210> SEQ ID NO 452
<211> LENGTH: 30
<212> TYPE: DNA
<213> ORGANISM: artificial sequence
<220> FEATURE:
<223> OTHER INFORMATION: The reverse primer for SNP of specific position
      (chr21:16448591)

<400> SEQUENCE: 452
attgatggtg cattagagga aaaagatttg                                           30

<210> SEQ ID NO 453
<211> LENGTH: 29
<212> TYPE: DNA
<213> ORGANISM: artificial sequence
<220> FEATURE:
<223> OTHER INFORMATION: The forward primer for SNP of specific position
      (chr21:16578538)

<400> SEQUENCE: 453
tcagtttcct ccagatatac tctatggtc                                            29

<210> SEQ ID NO 454
<211> LENGTH: 22
<212> TYPE: DNA
<213> ORGANISM: artificial sequence
<220> FEATURE:
<223> OTHER INFORMATION: The reverse primer for SNP of specific position
      (chr21:16578538)

<400> SEQUENCE: 454
ggcagtcttg cctggttgat at                                                   22

<210> SEQ ID NO 455
<211> LENGTH: 30
<212> TYPE: DNA
<213> ORGANISM: artificial sequence
<220> FEATURE:
<223> OTHER INFORMATION: The forward primer for SNP of specific position (chr21:16645724)

<400> SEQUENCE: 455
tgaagaaaat aaatgcaatt gtgaatgcct                                    30

<210> SEQ ID NO 456
<211> LENGTH: 30
<212> TYPE: DNA
<213> ORGANISM: artificial sequence
<220> FEATURE:
<223> OTHER INFORMATION: The reverse primer for SNP of specific position
      (chr21:16645724)

<400> SEQUENCE: 456
cagagtaaga tgccttttat ttgctaaagt                                    30

<210> SEQ ID NO 457
<211> LENGTH: 28
<212> TYPE: DNA
<213> ORGANISM: artificial sequence
<220> FEATURE:
<223> OTHER INFORMATION: The forward primer for SNP of specific position
      (chr21:16717265)

<400> SEQUENCE: 457
actcagttct ttttccttga cttcttcc                                      28

<210> SEQ ID NO 458
<211> LENGTH: 26
<212> TYPE: DNA
<213> ORGANISM: artificial sequence
<220> FEATURE:
<223> OTHER INFORMATION: The reverse primer for SNP of specific position
      (chr21:16717265)

<400> SEQUENCE: 458
acactgactg attgaatttg tgtgga                                        26

<210> SEQ ID NO 459
<211> LENGTH: 29
<212> TYPE: DNA
<213> ORGANISM: artificial sequence
<220> FEATURE:
<223> OTHER INFORMATION: The forward primer for SNP of specific position
      (chr21:16833315)

<400> SEQUENCE: 459 gcaattttc tttctgaaag tctgaagct                                      29

<210> SEQ ID NO 460
<211> LENGTH: 29
<212> TYPE: DNA
<213> ORGANISM: artificial sequence
<220> FEATURE:
<223> OTHER INFORMATION: The reverse primer for SNP of specific position
      (chr21:16833315)

<400> SEQUENCE: 460
caaatgggat gctcatcttc tcaattttt                                     29

<210> SEQ ID NO 461
<211> LENGTH: 28
<212> TYPE: DNA
<213> ORGANISM: artificial sequence
<220> FEATURE:
<223> OTHER INFORMATION: The forward primer for SNP of specific position
      (chr21:16881542)

-continued

<210> SEQ ID NO 461

<400> SEQUENCE: 461
tcagccaggg aaataatttc tcttttct                                    28

<210> SEQ ID NO 462
<211> LENGTH: 22
<212> TYPE: DNA
<213> ORGANISM: artificial sequence
<220> FEATURE:
<223> OTHER INFORMATION: The reverse primer for SNP of specific position
      (chr21:16881542)

<400> SEQUENCE: 462
atcctccatc caagtaccct gt                                          22

<210> SEQ ID NO 463
<211> LENGTH: 30
<212> TYPE: DNA
<213> ORGANISM: artificial sequence
<220> FEATURE:
<223> OTHER INFORMATION: The forward primer for SNP of specific position
      (chr21:17000938)

<400> SEQUENCE: 463
gttatctgaa tccaaatacc tacacacaca                                  30

<210> SEQ ID NO 464
<211> LENGTH: 30
<212> TYPE: DNA
<213> ORGANISM: artificial sequence
<220> FEATURE:
<223> OTHER INFORMATION: The reverse primer for SNP of specific position
      (chr21:17000938)

<400> SEQUENCE: 464
cctctctcaa tggaaaattc agatgaattg                                  30

<210> SEQ ID NO 465
<211> LENGTH: 22
<212> TYPE: DNA
<213> ORGANISM: artificial sequence
<220> FEATURE:
<223> OTHER INFORMATION: The forward primer for SNP of specific position
      (chr21:17054831)

<400> SEQUENCE: 465
gatggagcag cttcctgtgt aa                                          22

<210> SEQ ID NO 466
<211> LENGTH: 26
<212> TYPE: DNA
<213> ORGANISM: artificial sequence
<220> FEATURE:
<223> OTHER INFORMATION: The reverse primer for SNP of specific position
      (chr21:17054831)

<400> SEQUENCE: 466
tttaggtgca attgtaagtc acagga                                      26

<210> SEQ ID NO 467
<211> LENGTH: 26
<212> TYPE: DNA
<213> ORGANISM: artificial sequence
<220> FEATURE:
<223> OTHER INFORMATION: The forward primer for SNP of specific position
      (chr21:17140290)

<400> SEQUENCE: 467
gtgaagcaag caggaaattg actaaa                                        26

<210> SEQ ID NO 468
<211> LENGTH: 30
<212> TYPE: DNA
<213> ORGANISM: artificial sequence
<220> FEATURE:
<223> OTHER INFORMATION: The reverse primer for SNP of specific position
      (chr21:17140290)

<400> SEQUENCE: 468
ttctccctaa gggaacctat tcaaaatttt                                    30

<210> SEQ ID NO 469
<211> LENGTH: 22
<212> TYPE: DNA
<213> ORGANISM: artificial sequence
<220> FEATURE:
<223> OTHER INFORMATION: The forward primer for SNP of specific position
      (chr21:17203891)

<400> SEQUENCE: 469
tgtgggtttc atggaatgtg gt                                            22

<210> SEQ ID NO 470
<211> LENGTH: 29
<212> TYPE: DNA
<213> ORGANISM: artificial sequence
<220> FEATURE:
<223> OTHER INFORMATION: The reverse primer for SNP of specific position
      (chr21:17203891)

<400> SEQUENCE: 470
tatgtacatt aaacagtatg cactggcat                                     29

<210> SEQ ID NO 471
<211> LENGTH: 26
<212> TYPE: DNA
<213> ORGANISM: artificial sequence
<220> FEATURE:
<223> OTHER INFORMATION: The forward primer for SNP of specific position
      (chr21:17295288)

<400> SEQUENCE: 471
tcatgggact cttatttcca ttgcaa                                        26

<210> SEQ ID NO 472
<211> LENGTH: 22
<212> TYPE: DNA
<213> ORGANISM: artificial sequence
<220> FEATURE:
<223> OTHER INFORMATION: The reverse primer for SNP of specific position
      (chr21:17295288)

<400> SEQUENCE: 472
cccagaggta gccatgtgac ta                                            22

<210> SEQ ID NO 473
<211> LENGTH: 28
<212> TYPE: DNA
<213> ORGANISM: artificial sequence
<220> FEATURE:
<223> OTHER INFORMATION: The forward primer for SNP of specific position
      (chr21:17340912)

<400> SEQUENCE: 473
aaaagacaaa gaaagcaaat gtggaaca                                       28

<210> SEQ ID NO 474
<211> LENGTH: 28
<212> TYPE: DNA
<213> ORGANISM: artificial sequence
<220> FEATURE:
<223> OTHER INFORMATION: The reverse primer for SNP of specific position
      (chr21:17340912)

<400> SEQUENCE: 474
cttccacctc tgaaacatag taagctac                                       28

<210> SEQ ID NO 475
<211> LENGTH: 30
<212> TYPE: DNA
<213> ORGANISM: artificial sequence
<220> FEATURE:
<223> OTHER INFORMATION: The forward primer for SNP of specific position
      (chr21:17536247)

<400> SEQUENCE: 475
ccctcagact tttcttgtaa atcctatagg                                     30

<210> SEQ ID NO 476
<211> LENGTH: 24
<212> TYPE: DNA
<213> ORGANISM: artificial sequence
<220> FEATURE:
<223> OTHER INFORMATION: The reverse primer for SNP of specific position
      (chr21:17536247)

<400> SEQUENCE: 476
ctcagtgagt gaagccatac gata                                           24

<210> SEQ ID NO 477
<211> LENGTH: 26
<212> TYPE: DNA
<213> ORGANISM: artificial sequence
<220> FEATURE:
<223> OTHER INFORMATION: The forward primer for SNP of specific position
      (chr21:17640426)

<400> SEQUENCE: 477
gggagtaaat ggtctttagg gatcat                                         26

<210> SEQ ID NO 478
<211> LENGTH: 25
<212> TYPE: DNA
<213> ORGANISM: artificial sequence
<220> FEATURE:
<223> OTHER INFORMATION: The reverse primer for SNP of specific position
      (chr21:17640426)

<400> SEQUENCE: 478
agggcagtgg aagtaaaacc ttttt                                          25

<210> SEQ ID NO 479
<211> LENGTH: 30
<212> TYPE: DNA
<213> ORGANISM: artificial sequence
<220> FEATURE:
<223> OTHER INFORMATION: The forward primer for SNP of specific position
      (chr21:17673255)

<400> SEQUENCE: 479
tgttatatcc cacatctcat ttctgagaga                                              30

<210> SEQ ID NO 480
<211> LENGTH: 23
<212> TYPE: DNA
<213> ORGANISM: artificial sequence
<220> FEATURE:
<223> OTHER INFORMATION: The reverse primer for SNP of specific position
      (chr21:17673255)

<400> SEQUENCE: 480
gaaaggccag gagaaaaggt ctt                                                     23

<210> SEQ ID NO 481
<211> LENGTH: 30
<212> TYPE: DNA
<213> ORGANISM: artificial sequence
<220> FEATURE:
<223> OTHER INFORMATION: The forward primer for SNP of specific position
      (chr21:17713264)

<400> SEQUENCE: 481
tgataaattt ttcagatcct tcaccactct                                              30

<210> SEQ ID NO 482
<211> LENGTH: 30
<212> TYPE: DNA
<213> ORGANISM: artificial sequence
<220> FEATURE:
<223> OTHER INFORMATION: The reverse primer for SNP of specific position
      (chr21:17713264)

<400> SEQUENCE: 482
tccaagttct tttctgttca ccttattgat                                              30

<210> SEQ ID NO 483
<211> LENGTH: 22
<212> TYPE: DNA
<213> ORGANISM: artificial sequence
<220> FEATURE:
<223> OTHER INFORMATION: The forward primer for SNP of specific position
      (chr21:17748703)

<400> SEQUENCE: 483
ctagtcctcc caacttgctt gt                                                      22

<210> SEQ ID NO 484
<211> LENGTH: 22
<212> TYPE: DNA
<213> ORGANISM: artificial sequence
<220> FEATURE:
<223> OTHER INFORMATION: The reverse primer for SNP of specific position
      (chr21:17748703)

<400> SEQUENCE: 484
gtaacattga gcagcagcaa ca                                                      22

<210> SEQ ID NO 485
<211> LENGTH: 24
<212> TYPE: DNA
<213> ORGANISM: artificial sequence
<220> FEATURE:
<223> OTHER INFORMATION: The forward primer for SNP of specific position
      (chr21:17781159)

<400> SEQUENCE: 485
atctggccag atgaaaatgg gatt                                                    24

<210> SEQ ID NO 486
<211> LENGTH: 24
<212> TYPE: DNA
<213> ORGANISM: artificial sequence
<220> FEATURE:
<223> OTHER INFORMATION: The reverse primer for SNP of specific position
      (chr21:17781159)

<400> SEQUENCE: 486
ccctactgcg tttaacaacc aatc                                              24

<210> SEQ ID NO 487
<211> LENGTH: 30
<212> TYPE: DNA
<213> ORGANISM: artificial sequence
<220> FEATURE:
<223> OTHER INFORMATION: The forward primer for SNP of specific position
      (chr21:17823782)

<400> SEQUENCE: 487
tggagtttat caccaagtca ttttatgtcc                                        30

<210> SEQ ID NO 488
<211> LENGTH: 29
<212> TYPE: DNA
<213> ORGANISM: artificial sequence
<220> FEATURE:
<223> OTHER INFORMATION: The reverse primer for SNP of specific position
      (chr21:17823782)

<400> SEQUENCE: 488
acagaaagag cttgtaattc ttcctttca                                         29

<210> SEQ ID NO 489
<211> LENGTH: 24
<212> TYPE: DNA
<213> ORGANISM: artificial sequence
<220> FEATURE:
<223> OTHER INFORMATION: The forward primer for SNP of specific position
      (chr21:18003355)

<400> SEQUENCE: 489
cttcacagaa tgggataact gcct                                              24

<210> SEQ ID NO 490
<211> LENGTH: 23
<212> TYPE: DNA
<213> ORGANISM: artificial sequence
<220> FEATURE:
<223> OTHER INFORMATION: The reverse primer for SNP of specific position
      (chr21:18003355)

<400> SEQUENCE: 490
cctgacacat tctgcattcc cat                                               23

<210> SEQ ID NO 491
<211> LENGTH: 29
<212> TYPE: DNA
<213> ORGANISM: artificial sequence
<220> FEATURE:
<223> OTHER INFORMATION: The forward primer for SNP of specific position
      (chr21:18046650)

<400> SEQUENCE: 491
actttgttcc ctgaatataa agagcaagt                                         29

<210> SEQ ID NO 492
<211> LENGTH: 28
<212> TYPE: DNA
<213> ORGANISM: artificial sequence
<220> FEATURE:
<223> OTHER INFORMATION: The reverse primer for SNP of specific position
      (chr21:18046650)

<400> SEQUENCE: 492
gtatcttaga tattcccagc tttgtgca                                        28

<210> SEQ ID NO 493
<211> LENGTH: 29
<212> TYPE: DNA
<213> ORGANISM: artificial sequence
<220> FEATURE:
<223> OTHER INFORMATION: The forward primer for SNP of specific position
      (chr21:18114449)

<400> SEQUENCE: 493
cgaagggctt tgtctagata aacataaca                                       29

<210> SEQ ID NO 494
<211> LENGTH: 22
<212> TYPE: DNA
<213> ORGANISM: artificial sequence
<220> FEATURE:
<223> OTHER INFORMATION: The reverse primer for SNP of specific position
      (chr21:18114449)

<400> SEQUENCE: 494
gtggatgaga ggtgtggatc tt                                              22

<210> SEQ ID NO 495
<211> LENGTH: 22
<212> TYPE: DNA
<213> ORGANISM: artificial sequence
<220> FEATURE:
<223> OTHER INFORMATION: The forward primer for SNP of specific position
      (chr21:18151760)

<400> SEQUENCE: 495
cccactgacc aaatctggac at                                              22

<210> SEQ ID NO 496
<211> LENGTH: 27
<212> TYPE: DNA
<213> ORGANISM: artificial sequence
<220> FEATURE:
<223> OTHER INFORMATION: The reverse primer for SNP of specific position
      (chr21:18151760)

<400> SEQUENCE: 496
ggacattctt tgacactctg aaatagc                                         27

<210> SEQ ID NO 497
<211> LENGTH: 27
<212> TYPE: DNA
<213> ORGANISM: artificial sequence
<220> FEATURE:
<223> OTHER INFORMATION: The forward primer for SNP of specific position
      (chr21:18182817)

<400> SEQUENCE: 497
ttgtttgtag tgactacaca actcagt                                         27

```
<210> SEQ ID NO 498
<211> LENGTH: 27
<212> TYPE: DNA
<213> ORGANISM: artificial sequence
<220> FEATURE:
<223> OTHER INFORMATION: The reverse primer for SNP of specific position
      (chr21:18182817)

<400> SEQUENCE: 498
ctgacagaaa attttccaac agctgtt                                          27

<210> SEQ ID NO 499
<211> LENGTH: 28
<212> TYPE: DNA
<213> ORGANISM: artificial sequence
<220> FEATURE:
<223> OTHER INFORMATION: The forward primer for SNP of specific position
      (chr21:18250262)

<400> SEQUENCE: 499
cctgaaaaat atgtggatca accgaaaa                                         28

<210> SEQ ID NO 500
<211> LENGTH: 30
<212> TYPE: DNA
<213> ORGANISM: artificial sequence
<220> FEATURE:
<223> OTHER INFORMATION: The reverse primer for SNP of specific position
      (chr21:18250262)

<400> SEQUENCE: 500
gaaaagagaa acatcaagag tcagttttgg                                       30

<210> SEQ ID NO 501
<211> LENGTH: 24
<212> TYPE: DNA
<213> ORGANISM: artificial sequence
<220> FEATURE:
<223> OTHER INFORMATION: The forward primer for SNP of specific position
      (chr21:18337678)

<400> SEQUENCE: 501
gctcattctc attttggct tcca                                              24

<210> SEQ ID NO 502
<211> LENGTH: 24
<212> TYPE: DNA
<213> ORGANISM: artificial sequence
<220> FEATURE:
<223> OTHER INFORMATION: The reverse primer for SNP of specific position
      (chr21:18337678)

<400> SEQUENCE: 502
ctacagaata ccactcagct gcaa                                             24

<210> SEQ ID NO 503
<211> LENGTH: 28
<212> TYPE: DNA
<213> ORGANISM: artificial sequence
<220> FEATURE:
<223> OTHER INFORMATION: The forward primer for SNP of specific position
      (chr21:18385770)

<400> SEQUENCE: 503
tgaggaggat acttctgtta ttccatca                                         28

<210> SEQ ID NO 504
```

```
<211> LENGTH: 27
<212> TYPE: DNA
<213> ORGANISM: artificial sequence
<220> FEATURE:
<223> OTHER INFORMATION: The reverse primer for SNP of specific position
      (chr21:18385770)

<400> SEQUENCE: 504
ccctttcttt cctgaaaata agtgcag                                         27

<210> SEQ ID NO 505
<211> LENGTH: 24
<212> TYPE: DNA
<213> ORGANISM: artificial sequence
<220> FEATURE:
<223> OTHER INFORMATION: The forward primer for SNP of specific position
      (chr21:18420873)

<400> SEQUENCE: 505
cccacctcca aattgtatcc catt                                            24

<210> SEQ ID NO 506
<211> LENGTH: 30
<212> TYPE: DNA
<213> ORGANISM: artificial sequence
<220> FEATURE:
<223> OTHER INFORMATION: The reverse primer for SNP of specific position
      (chr21:18420873)

<400> SEQUENCE: 506
agtactggtt gtgcattatt aaatatgcaa                                      30

<210> SEQ ID NO 507
<211> LENGTH: 24
<212> TYPE: DNA
<213> ORGANISM: artificial sequence
<220> FEATURE:
<223> OTHER INFORMATION: The forward primer for SNP of specific position
      (chr21:18457287)

<400> SEQUENCE: 507
actgcactca atgaaaccat ctga                                            24

<210> SEQ ID NO 508
<211> LENGTH: 30
<212> TYPE: DNA
<213> ORGANISM: artificial sequence
<220> FEATURE:
<223> OTHER INFORMATION: The reverse primer for SNP of specific position
      (chr21:18457287)

<400> SEQUENCE: 508
ggatttgcct ttaatactca gggatacaat                                      30

<210> SEQ ID NO 509
<211> LENGTH: 30
<212> TYPE: DNA
<213> ORGANISM: artificial sequence
<220> FEATURE:
<223> OTHER INFORMATION: The forward primer for SNP of specific position
      (chr21:18586049)

<400> SEQUENCE: 509
accatgtttt aactcttctt ttaaagctgt                                      30

<210> SEQ ID NO 510
<211> LENGTH: 30
```

<212> TYPE: DNA
<213> ORGANISM: artificial sequence
<220> FEATURE:
<223> OTHER INFORMATION: The reverse primer for SNP of specific position
    (chr21:18586049)

<400> SEQUENCE: 510
gtcaaaccag cttaagttta aaaagccata                              30

<210> SEQ ID NO 511
<211> LENGTH: 26
<212> TYPE: DNA
<213> ORGANISM: artificial sequence
<220> FEATURE:
<223> OTHER INFORMATION: The forward primer for SNP of specific position
    (chr21:18650837)

<400> SEQUENCE: 511
gagcatgttt cctgaacaat cattgg                                  26

<210> SEQ ID NO 512
<211> LENGTH: 28
<212> TYPE: DNA
<213> ORGANISM: artificial sequence
<220> FEATURE:
<223> OTHER INFORMATION: The reverse primer for SNP of specific position
    (chr21:18650837)

<400> SEQUENCE: 512
tttttgttgt tgtagattgt tgttgctg                                28

<210> SEQ ID NO 513
<211> LENGTH: 30
<212> TYPE: DNA
<213> ORGANISM: artificial sequence
<220> FEATURE:
<223> OTHER INFORMATION: The forward primer for SNP of specific position
    (chr21:18740886)

<400> SEQUENCE: 513
agatgtatta ccttcatagt ctctgggttt                              30

<210> SEQ ID NO 514
<211> LENGTH: 23
<212> TYPE: DNA
<213> ORGANISM: artificial sequence
<220> FEATURE:
<223> OTHER INFORMATION: The reverse primer for SNP of specific position
    (chr21:18740886)

<400> SEQUENCE: 514
tgtggttcct cagctgtcaa atc                                     23

<210> SEQ ID NO 515
<211> LENGTH: 23
<212> TYPE: DNA
<213> ORGANISM: artificial sequence
<220> FEATURE:
<223> OTHER INFORMATION: The forward primer for SNP of specific position
    (chr21:18858018)

<400> SEQUENCE: 515
caaccaatca agcagcagtg aat                                     23

<210> SEQ ID NO 516
<211> LENGTH: 22
<212> TYPE: DNA

```
<213> ORGANISM: artificial sequence
<220> FEATURE:
<223> OTHER INFORMATION: The reverse primer for SNP of specific position
      (chr21:18858018)

<400> SEQUENCE: 516
ggtgcaggga cagccttttt at                                                  22

<210> SEQ ID NO 517
<211> LENGTH: 23
<212> TYPE: DNA
<213> ORGANISM: artificial sequence
<220> FEATURE:
<223> OTHER INFORMATION: The forward primer for SNP of specific position
      (chr21:18936951)

<400> SEQUENCE: 517
tggtttgttg gcttcacaga tgt                                                 23

<210> SEQ ID NO 518
<211> LENGTH: 30
<212> TYPE: DNA
<213> ORGANISM: artificial sequence
<220> FEATURE:
<223> OTHER INFORMATION: The reverse primer for SNP of specific position
      (chr21:18936951)

<400> SEQUENCE: 518
gctgaaaaca ctacagattt aagtttgctg                                          30

<210> SEQ ID NO 519
<211> LENGTH: 28
<212> TYPE: DNA
<213> ORGANISM: artificial sequence
<220> FEATURE:
<223> OTHER INFORMATION: The forward primer for SNP of specific position
      (chr21:19002939)

<400> SEQUENCE: 519
tcctgtcatt tcactcctac atacttca                                            28

<210> SEQ ID NO 520
<211> LENGTH: 28
<212> TYPE: DNA
<213> ORGANISM: artificial sequence
<220> FEATURE:
<223> OTHER INFORMATION: The reverse primer for SNP of specific position
      (chr21:19002939)

<400> SEQUENCE: 520
aagaaggaag aaggaagtct tctctaca                                            28

<210> SEQ ID NO 521
<211> LENGTH: 22
<212> TYPE: DNA
<213> ORGANISM: artificial sequence
<220> FEATURE:
<223> OTHER INFORMATION: The forward primer for SNP of specific position
      (chr21:19064396)

<400> SEQUENCE: 521
cggtgcatta ggaagccaag tt                                                  22

<210> SEQ ID NO 522
<211> LENGTH: 30
<212> TYPE: DNA
<213> ORGANISM: artificial sequence
```

<220> FEATURE:
<223> OTHER INFORMATION: The reverse primer for SNP of specific position
      (chr21:19064396)

<400> SEQUENCE: 522
cacatgaata tccaaatgtc caattgtcat                                    30

<210> SEQ ID NO 523
<211> LENGTH: 26
<212> TYPE: DNA
<213> ORGANISM: artificial sequence
<220> FEATURE:
<223> OTHER INFORMATION: The forward primer for SNP of specific position
      (chr21:19139888)

<400> SEQUENCE: 523
gccctacctc ctaatacaac catatc                                        26

<210> SEQ ID NO 524
<211> LENGTH: 22
<212> TYPE: DNA
<213> ORGANISM: artificial sequence
<220> FEATURE:
<223> OTHER INFORMATION: The reverse primer for SNP of specific position
      (chr21:19139888)

<400> SEQUENCE: 524
cttttcaggt gcaccgtctt tg                                            22

<210> SEQ ID NO 525
<211> LENGTH: 26
<212> TYPE: DNA
<213> ORGANISM: artificial sequence
<220> FEATURE:
<223> OTHER INFORMATION: The forward primer for SNP of specific position
      (chr21:19254923)

<400> SEQUENCE: 525
gcctggcctc tgtttgtctt ttataa                                        26

<210> SEQ ID NO 526
<211> LENGTH: 28
<212> TYPE: DNA
<213> ORGANISM: artificial sequence
<220> FEATURE:
<223> OTHER INFORMATION: The reverse primer for SNP of specific position
      (chr21:19254923)

<400> SEQUENCE: 526
gtactcttat taatgcctcc tttggtca                                      28

<210> SEQ ID NO 527
<211> LENGTH: 26
<212> TYPE: DNA
<213> ORGANISM: artificial sequence
<220> FEATURE:
<223> OTHER INFORMATION: The forward primer for SNP of specific position
      (chr21:19316600)

<400> SEQUENCE: 527
ctgcttgact ttagaaggat gatgga                                        26

<210> SEQ ID NO 528
<211> LENGTH: 22
<212> TYPE: DNA
<213> ORGANISM: artificial sequence
<220> FEATURE:

```
<223> OTHER INFORMATION: The reverse primer for SNP of specific position
      (chr21:19316600)

<400> SEQUENCE: 528
ggctggtgta gagccactta ac                                              22

<210> SEQ ID NO 529
<211> LENGTH: 22
<212> TYPE: DNA
<213> ORGANISM: artificial sequence
<220> FEATURE:
<223> OTHER INFORMATION: The forward primer for SNP of specific position
      (chr22:16415691)

<400> SEQUENCE: 529
cagccatttt tcacgttgca gt                                              22

<210> SEQ ID NO 530
<211> LENGTH: 23
<212> TYPE: DNA
<213> ORGANISM: artificial sequence
<220> FEATURE:
<223> OTHER INFORMATION: The reverse primer for SNP of specific position
      (chr22:16415691)

<400> SEQUENCE: 530
ccctggagaa agcagttctt tac                                             23

<210> SEQ ID NO 531
<211> LENGTH: 24
<212> TYPE: DNA
<213> ORGANISM: artificial sequence
<220> FEATURE:
<223> OTHER INFORMATION: The forward primer for SNP of specific position
      (chr22:16554800)

<400> SEQUENCE: 531
ctaattgagg gacagacact caca                                            24

<210> SEQ ID NO 532
<211> LENGTH: 25
<212> TYPE: DNA
<213> ORGANISM: artificial sequence
<220> FEATURE:
<223> OTHER INFORMATION: The reverse primer for SNP of specific position
      (chr22:16554800)

<400> SEQUENCE: 532
gctactggat tctgagtgtg tgttc                                           25

<210> SEQ ID NO 533
<211> LENGTH: 30
<212> TYPE: DNA
<213> ORGANISM: artificial sequence
<220> FEATURE:
<223> OTHER INFORMATION: The forward primer for SNP of specific position
      (chr22:16848067)

<400> SEQUENCE: 533
tcgaatggag ttgaatggaa ttatcaaaga                                      30

<210> SEQ ID NO 534
<211> LENGTH: 30
<212> TYPE: DNA
<213> ORGANISM: artificial sequence
<220> FEATURE:
<223> OTHER INFORMATION: The reverse primer for SNP of specific position
```

(chr22:16848067)

<400> SEQUENCE: 534
catttgtgtc cattctatga ttccatttca                               30

<210> SEQ ID NO 535
<211> LENGTH: 29
<212> TYPE: DNA
<213> ORGANISM: artificial sequence
<220> FEATURE:
<223> OTHER INFORMATION: The forward primer for SNP of specific position
      (chr22:16850056)

<400> SEQUENCE: 535
gaataatcaa atggagacga atggaatcc                                29

<210> SEQ ID NO 536
<211> LENGTH: 29
<212> TYPE: DNA
<213> ORGANISM: artificial sequence
<220> FEATURE:
<223> OTHER INFORMATION: The reverse primer for SNP of specific position
      (chr22:16850056)

<400> SEQUENCE: 536
ctattcggtg attacattcg attgcattt                                29

<210> SEQ ID NO 537
<211> LENGTH: 32
<212> TYPE: DNA
<213> ORGANISM: artificial sequence
<220> FEATURE:
<223> OTHER INFORMATION: The forward primer for SNP of specific position
      (chr22:16850858)

<400> SEQUENCE: 537
agaatcgaat ggaataatca tcgaatgtac ta                            32

<210> SEQ ID NO 538
<211> LENGTH: 33
<212> TYPE: DNA
<213> ORGANISM: artificial sequence
<220> FEATURE:
<223> OTHER INFORMATION: The reverse primer for SNP of specific position
      (chr22:16850858)

<400> SEQUENCE: 538
atttttccat ttgataccat tcgatgatga ttc                           33

<210> SEQ ID NO 539
<211> LENGTH: 26
<212> TYPE: DNA
<213> ORGANISM: artificial sequence
<220> FEATURE:
<223> OTHER INFORMATION: The forward primer for SNP of specific position
      (chr22:16851557)

<400> SEQUENCE: 539
ctaagggaat aatcgaacgg actcaa                                   26

<210> SEQ ID NO 540
<211> LENGTH: 30
<212> TYPE: DNA
<213> ORGANISM: artificial sequence
<220> FEATURE:
<223> OTHER INFORMATION: The reverse primer for SNP of specific position
      (chr22:16851557)

```
<400> SEQUENCE: 540
tcgatttctc catttaattc cattcgatga                                    30

<210> SEQ ID NO 541
<211> LENGTH: 27
<212> TYPE: DNA
<213> ORGANISM: artificial sequence
<220> FEATURE:
<223> OTHER INFORMATION: The forward primer for SNP of specific position
      (chr22:16852464)

<400> SEQUENCE: 541
tggaatcatc gaatgtcatt gaatgga                                       27

<210> SEQ ID NO 542
<211> LENGTH: 30
<212> TYPE: DNA
<213> ORGANISM: artificial sequence
<220> FEATURE:
<223> OTHER INFORMATION: The reverse primer for SNP of specific position
      (chr22:16852464)

<400> SEQUENCE: 542
tagtctattc gatgattcca ttcgagtcta                                    30

<210> SEQ ID NO 543
<211> LENGTH: 28
<212> TYPE: DNA
<213> ORGANISM: artificial sequence
<220> FEATURE:
<223> OTHER INFORMATION: The forward primer for SNP of specific position
      (chr22:16852792)

<400> SEQUENCE: 543
cgaaaggaat catcttcaaa aggaagtg                                      28

<210> SEQ ID NO 544
<211> LENGTH: 27
<212> TYPE: DNA
<213> ORGANISM: artificial sequence
<220> FEATURE:
<223> OTHER INFORMATION: The reverse primer for SNP of specific position
      (chr22:16852792)

<400> SEQUENCE: 544
ccattcgatt ccaaaagatg attccct                                       27

<210> SEQ ID NO 545
<211> LENGTH: 30
<212> TYPE: DNA
<213> ORGANISM: artificial sequence
<220> FEATURE:
<223> OTHER INFORMATION: The forward primer for SNP of specific position
      (chr22:16853453)

<400> SEQUENCE: 545
aatggaatca tcatgaatgg aatcaaaagg                                    30

<210> SEQ ID NO 546
<211> LENGTH: 27
<212> TYPE: DNA
<213> ORGANISM: artificial sequence
<220> FEATURE:
<223> OTHER INFORMATION: The reverse primer for SNP of specific position
      (chr22:16853453)
```

```
<400> SEQUENCE: 546
ccattcgagt ccattcaaca atgattg                                      27

<210> SEQ ID NO 547
<211> LENGTH: 30
<212> TYPE: DNA
<213> ORGANISM: artificial sequence
<220> FEATURE:
<223> OTHER INFORMATION: The forward primer for SNP of specific position
      (chr22:16854397)

<400> SEQUENCE: 547
gaaatcaaat ggaatcaatg aatggactca                                   30

<210> SEQ ID NO 548
<211> LENGTH: 30
<212> TYPE: DNA
<213> ORGANISM: artificial sequence
<220> FEATURE:
<223> OTHER INFORMATION: The reverse primer for SNP of specific position
      (chr22:16854397)

<400> SEQUENCE: 548
gattcaattc gatgatgatt tgattggagt                                   30

<210> SEQ ID NO 549
<211> LENGTH: 27
<212> TYPE: DNA
<213> ORGANISM: artificial sequence
<220> FEATURE:
<223> OTHER INFORMATION: The forward primer for SNP of specific position
      (chr22:16855647)

<400> SEQUENCE: 549
cacgaatgga atcatcactg aatgaag                                      27

<210> SEQ ID NO 550
<211> LENGTH: 30
<212> TYPE: DNA
<213> ORGANISM: artificial sequence
<220> FEATURE:
<223> OTHER INFORMATION: The reverse primer for SNP of specific position
      (chr22:16855647)

<400> SEQUENCE: 550
cgattccatt tgattaggat tcaattccag                                   30

<210> SEQ ID NO 551
<211> LENGTH: 26
<212> TYPE: DNA
<213> ORGANISM: artificial sequence
<220> FEATURE:
<223> OTHER INFORMATION: The forward primer for SNP of specific position
      (chr22:16856500)

<400> SEQUENCE: 551
agaatcgaac cgaatggaat catctt                                       26

<210> SEQ ID NO 552
<211> LENGTH: 30
<212> TYPE: DNA
<213> ORGANISM: artificial sequence
<220> FEATURE:
<223> OTHER INFORMATION: The reverse primer for SNP of specific position
      (chr22:16856500)

<400> SEQUENCE: 552
```
ggtgattaca ttgaattcct ttcgatgatg 30

<210> SEQ ID NO 553
<211> LENGTH: 33
<212> TYPE: DNA
<213> ORGANISM: artificial sequence
<220> FEATURE:
<223> OTHER INFORMATION: The forward primer for SNP of specific position (chr22:16857432)

<400> SEQUENCE: 553
tggaatcatc atcaaatagt atcgaaagga atc 33

<210> SEQ ID NO 554
<211> LENGTH: 33
<212> TYPE: DNA
<213> ORGANISM: artificial sequence
<220> FEATURE:
<223> OTHER INFORMATION: The reverse primer for SNP of specific position (chr22:16857432)

<400> SEQUENCE: 554
tcaattccat ttgataatta ttccattcga ttc 33

<210> SEQ ID NO 555
<211> LENGTH: 27
<212> TYPE: DNA
<213> ORGANISM: artificial sequence
<220> FEATURE:
<223> OTHER INFORMATION: The forward primer for SNP of specific position (chr22:16858287)

<400> SEQUENCE: 555
aaatgtaatc caatggaatc ctcgact 27

<210> SEQ ID NO 556
<211> LENGTH: 29
<212> TYPE: DNA
<213> ORGANISM: artificial sequence
<220> FEATURE:
<223> OTHER INFORMATION: The reverse primer for SNP of specific position (chr22:16858287)

<400> SEQUENCE: 556
cattcgattc ctttcgagga ttttattca 29

<210> SEQ ID NO 557
<211> LENGTH: 30
<212> TYPE: DNA
<213> ORGANISM: artificial sequence
<220> FEATURE:
<223> OTHER INFORMATION: The forward primer for SNP of specific position (chr22:16860547)

<400> SEQUENCE: 557
aatcattgaa tggaatcaaa cagaatcgtc 30

<210> SEQ ID NO 558
<211> LENGTH: 23
<212> TYPE: DNA
<213> ORGANISM: artificial sequence
<220> FEATURE:
<223> OTHER INFORMATION: The reverse primer for SNP of specific position (chr22:16860547)

<400> SEQUENCE: 558

```
ttggtgactc catttgacac cat                                          23
```

<210> SEQ ID NO 559
<211> LENGTH: 30
<212> TYPE: DNA
<213> ORGANISM: artificial sequence
<220> FEATURE:
<223> OTHER INFORMATION: The forward primer for SNP of specific position
      (chr22:16861742)

<400> SEQUENCE: 559

```
tcgaatggaa tcatccaatg aagtctaatg                                   30
```

<210> SEQ ID NO 560
<211> LENGTH: 25
<212> TYPE: DNA
<213> ORGANISM: artificial sequence
<220> FEATURE:
<223> OTHER INFORMATION: The reverse primer for SNP of specific position
      (chr22:16861742)

<400> SEQUENCE: 560

```
ctccgatcca tgattccatt cgatt                                        25
```

<210> SEQ ID NO 561
<211> LENGTH: 19
<212> TYPE: DNA
<213> ORGANISM: artificial sequence
<220> FEATURE:
<223> OTHER INFORMATION: The forward primer for SNP of specific position
      (chr22:16867995)

<400> SEQUENCE: 561

```
gctggccacg gcttttttac                                              19
```

<210> SEQ ID NO 562
<211> LENGTH: 19
<212> TYPE: DNA
<213> ORGANISM: artificial sequence
<220> FEATURE:
<223> OTHER INFORMATION: The reverse primer for SNP of specific position
      (chr22:16867995)

<400> SEQUENCE: 562

```
cgggtgtgca aaaatccgc                                               19
```

<210> SEQ ID NO 563
<211> LENGTH: 28
<212> TYPE: DNA
<213> ORGANISM: artificial sequence
<220> FEATURE:
<223> OTHER INFORMATION: The forward primer for SNP of specific position
      (chr22:17031697)

<400> SEQUENCE: 563

```
ccactaaaca gagattctgg attcaagg                                     28
```

<210> SEQ ID NO 564
<211> LENGTH: 30
<212> TYPE: DNA
<213> ORGANISM: artificial sequence
<220> FEATURE:
<223> OTHER INFORMATION: The reverse primer for SNP of specific position
      (chr22:17031697)

<400> SEQUENCE: 564

```
gcgtctcaac tttatgtacc ttaggtaaac                                   30
```

<210> SEQ ID NO 565
<211> LENGTH: 23
<212> TYPE: DNA
<213> ORGANISM: artificial sequence
<220> FEATURE:
<223> OTHER INFORMATION: The forward primer for SNP of specific position
      (chr22:17271213)

<400> SEQUENCE: 565
cactgcacta accctaggca ata                                          23

<210> SEQ ID NO 566
<211> LENGTH: 24
<212> TYPE: DNA
<213> ORGANISM: artificial sequence
<220> FEATURE:
<223> OTHER INFORMATION: The reverse primer for SNP of specific position
      (chr22:17271213)

<400> SEQUENCE: 566
tttttctgcg tggaagcttt ctag                                         24

<210> SEQ ID NO 567
<211> LENGTH: 27
<212> TYPE: DNA
<213> ORGANISM: artificial sequence
<220> FEATURE:
<223> OTHER INFORMATION: The forward primer for SNP of specific position
      (chr22:17293257)

<400> SEQUENCE: 567
cacttcctcc agttttcct acataga                                       27

<210> SEQ ID NO 568
<211> LENGTH: 30
<212> TYPE: DNA
<213> ORGANISM: artificial sequence
<220> FEATURE:
<223> OTHER INFORMATION: The reverse primer for SNP of specific position
      (chr22:17293257)

<400> SEQUENCE: 568
gcaagtgtgt actttaaaat ggctaatgtt                                   30

<210> SEQ ID NO 569
<211> LENGTH: 30
<212> TYPE: DNA
<213> ORGANISM: artificial sequence
<220> FEATURE:
<223> OTHER INFORMATION: The forward primer for SNP of specific position
      (chr22:17409957)

<400> SEQUENCE: 569
cttgtttcct tgtcattatc ttaggagtca                                   30

<210> SEQ ID NO 570
<211> LENGTH: 23
<212> TYPE: DNA
<213> ORGANISM: artificial sequence
<220> FEATURE:
<223> OTHER INFORMATION: The reverse primer for SNP of specific position
      (chr22:17409957)

<400> SEQUENCE: 570
acagaagtca gtgaggagtg tga                                          23

<210> SEQ ID NO 571
<211> LENGTH: 25
<212> TYPE: DNA
<213> ORGANISM: artificial sequence
<220> FEATURE:
<223> OTHER INFORMATION: The forward primer for SNP of specific position
      (chr22:17442318)

<400> SEQUENCE: 571
tttttggagg aggaaagtct gttca                                          25

<210> SEQ ID NO 572
<211> LENGTH: 25
<212> TYPE: DNA
<213> ORGANISM: artificial sequence
<220> FEATURE:
<223> OTHER INFORMATION: The reverse primer for SNP of specific position
      (chr22:17442318)

<400> SEQUENCE: 572
cacattggac tcaaacttgg ctatg                                          25

<210> SEQ ID NO 573
<211> LENGTH: 23
<212> TYPE: DNA
<213> ORGANISM: artificial sequence
<220> FEATURE:
<223> OTHER INFORMATION: The forward primer for SNP of specific position
      (chr22:17469090)

<400> SEQUENCE: 573
ctaccttgca tgttctgctc tct                                            23

<210> SEQ ID NO 574
<211> LENGTH: 22
<212> TYPE: DNA
<213> ORGANISM: artificial sequence
<220> FEATURE:
<223> OTHER INFORMATION: The reverse primer for SNP of specific position
      (chr22:17469090)

<400> SEQUENCE: 574
cctctagcag cccactttag ga                                             22

<210> SEQ ID NO 575
<211> LENGTH: 24
<212> TYPE: DNA
<213> ORGANISM: artificial sequence
<220> FEATURE:
<223> OTHER INFORMATION: The forward primer for SNP of specific position
      (chr22:17525677)

<400> SEQUENCE: 575
cttacagcag ggaacaaagt tcac                                           24

<210> SEQ ID NO 576
<211> LENGTH: 22
<212> TYPE: DNA
<213> ORGANISM: artificial sequence
<220> FEATURE:
<223> OTHER INFORMATION: The reverse primer for SNP of specific position
      (chr22:17525677)

<400> SEQUENCE: 576
cgggttccaa tctgggtttc aa                                             22

```
<210> SEQ ID NO 577
<211> LENGTH: 22
<212> TYPE: DNA
<213> ORGANISM: artificial sequence
<220> FEATURE:
<223> OTHER INFORMATION: The forward primer for SNP of specific position
      (chr22:17563259)

<400> SEQUENCE: 577
cctgggcact agacatagca ac                                              22

<210> SEQ ID NO 578
<211> LENGTH: 26
<212> TYPE: DNA
<213> ORGANISM: artificial sequence
<220> FEATURE:
<223> OTHER INFORMATION: The reverse primer for SNP of specific position
      (chr22:17563259)

<400> SEQUENCE: 578
cactgtgccc agtcaaatat ttttga                                          26

<210> SEQ ID NO 579
<211> LENGTH: 22
<212> TYPE: DNA
<213> ORGANISM: artificial sequence
<220> FEATURE:
<223> OTHER INFORMATION: The forward primer for SNP of specific position
      (chr22:17587785)

<400> SEQUENCE: 579
cgtcatctgg gaagctgttt cc                                              22

<210> SEQ ID NO 580
<211> LENGTH: 26
<212> TYPE: DNA
<213> ORGANISM: artificial sequence
<220> FEATURE:
<223> OTHER INFORMATION: The reverse primer for SNP of specific position
      (chr22:17587785)

<400> SEQUENCE: 580
gtgcaggaca cttcggaaaa cagaag                                          26

<210> SEQ ID NO 581
<211> LENGTH: 25
<212> TYPE: DNA
<213> ORGANISM: artificial sequence
<220> FEATURE:
<223> OTHER INFORMATION: The forward primer for SNP of specific position
      (chr22:17619511)

<400> SEQUENCE: 581
aaatcaatgt tgcaaagcaa aggga                                           25

<210> SEQ ID NO 582
<211> LENGTH: 23
<212> TYPE: DNA
<213> ORGANISM: artificial sequence
<220> FEATURE:
<223> OTHER INFORMATION: The reverse primer for SNP of specific position
      (chr22:17619511)

<400> SEQUENCE: 582
agcatcctca cttaccagta tgc                                             23

<210> SEQ ID NO 583
```

```
<211> LENGTH: 30
<212> TYPE: DNA
<213> ORGANISM: artificial sequence
<220> FEATURE:
<223> OTHER INFORMATION: The forward primer for SNP of specific position
      (chr22:17656792)

<400> SEQUENCE: 583
aaaatcacca tttgatggtt gtattttcca                                    30

<210> SEQ ID NO 584
<211> LENGTH: 26
<212> TYPE: DNA
<213> ORGANISM: artificial sequence
<220> FEATURE:
<223> OTHER INFORMATION: The reverse primer for SNP of specific position
      (chr22:17656792)

<400> SEQUENCE: 584
cattatttct gccatacttc gttggt                                        26

<210> SEQ ID NO 585
<211> LENGTH: 27
<212> TYPE: DNA
<213> ORGANISM: artificial sequence
<220> FEATURE:
<223> OTHER INFORMATION: The forward primer for SNP of specific position
      (chr22:17682387)

<400> SEQUENCE: 585
cagcattctg actttcttgt ttacaca                                       27

<210> SEQ ID NO 586
<211> LENGTH: 29
<212> TYPE: DNA
<213> ORGANISM: artificial sequence
<220> FEATURE:
<223> OTHER INFORMATION: The reverse primer for SNP of specific position
      (chr22:17682387)

<400> SEQUENCE: 586
agagagtctg ctcgttcatt tacatattg                                     29

<210> SEQ ID NO 587
<211> LENGTH: 25
<212> TYPE: DNA
<213> ORGANISM: artificial sequence
<220> FEATURE:
<223> OTHER INFORMATION: The forward primer for SNP of specific position
      (chr22:17715164)

<400> SEQUENCE: 587
ggagacaggt tcacatgaaa aagtt                                         25

<210> SEQ ID NO 588
<211> LENGTH: 22
<212> TYPE: DNA
<213> ORGANISM: artificial sequence
<220> FEATURE:
<223> OTHER INFORMATION: The reverse primer for SNP of specific position
      (chr22:17715164)

<400> SEQUENCE: 588
gtgaaagcag gagcttcttg ga                                            22

<210> SEQ ID NO 589
<211> LENGTH: 22
```

```
<212> TYPE: DNA
<213> ORGANISM: artificial sequence
<220> FEATURE:
<223> OTHER INFORMATION: The forward primer for SNP of specific position
      (chr22:17739757)

<400> SEQUENCE: 589
cccaaggaaa acgggtttat gg                                              22

<210> SEQ ID NO 590
<211> LENGTH: 22
<212> TYPE: DNA
<213> ORGANISM: artificial sequence
<220> FEATURE:
<223> OTHER INFORMATION: The reverse primer for SNP of specific position
      (chr22:17739757)

<400> SEQUENCE: 590
cacacatgtg catgctactg aa                                              22

<210> SEQ ID NO 591
<211> LENGTH: 30
<212> TYPE: DNA
<213> ORGANISM: artificial sequence
<220> FEATURE:
<223> OTHER INFORMATION: The forward primer for SNP of specific position
      (chr22:17761489)

<400> SEQUENCE: 591
aagaaacttg gtttcatttt ccattaaggt                                      30

<210> SEQ ID NO 592
<211> LENGTH: 26
<212> TYPE: DNA
<213> ORGANISM: artificial sequence
<220> FEATURE:
<223> OTHER INFORMATION: The reverse primer for SNP of specific position
      (chr22:17761489)

<400> SEQUENCE: 592
agtaataagc aacccaaact tagcca                                          26

<210> SEQ ID NO 593
<211> LENGTH: 23
<212> TYPE: DNA
<213> ORGANISM: artificial sequence
<220> FEATURE:
<223> OTHER INFORMATION: The forward primer for SNP of specific position
      (chr22:17785311)

<400> SEQUENCE: 593
tggctctgac ttcatgatca tgg                                             23

<210> SEQ ID NO 594
<211> LENGTH: 26
<212> TYPE: DNA
<213> ORGANISM: artificial sequence
<220> FEATURE:
<223> OTHER INFORMATION: The reverse primer for SNP of specific position
      (chr22:17785311)

<400> SEQUENCE: 594
ggcttggaag cataagtagg atgtag                                          26

<210> SEQ ID NO 595
<211> LENGTH: 22
<212> TYPE: DNA
```

```
<213> ORGANISM: artificial sequence
<220> FEATURE:
<223> OTHER INFORMATION: The forward primer for SNP of specific position
      (chr22:17805528)

<400> SEQUENCE: 595
ccagcctgcc aacacaatat tg                                                  22

<210> SEQ ID NO 596
<211> LENGTH: 29
<212> TYPE: DNA
<213> ORGANISM: artificial sequence
<220> FEATURE:
<223> OTHER INFORMATION: The reverse primer for SNP of specific position
      (chr22:17805528)

<400> SEQUENCE: 596
ccattaactg tatctatgct tgtctgtct                                           29

<210> SEQ ID NO 597
<211> LENGTH: 29
<212> TYPE: DNA
<213> ORGANISM: artificial sequence
<220> FEATURE:
<223> OTHER INFORMATION: The forward primer for SNP of specific position
      (chr22:17841251)

<400> SEQUENCE: 597
tatggaaatc actgaaaagt ggagaaact                                           29

<210> SEQ ID NO 598
<211> LENGTH: 29
<212> TYPE: DNA
<213> ORGANISM: artificial sequence
<220> FEATURE:
<223> OTHER INFORMATION: The reverse primer for SNP of specific position
      (chr22:17841251)

<400> SEQUENCE: 598
gttttgtttg ttttttcaaat ggtgtctca                                          29

<210> SEQ ID NO 599
<211> LENGTH: 27
<212> TYPE: DNA
<213> ORGANISM: artificial sequence
<220> FEATURE:
<223> OTHER INFORMATION: The forward primer for SNP of specific position
      (chr22:17883346)

<400> SEQUENCE: 599
ttggaaattc tttcaggttg actcctt                                             27

<210> SEQ ID NO 600
<211> LENGTH: 30
<212> TYPE: DNA
<213> ORGANISM: artificial sequence
<220> FEATURE:
<223> OTHER INFORMATION: The reverse primer for SNP of specific position
      (chr22:17883346)

<400> SEQUENCE: 600
aaaacaagtt tgccagtttc tttagaagtt                                          30

<210> SEQ ID NO 601
<211> LENGTH: 30
<212> TYPE: DNA
<213> ORGANISM: artificial sequence
```

```
<220> FEATURE:
<223> OTHER INFORMATION: The forward primer for SNP of specific position
      (chr22:17916190)

<400> SEQUENCE: 601
gggaaaagga ttttgtattt catgtcatcc                                              30

<210> SEQ ID NO 602
<211> LENGTH: 22
<212> TYPE: DNA
<213> ORGANISM: artificial sequence
<220> FEATURE:
<223> OTHER INFORMATION: The reverse primer for SNP of specific position
      (chr22:17916190)

<400> SEQUENCE: 602
ggcaagacca tctaatggca ct                                                      22

<210> SEQ ID NO 603
<211> LENGTH: 22
<212> TYPE: DNA
<213> ORGANISM: artificial sequence
<220> FEATURE:
<223> OTHER INFORMATION: The forward primer for SNP of specific position
      (chr22:17939998)

<400> SEQUENCE: 603
cccggtatcc ttatgtccca gt                                                      22

<210> SEQ ID NO 604
<211> LENGTH: 23
<212> TYPE: DNA
<213> ORGANISM: artificial sequence
<220> FEATURE:
<223> OTHER INFORMATION: The reverse primer for SNP of specific position
      (chr22:17939998)

<400> SEQUENCE: 604
ggatggaact aaaggccagc taa                                                     23

<210> SEQ ID NO 605
<211> LENGTH: 27
<212> TYPE: DNA
<213> ORGANISM: artificial sequence
<220> FEATURE:
<223> OTHER INFORMATION: The forward primer for SNP of specific position
      (chr22:17981144)

<400> SEQUENCE: 605
tttttccttt agagctgtgt gtgtaag                                                 27

<210> SEQ ID NO 606
<211> LENGTH: 30
<212> TYPE: DNA
<213> ORGANISM: artificial sequence
<220> FEATURE:
<223> OTHER INFORMATION: The reverse primer for SNP of specific position
      (chr22:17981144)

<400> SEQUENCE: 606
gcaaagtgta taacgcatta ggatgaagta                                              30

<210> SEQ ID NO 607
<211> LENGTH: 23
<212> TYPE: DNA
<213> ORGANISM: artificial sequence
<220> FEATURE:
```

<223> OTHER INFORMATION: The forward primer for SNP of specific position
(chr22:18012297)

<400> SEQUENCE: 607
gtggcctttc cagcttctag tag                                               23

<210> SEQ ID NO 608
<211> LENGTH: 29
<212> TYPE: DNA
<213> ORGANISM: artificial sequence
<220> FEATURE:
<223> OTHER INFORMATION: The reverse primer for SNP of specific position
(chr22:18012297)

<400> SEQUENCE: 608
tttcaagtca tacaccacct caaatatgt                                         29

<210> SEQ ID NO 609
<211> LENGTH: 25
<212> TYPE: DNA
<213> ORGANISM: artificial sequence
<220> FEATURE:
<223> OTHER INFORMATION: The forward primer for SNP of specific position
(chr22:18054406)

<400> SEQUENCE: 609
ctgacatggt gtcatacacc tatgg                                             25

<210> SEQ ID NO 610
<211> LENGTH: 22
<212> TYPE: DNA
<213> ORGANISM: artificial sequence
<220> FEATURE:
<223> OTHER INFORMATION: The reverse primer for SNP of specific position
(chr22:18054406)

<400> SEQUENCE: 610
acagcatgtg ccctcctaaa ag                                                22

<210> SEQ ID NO 611
<211> LENGTH: 29
<212> TYPE: DNA
<213> ORGANISM: artificial sequence
<220> FEATURE:
<223> OTHER INFORMATION: The forward primer for SNP of specific position
(chr22:18212058)

<400> SEQUENCE: 611
aatactttac ctaccctgat caccaaaac                                         29

<210> SEQ ID NO 612
<211> LENGTH: 25
<212> TYPE: DNA
<213> ORGANISM: artificial sequence
<220> FEATURE:
<223> OTHER INFORMATION: The reverse primer for SNP of specific position
(chr22:18212058)

<400> SEQUENCE: 612
acatcactcc ctaaatggga cacta                                             25

<210> SEQ ID NO 613
<211> LENGTH: 22
<212> TYPE: DNA
<213> ORGANISM: artificial sequence
<220> FEATURE:
<223> OTHER INFORMATION: The forward primer for SNP of specific position (chr22:18276198)

<400> SEQUENCE: 613
ccacatgcct ttcaacgaca at                                              22

<210> SEQ ID NO 614
<211> LENGTH: 24
<212> TYPE: DNA
<213> ORGANISM: artificial sequence
<220> FEATURE:
<223> OTHER INFORMATION: The reverse primer for SNP of specific position
     (chr22:18276198)

<400> SEQUENCE: 614
gggctttaag tctcagatcc atca                                            24

<210> SEQ ID NO 615
<211> LENGTH: 28
<212> TYPE: DNA
<213> ORGANISM: artificial sequence
<220> FEATURE:
<223> OTHER INFORMATION: The forward primer for SNP of specific position
     (chr22:18354015)

<400> SEQUENCE: 615
ttctatcaat gtcaaggtct ttatgcca                                        28

<210> SEQ ID NO 616
<211> LENGTH: 22
<212> TYPE: DNA
<213> ORGANISM: artificial sequence
<220> FEATURE:
<223> OTHER INFORMATION: The reverse primer for SNP of specific position
     (chr22:18354015)

<400> SEQUENCE: 616
gcaacatgtg ctgccagttt tt                                              22

<210> SEQ ID NO 617
<211> LENGTH: 30
<212> TYPE: DNA
<213> ORGANISM: artificial sequence
<220> FEATURE:
<223> OTHER INFORMATION: The forward primer for SNP of specific position
     (chr22:18395978)

<400> SEQUENCE: 617
atggctttta ctaggtgaag gtaattttct                                      30

<210> SEQ ID NO 618
<211> LENGTH: 30
<212> TYPE: DNA
<213> ORGANISM: artificial sequence
<220> FEATURE:
<223> OTHER INFORMATION: The reverse primer for SNP of specific position
     (chr22:18395978)

<400> SEQUENCE: 618
agagacattt aaataatgtc cttgcagagt                                      30

<210> SEQ ID NO 619
<211> LENGTH: 22
<212> TYPE: DNA
<213> ORGANISM: artificial sequence
<220> FEATURE:
<223> OTHER INFORMATION: The forward primer for SNP of specific position
     (chr22:18466951)

```
<400> SEQUENCE: 619
ggcaaaacgc aaatcatcgt ga                                              22

<210> SEQ ID NO 620
<211> LENGTH: 22
<212> TYPE: DNA
<213> ORGANISM: artificial sequence
<220> FEATURE:
<223> OTHER INFORMATION: The reverse primer for SNP of specific position
      (chr22:18466951)

<400> SEQUENCE: 620
ggaccaggga aatcctgagt ct                                              22

<210> SEQ ID NO 621
<211> LENGTH: 23
<212> TYPE: DNA
<213> ORGANISM: artificial sequence
<220> FEATURE:
<223> OTHER INFORMATION: The forward primer for SNP of specific position
      (chr22:18531582)

<400> SEQUENCE: 621
tgaccctctt agaacccatt cct                                             23

<210> SEQ ID NO 622
<211> LENGTH: 28
<212> TYPE: DNA
<213> ORGANISM: artificial sequence
<220> FEATURE:
<223> OTHER INFORMATION: The reverse primer for SNP of specific position
      (chr22:18531582)

<400> SEQUENCE: 622
aggagaggct tttaaaatcg ctatgatt                                        28

<210> SEQ ID NO 623
<211> LENGTH: 29
<212> TYPE: DNA
<213> ORGANISM: artificial sequence
<220> FEATURE:
<223> OTHER INFORMATION: The forward primer for SNP of specific position
      (chr22:18581715)

<400> SEQUENCE: 623
agatgcatga aatggctaca tagatatgg                                       29

<210> SEQ ID NO 624
<211> LENGTH: 30
<212> TYPE: DNA
<213> ORGANISM: artificial sequence
<220> FEATURE:
<223> OTHER INFORMATION: The reverse primer for SNP of specific position
      (chr22:18581715)

<400> SEQUENCE: 624
gttgatttgt ggttgcctat gtaattgtat                                      30

<210> SEQ ID NO 625
<211> LENGTH: 23
<212> TYPE: DNA
<213> ORGANISM: artificial sequence
<220> FEATURE:
<223> OTHER INFORMATION: The forward primer for SNP of specific position
      (chr22:18628321)
```

-continued

<400> SEQUENCE: 625
ggcccacact ttcttttgaa aca                                              23

<210> SEQ ID NO 626
<211> LENGTH: 24
<212> TYPE: DNA
<213> ORGANISM: artificial sequence
<220> FEATURE:
<223> OTHER INFORMATION: The reverse primer for SNP of specific position
      (chr22:18628321)

<400> SEQUENCE: 626
gggatttggg agaaatgcaa tgtc                                             24

<210> SEQ ID NO 627
<211> LENGTH: 22
<212> TYPE: DNA
<213> ORGANISM: artificial sequence
<220> FEATURE:
<223> OTHER INFORMATION: The forward primer for SNP of specific position
      (chr22:18894617)

<400> SEQUENCE: 627 cgccttttg gtgaccaatg tg                                                22

<210> SEQ ID NO 628
<211> LENGTH: 22
<212> TYPE: DNA
<213> ORGANISM: artificial sequence
<220> FEATURE:
<223> OTHER INFORMATION: The reverse primer for SNP of specific position
      (chr22:18894617)

<400> SEQUENCE: 628
gctgtcaaca gacctccaac ta                                               22

<210> SEQ ID NO 629
<211> LENGTH: 22
<212> TYPE: DNA
<213> ORGANISM: artificial sequence
<220> FEATURE:
<223> OTHER INFORMATION: The forward primer for SNP of specific position
      (chr22:18966077)

<400> SEQUENCE: 629
ctgtgctcta aagccagact ga                                               22

<210> SEQ ID NO 630
<211> LENGTH: 22
<212> TYPE: DNA
<213> ORGANISM: artificial sequence
<220> FEATURE:
<223> OTHER INFORMATION: The reverse primer for SNP of specific position
      (chr22:18966077)

<400> SEQUENCE: 630
ctctgtacac tgccacatac ca                                               22

<210> SEQ ID NO 631
<211> LENGTH: 24
<212> TYPE: DNA
<213> ORGANISM: artificial sequence
<220> FEATURE:
<223> OTHER INFORMATION: The forward primer for SNP of specific position
      (chr22:19004846)

<400> SEQUENCE: 631
gctgtatacg acaaagccat agct                                          24

<210> SEQ ID NO 632
<211> LENGTH: 29
<212> TYPE: DNA
<213> ORGANISM: artificial sequence
<220> FEATURE:
<223> OTHER INFORMATION: The reverse primer for SNP of specific position
      (chr22:19004846)

<400> SEQUENCE: 632
tttttctctt gcatatttgt gtgatgtct                                     29

<210> SEQ ID NO 633
<211> LENGTH: 22
<212> TYPE: DNA
<213> ORGANISM: artificial sequence
<220> FEATURE:
<223> OTHER INFORMATION: The forward primer for SNP of specific position
      (chr22:19025459)

<400> SEQUENCE: 633
ctgtgtcagg caacaaaacc ac                                            22

<210> SEQ ID NO 634
<211> LENGTH: 22
<212> TYPE: DNA
<213> ORGANISM: artificial sequence
<220> FEATURE:
<223> OTHER INFORMATION: The reverse primer for SNP of specific position
      (chr22:19025459)

<400> SEQUENCE: 634
cccatttgtg ccataaaggg tt                                            22

<210> SEQ ID NO 635
<211> LENGTH: 27
<212> TYPE: DNA
<213> ORGANISM: artificial sequence
<220> FEATURE:
<223> OTHER INFORMATION: The forward primer for SNP of specific position
      (chr22:19098323)

<400> SEQUENCE: 635
cagaaggaga aagacaagga gtagatg                                       27

<210> SEQ ID NO 636
<211> LENGTH: 30
<212> TYPE: DNA
<213> ORGANISM: artificial sequence
<220> FEATURE:
<223> OTHER INFORMATION: The reverse primer for SNP of specific position
      (chr22:19098323)

<400> SEQUENCE: 636
cctcatttta cagatagaga aacagagctt                                    30

<210> SEQ ID NO 637
<211> LENGTH: 22
<212> TYPE: DNA
<213> ORGANISM: artificial sequence
<220> FEATURE:
<223> OTHER INFORMATION: The forward primer for SNP of specific position
      (chr22:19142652)

<400> SEQUENCE: 637
caccaggccc tcatctctta ac                                             22

<210> SEQ ID NO 638
<211> LENGTH: 22
<212> TYPE: DNA
<213> ORGANISM: artificial sequence
<220> FEATURE:
<223> OTHER INFORMATION: The reverse primer for SNP of specific position
      (chr22:19142652)

<400> SEQUENCE: 638
atgagggcaa agactcccaa ac                                             22

<210> SEQ ID NO 639
<211> LENGTH: 23
<212> TYPE: DNA
<213> ORGANISM: artificial sequence
<220> FEATURE:
<223> OTHER INFORMATION: The forward primer for SNP of specific position
      (chr22:19236590)

<400> SEQUENCE: 639
gcctggccct tctaagagtt tta                                            23

<210> SEQ ID NO 640
<211> LENGTH: 30
<212> TYPE: DNA
<213> ORGANISM: artificial sequence
<220> FEATURE:
<223> OTHER INFORMATION: The reverse primer for SNP of specific position
      (chr22:19236590)

<400> SEQUENCE: 640
catgatcatt tgaacttatt cctccagtct                                     30

<210> SEQ ID NO 641
<211> LENGTH: 22
<212> TYPE: DNA
<213> ORGANISM: artificial sequence
<220> FEATURE:
<223> OTHER INFORMATION: The forward primer for SNP of specific position
      (chr22:19362714)

<400> SEQUENCE: 641
cctctcagga ggcagagaac tt                                             22

<210> SEQ ID NO 642
<211> LENGTH: 30
<212> TYPE: DNA
<213> ORGANISM: artificial sequence
<220> FEATURE:
<223> OTHER INFORMATION: The reverse primer for SNP of specific position
      (chr22:19362714)

<400> SEQUENCE: 642
ggtagagagc tgcaataaaa atgatgtaag                                     30

<210> SEQ ID NO 643
<211> LENGTH: 22
<212> TYPE: DNA
<213> ORGANISM: artificial sequence
<220> FEATURE:
<223> OTHER INFORMATION: The forward primer for SNP of specific position
      (chr22:19431588)

<400> SEQUENCE: 643
caggcagttt cccaaggact ag                                             22

<210> SEQ ID NO 644
<211> LENGTH: 22
<212> TYPE: DNA
<213> ORGANISM: artificial sequence
<220> FEATURE:
<223> OTHER INFORMATION: The reverse primer for SNP of specific position
      (chr22:19431588)

<400> SEQUENCE: 644 gatacccctga cactgcgatg tt                                      22

<210> SEQ ID NO 645
<211> LENGTH: 19
<212> TYPE: DNA
<213> ORGANISM: artificial sequence
<220> FEATURE:
<223> OTHER INFORMATION: The forward primer for SNP of specific position
      (chr22:19536367)

<400> SEQUENCE: 645
cgtgagtctg ggtgacagt                                           19

<210> SEQ ID NO 646
<211> LENGTH: 23
<212> TYPE: DNA
<213> ORGANISM: artificial sequence
<220> FEATURE:
<223> OTHER INFORMATION: The reverse primer for SNP of specific position
      (chr22:19536367)

<400> SEQUENCE: 646
gggagcacat cagcattgta tca                                      23

<210> SEQ ID NO 647
<211> LENGTH: 30
<212> TYPE: DNA
<213> ORGANISM: artificial sequence
<220> FEATURE:
<223> OTHER INFORMATION: The forward primer for SNP of specific position
      (chr22:19643965)

<400> SEQUENCE: 647
ataccaagaa acccaagaaa gaaagggtga                               30

<210> SEQ ID NO 648
<211> LENGTH: 22
<212> TYPE: DNA
<213> ORGANISM: artificial sequence
<220> FEATURE:
<223> OTHER INFORMATION: The reverse primer for SNP of specific position
      (chr22:19643965)

<400> SEQUENCE: 648
ggaagcttct ccaaggtaag ct                                       22

<210> SEQ ID NO 649
<211> LENGTH: 22
<212> TYPE: DNA
<213> ORGANISM: artificial sequence
<220> FEATURE:
<223> OTHER INFORMATION: The forward primer for SNP of specific position
      (chr22:19716983)

<400> SEQUENCE: 649
cacctccaga ggtcctagtg ta                                       22

```
<210> SEQ ID NO 650
<211> LENGTH: 22
<212> TYPE: DNA
<213> ORGANISM: artificial sequence
<220> FEATURE:
<223> OTHER INFORMATION: The reverse primer for SNP of specific position
      (chr22:19716983)

<400> SEQUENCE: 650
cactttctcc tgggctgtac at                                             22

<210> SEQ ID NO 651
<211> LENGTH: 22
<212> TYPE: DNA
<213> ORGANISM: artificial sequence
<220> FEATURE:
<223> OTHER INFORMATION: The forward primer for SNP of specific position
      (chr22:19759532)

<400> SEQUENCE: 651
gggtctcagc ctaactgaag ga                                             22

<210> SEQ ID NO 652
<211> LENGTH: 24
<212> TYPE: DNA
<213> ORGANISM: artificial sequence
<220> FEATURE:
<223> OTHER INFORMATION: The reverse primer for SNP of specific position
      (chr22:19759532)

<400> SEQUENCE: 652
gggaggagtg tcctgagaaa tgat                                           24

<210> SEQ ID NO 653
<211> LENGTH: 21
<212> TYPE: DNA
<213> ORGANISM: artificial sequence
<220> FEATURE:
<223> OTHER INFORMATION: The forward primer for SNP of specific position
      (chr22:19808057)

<400> SEQUENCE: 653
catgaagggt ccagtggaga t                                              21

<210> SEQ ID NO 654
<211> LENGTH: 23
<212> TYPE: DNA
<213> ORGANISM: artificial sequence
<220> FEATURE:
<223> OTHER INFORMATION: The reverse primer for SNP of specific position
      (chr22:19808057)

<400> SEQUENCE: 654
ggagtcagga actctctgat gga                                            23

<210> SEQ ID NO 655
<211> LENGTH: 19
<212> TYPE: DNA
<213> ORGANISM: artificial sequence
<220> FEATURE:
<223> OTHER INFORMATION: The forward primer for SNP of specific position
      (chr22:19859087)

<400> SEQUENCE: 655
cgccagcgtg tacctcttt                                                 19
```

```
<210> SEQ ID NO 656
<211> LENGTH: 19
<212> TYPE: DNA
<213> ORGANISM: artificial sequence
<220> FEATURE:
<223> OTHER INFORMATION: The reverse primer for SNP of specific position
      (chr22:19859087)

<400> SEQUENCE: 656
ggcacgggag catcctatg                                                      19

<210> SEQ ID NO 657
<211> LENGTH: 22
<212> TYPE: DNA
<213> ORGANISM: artificial sequence
<220> FEATURE:
<223> OTHER INFORMATION: The forward primer for SNP of specific position
      (chr22:19909387)

<400> SEQUENCE: 657
ccagaggtca tgcacagaag ac                                                  22

<210> SEQ ID NO 658
<211> LENGTH: 25
<212> TYPE: DNA
<213> ORGANISM: artificial sequence
<220> FEATURE:
<223> OTHER INFORMATION: The reverse primer for SNP of specific position
      (chr22:19909387)

<400> SEQUENCE: 658
tatgcttttc ccagtccaga ttctg                                               25

<210> SEQ ID NO 659
<211> LENGTH: 22
<212> TYPE: DNA
<213> ORGANISM: artificial sequence
<220> FEATURE:
<223> OTHER INFORMATION: The forward primer for SNP of specific position
      (chr22:19972494)

<400> SEQUENCE: 659
accgtgtatc ggagaccctt at                                                  22

<210> SEQ ID NO 660
<211> LENGTH: 22
<212> TYPE: DNA
<213> ORGANISM: artificial sequence
<220> FEATURE:
<223> OTHER INFORMATION: The reverse primer for SNP of specific position
      (chr22:19972494)

<400> SEQUENCE: 660
cagccaactc ctgttgagag tc                                                  22

<210> SEQ ID NO 661
<211> LENGTH: 22
<212> TYPE: DNA
<213> ORGANISM: artificial sequence
<220> FEATURE:
<223> OTHER INFORMATION: The forward primer for SNP of specific position
      (chr22:20016622)

<400> SEQUENCE: 661
ctgagagcca gggaagcaga tc                                                  22

<210> SEQ ID NO 662
```

```
<211> LENGTH: 23
<212> TYPE: DNA
<213> ORGANISM: artificial sequence
<220> FEATURE:
<223> OTHER INFORMATION: The reverse primer for SNP of specific position
      (chr22:20016622)

<400> SEQUENCE: 662
tcactccatg cggtgtctaa aaa                                              23

<210> SEQ ID NO 663
<211> LENGTH: 22
<212> TYPE: DNA
<213> ORGANISM: artificial sequence
<220> FEATURE:
<223> OTHER INFORMATION: The forward primer for SNP of specific position
      (chr22:20051573)

<400> SEQUENCE: 663
tgcagggtgt catttccttc ag                                               22

<210> SEQ ID NO 664
<211> LENGTH: 23
<212> TYPE: DNA
<213> ORGANISM: artificial sequence
<220> FEATURE:
<223> OTHER INFORMATION: The reverse primer for SNP of specific position
      (chr22:20051573)

<400> SEQUENCE: 664
gaagcaaaca ttcagcacac tct                                              23

<210> SEQ ID NO 665
<211> LENGTH: 23
<212> TYPE: DNA
<213> ORGANISM: artificial sequence
<220> FEATURE:
<223> OTHER INFORMATION: The forward primer for SNP of specific position
      (chr22:20081918)

<400> SEQUENCE: 665
ctatagacag cttggctcca tgt                                              23

<210> SEQ ID NO 666
<211> LENGTH: 22
<212> TYPE: DNA
<213> ORGANISM: artificial sequence
<220> FEATURE:
<223> OTHER INFORMATION: The reverse primer for SNP of specific position
      (chr22:20081918)

<400> SEQUENCE: 666
ggcacgtgag aaaacagctt tg                                               22

<210> SEQ ID NO 667
<211> LENGTH: 20
<212> TYPE: DNA
<213> ORGANISM: artificial sequence
<220> FEATURE:
<223> OTHER INFORMATION: The forward primer for SNP of specific position
      (chr22:20135421)

<400> SEQUENCE: 667
gccttaactt cctggagcca                                                  20

<210> SEQ ID NO 668
<211> LENGTH: 22
```

```
<212> TYPE: DNA
<213> ORGANISM: artificial sequence
<220> FEATURE:
<223> OTHER INFORMATION: The reverse primer for SNP of specific position
      (chr22:20135421)

<400> SEQUENCE: 668
cccaaatggg agatgtagag cc                                              22

<210> SEQ ID NO 669
<211> LENGTH: 22
<212> TYPE: DNA
<213> ORGANISM: artificial sequence
<220> FEATURE:
<223> OTHER INFORMATION: The forward primer for SNP of specific position
      (chr22:20175034)

<400> SEQUENCE: 669
gggatgcatt gcagtaaaga gc                                              22

<210> SEQ ID NO 670
<211> LENGTH: 23
<212> TYPE: DNA
<213> ORGANISM: artificial sequence
<220> FEATURE:
<223> OTHER INFORMATION: The reverse primer for SNP of specific position
      (chr22:20175034)

<400> SEQUENCE: 670
cccattccct gtcactgtta tca                                             23

<210> SEQ ID NO 671
<211> LENGTH: 22
<212> TYPE: DNA
<213> ORGANISM: artificial sequence
<220> FEATURE:
<223> OTHER INFORMATION: The forward primer for SNP of specific position
      (chr22:20216874)

<400> SEQUENCE: 671
ggctacagag acatgaaccc aa                                              22

<210> SEQ ID NO 672
<211> LENGTH: 22
<212> TYPE: DNA
<213> ORGANISM: artificial sequence
<220> FEATURE:
<223> OTHER INFORMATION: The reverse primer for SNP of specific position
      (chr22:20216874)

<400> SEQUENCE: 672
ggctcatggc atgaacttgc ta                                              22

<210> SEQ ID NO 673
<211> LENGTH: 24
<212> TYPE: DNA
<213> ORGANISM: artificial sequence
<220> FEATURE:
<223> OTHER INFORMATION: The forward primer for SNP of specific position
      (chr22:20278637)

<400> SEQUENCE: 673
gggacagtag acaagcttat ccct                                            24

<210> SEQ ID NO 674
<211> LENGTH: 25
<212> TYPE: DNA
```

```
<213> ORGANISM: artificial sequence
<220> FEATURE:
<223> OTHER INFORMATION: The reverse primer for SNP of specific position
      (chr22:20278637)

<400> SEQUENCE: 674
gtcgagatgc ttaatagagc cacat                                           25

<210> SEQ ID NO 675
<211> LENGTH: 24
<212> TYPE: DNA
<213> ORGANISM: artificial sequence
<220> FEATURE:
<223> OTHER INFORMATION: The forward primer for SNP of specific position
      (chr22:20745699)

<400> SEQUENCE: 675
agaaagactc agacctgacc tgtt                                            24

<210> SEQ ID NO 676
<211> LENGTH: 22
<212> TYPE: DNA
<213> ORGANISM: artificial sequence
<220> FEATURE:
<223> OTHER INFORMATION: The reverse primer for SNP of specific position
      (chr22:20745699)

<400> SEQUENCE: 676
acctgtgcac aggtgactct at                                              22

<210> SEQ ID NO 677
<211> LENGTH: 22
<212> TYPE: DNA
<213> ORGANISM: artificial sequence
<220> FEATURE:
<223> OTHER INFORMATION: The forward primer for SNP of specific position
      (chr22:20787955)

<400> SEQUENCE: 677
ggatagactg gccctacacc at                                              22

<210> SEQ ID NO 678
<211> LENGTH: 25
<212> TYPE: DNA
<213> ORGANISM: artificial sequence
<220> FEATURE:
<223> OTHER INFORMATION: The reverse primer for SNP of specific position
      (chr22:20787955)

<400> SEQUENCE: 678
gtggaaaata cactggacca attcc                                           25

<210> SEQ ID NO 679
<211> LENGTH: 28
<212> TYPE: DNA
<213> ORGANISM: artificial sequence
<220> FEATURE:
<223> OTHER INFORMATION: The forward primer for SNP of specific position
      (chr22:20855585)

<400> SEQUENCE: 679
aaaaagaaga tggcgtaatc agaagttg                                        28

<210> SEQ ID NO 680
<211> LENGTH: 26
<212> TYPE: DNA
<213> ORGANISM: artificial sequence
```

<220> FEATURE:
<223> OTHER INFORMATION: The reverse primer for SNP of specific position
      (chr22:20855585)

<400> SEQUENCE: 680
gcagaagcaa atggaaagga gaaatc                                          26

<210> SEQ ID NO 681
<211> LENGTH: 24
<212> TYPE: DNA
<213> ORGANISM: artificial sequence
<220> FEATURE:
<223> OTHER INFORMATION: The forward primer for SNP of specific position
      (chr22:20881195)

<400> SEQUENCE: 681
tatcttcagg ctcagtgcta gtga                                            24

<210> SEQ ID NO 682
<211> LENGTH: 22
<212> TYPE: DNA
<213> ORGANISM: artificial sequence
<220> FEATURE:
<223> OTHER INFORMATION: The reverse primer for SNP of specific position
      (chr22:20881195)

<400> SEQUENCE: 682
gaagctggca gaatgaggga at                                              22

<210> SEQ ID NO 683
<211> LENGTH: 22
<212> TYPE: DNA
<213> ORGANISM: artificial sequence
<220> FEATURE:
<223> OTHER INFORMATION: The forward primer for SNP of specific position
      (chr22:20924097)

<400> SEQUENCE: 683
gggtgctcag taatgtcctt ca                                              22

<210> SEQ ID NO 684
<211> LENGTH: 22
<212> TYPE: DNA
<213> ORGANISM: artificial sequence
<220> FEATURE:
<223> OTHER INFORMATION: The reverse primer for SNP of specific position
      (chr22:20924097)

<400> SEQUENCE: 684
cagagacctc caacctcatc ac                                              22

<210> SEQ ID NO 685
<211> LENGTH: 22
<212> TYPE: DNA
<213> ORGANISM: artificial sequence
<220> FEATURE:
<223> OTHER INFORMATION: The forward primer for SNP of specific position
      (chr22:20983921)

<400> SEQUENCE: 685
tatgagcagg tcatggcagg ta                                              22

<210> SEQ ID NO 686
<211> LENGTH: 29
<212> TYPE: DNA
<213> ORGANISM: artificial sequence
<220> FEATURE:

```
<223> OTHER INFORMATION: The reverse primer for SNP of specific position
      (chr22:20983921)

<400> SEQUENCE: 686
cacttaaatg tgaacaaagt gtccattga                                         29

<210> SEQ ID NO 687
<211> LENGTH: 27
<212> TYPE: DNA
<213> ORGANISM: artificial sequence
<220> FEATURE:
<223> OTHER INFORMATION: The forward primer for SNP of specific position
      (chr22:21028224)

<400> SEQUENCE: 687
tcagggaagt ataaaagtga cagggat                                           27

<210> SEQ ID NO 688
<211> LENGTH: 23
<212> TYPE: DNA
<213> ORGANISM: artificial sequence
<220> FEATURE:
<223> OTHER INFORMATION: The reverse primer for SNP of specific position
      (chr22:21028224)

<400> SEQUENCE: 688
cctcagttgc tcatcactgt cat                                               23
```